(12) United States Patent
Furber et al.

(10) Patent No.: US 7,902,181 B2
(45) Date of Patent: Mar. 8, 2011

(54) COMPOUNDS 010

(75) Inventors: Mark Furber, Loughborough (GB); Christopher Andrew Luckhurst, Loughborough (GB); Hitesh Jayantilal Sanganee, Loughborough (GB); Linda Anne Stein, Loughborough (GB); Peter Alan Cage, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/331,719

(22) Filed: Dec. 10, 2008

(65) Prior Publication Data

US 2009/0306042 A1 Dec. 10, 2009

Related U.S. Application Data

(60) Provisional application No. 61/012,972, filed on Dec. 12, 2007.

(51) Int. Cl.
| | |
|---|---|
| A61K 31/4709 | (2006.01) |
| A61K 31/444 | (2006.01) |
| A61K 31/4525 | (2006.01) |
| A61K 31/4535 | (2006.01) |
| A61K 31/454 | (2006.01) |
| A61K 31/4545 | (2006.01) |
| A61K 31/397 | (2006.01) |
| A61K 31/4025 | (2006.01) |
| A61K 31/4155 | (2006.01) |
| C07D 207/12 | (2006.01) |
| C07D 211/60 | (2006.01) |
| C07D 401/12 | (2006.01) |
| C07D 403/12 | (2006.01) |
| C07D 405/12 | (2006.01) |
| C07D 413/12 | (2006.01) |
| C07D 223/08 | (2006.01) |
| C07D 223/10 | (2006.01) |
| C07D 205/04 | (2006.01) |

(52) U.S. Cl. ........... 514/210.2; 514/235.5; 514/314; 514/316; 514/318; 514/326; 514/330; 514/423; 514/406; 544/129; 546/247; 546/186; 546/211; 546/193; 546/208; 546/209; 546/212; 546/175; 548/953; 548/537

(58) Field of Classification Search .................. None
See application file for complete search history.

(56) References Cited

U.S. PATENT DOCUMENTS

2006/0247289 A1 11/2006 Qian et al.

FOREIGN PATENT DOCUMENTS

| WO | WO00/34241 | 6/2000 |
|---|---|---|
| WO | WO01/09110 | 2/2001 |
| WO | WO01/47886 | 7/2001 |
| WO | WO03/002531 | 1/2003 |
| WO | WO03/002553 | 1/2003 |
| WO | WO2004/110988 | 12/2004 |

OTHER PUBLICATIONS

Bioorg. & Med. Chem. Lett. 15:4053 (2005).*
Bondebjerg, J. et al., "Dipeptidyl nitriles as human dipeptidyl peptidase I inhibitors", Bioorganic & Medicinal Chemistry Letters, Pergamon, Elsevier Science GB, vol. 16, No. 13, pp. 3614-3617, (2006).

* cited by examiner

*Primary Examiner*—Yong Chu
*Assistant Examiner*—Michael Barker
(74) *Attorney, Agent, or Firm*—Fish & Richardson P.C.

(57) ABSTRACT

The present invention provides compounds of formula (I)

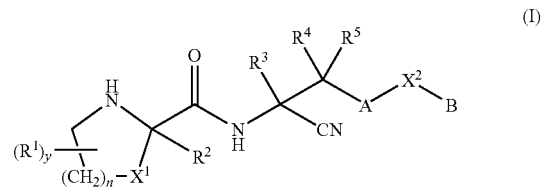

in which n, y, $X^1$, $X^2$, A, B, $R^1$, $R^2$, $R^3$, $R^4$ and $R^5$ are as defined in the specification, a process for their preparation, pharmaceutical compositions containing them and their use in therapy.

13 Claims, No Drawings

COMPOUNDS 010

This application claims the benefit under 35 U.S.C. §119 (e) of U.S. Provisional Application No. 61/012,972, filed on 12 Dec. 2007, which is incorporated herein by reference in its entirety.

The present invention relates to peptidyl nitriles, processes for their preparation, pharmaceutical compositions containing them and their use in therapy.

Dipeptidyl peptidase I (DPPI; EC 3.4.14.1), also known as cathepsin C, is a lysosomal cysteine protease belonging to the papain family having a molecular weight of 200 kDa. DPPI was first discovered by Gutman and Fruton in 1948 (*J Biol Chem*, 174, 851-858); however, the cDNA of the human enzyme was first described in 1995 (Paris et al. 1995, *FEBS Lett*, 369, 326-330). DPPI is the only member of the papain family that is functional as a tetramer, consisting of four identical subunits. Each subunit is composed of an N-terminal fragment, a heavy chain and a light chain (Dolenc et al. 1995, *J Biol Chem*, 270, 21626-21631).

DPPI is constitutively expressed in many tissues with highest levels in lung, kidney, liver and spleen. DPPI catalyses the removal of dipeptides from the N-terminal end of polypeptide substrates with broad specificity. Recent data suggest that besides being an important enzyme in lysosomal protein degradation, DPPI also functions as a key enzyme in the activation of granule serine proteases in cytotoxic T lymphocytes and natural killer cells (granzymes A and B), mast cells (chymase and tryptase) and neutrophils (cathepsin G and elastase).

Mast cells are found in many tissues but are present in greater numbers along the epithelial linings of the body, such as the skin, respiratory tract and gastrointestinal tract. In humans, two types of mast cells have been identified. The T-type, which expresses only tryptase, and the MC-type, which expresses both tryptase and chymase. In humans, the T-type mast cells are located primarily in alveolar tissue and intestinal mucosa while the TC-type cells predominate in skin and conjunctiva. Tryptase and chymase appear to be important mediators of allergic diseases, being involved in processes of inflammation, bronchoconstriction and mucus secretion.

Neutrophils play a critical role in host defense against invading pathogens. Neutrophils are produced in the bone marrow and are fully mature when released into the circulation to take up their role as the first line of cellular defense. Pro-inflammatory mediators and chemotactic attractants activate neutrophils and draw them to the site of infection, where they act to engulf bacteria by phagocytosis, assaulting them with an arsenal of anti-bacterial compounds that use both oxidative and non-oxidative methods of attack. The powerful serine protease, neutrophil elastase, is one of those anti-bacterial compounds that are clearly involved in destroying bacteria. Neutrophil elastase is released into the phagolysome surrounding the microorganism, which it proceeds to destroy. Neutrophil elastase is able to attack the outer membrane protein, OmpA, in gram-negative bacteria, helping to directly kill the pathogen by degrading its membrane, as well as enabling other anti-bacterial compounds to gain access to the pathogen. In addition, neutrophil elastase may help process other anti-bacterial compounds, converting them from inactive pro-peptides into their active states, such as for cathelicidin.

Yet neutrophil elastase can also cause problems for its host. It is one of the most destructive enzymes in the body, with the capability of degrading extracellular matrix proteins (including collagens, proteoglycan, fibronectin, platelet receptors, complement receptor, thrombomodulin, lung surfactant and cadherins) and key plasma proteins (including coagulation and complement factors, immunoglobulin, several proteases and protease inhibitors). Under physiological conditions, endogenous protease inhibitors, such as α1-antitrypsin, tightly regulate the activity of neutrophil elastase. However, at inflammatory sites, neutrophil elastase is able to evade regulation, and once unregulated it can induce the release of pro-inflammatory cytokines, such as interleukin-6 and interleukin-8, leading to acute lung injury. It can even impair host defense against infection by degrading phagocyte surface receptors and opsonins. Its negative role is illustrated by its involvement in the tissue destruction and inflammation that characterise numerous diseases, including hereditary emphysema, chronic obstructive pulmonary disease, cystic fibrosis, adult respiratory distress syndrome, ischemic-reperfusion injury and rheumatoid arthritis.

There is strong evidence associating tryptase and chymase with a number of mast cell mediated allergic, immunological and inflammatory diseases. The fact that neutrophil elastase, cathepsin G and proteinease 3 also seem to play significant roles in these types of diseases point to DPPI being a valid therapeutic target due to its central role in activating these proteases (Adkison et al. 2002, *J Clin Invest*, 109, 363-271; Pham et al. 2004, *J Immunol*, 173, 7277-7281).

In accordance with the present invention, there is therefore provided a compound of formula (I)

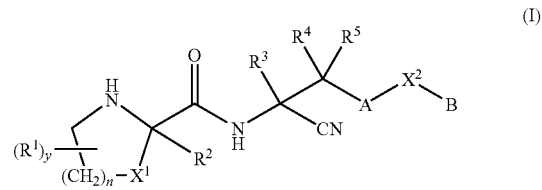

wherein
n independently represents 0, 1, 2, 3 or 4;
$X^1$ represents a methylene group;
y represents 0, 1 or 2;
each $R^1$ independently represents halogen, hydroxyl, carboxyl, cyano, $C_1$-$C_6$ alkyl, $C_1$-$C_6$ alkoxy, trifluoromethyl, $NR^6R^7$, $C(O)NR^6R^7$, $NR^{6a}C(O)R^{7a}$, $SO_2NR^6R^7$, $NR^{6a}SO_2R^{7a}$ or $S(O)_mR^8$ and $R^1$ is optionally substituted with hydroxy, halogen or $C_1$-$C_6$ alkoxy;

$R^2$ represents a hydrogen atom or a $C_1$-$C_6$ alkyl group optionally substituted by at least one substituent selected from halogen, hydroxyl, carboxyl, cyano, trifluoromethyl, $C_1$-$C_6$ alkyl, $C_3$-$C_6$ cycloalkyl, $NR^9R^{10}$, $C(O)NR^{11}R^{12}$, $NR^{13}C(O)R^{14}$, $SO_2NR^{15}R^{16}NR^{17}SO_2R^{18}$ and $S(O)_pR^{19}$;

$R^3$ represents a hydrogen atom or a $C_1$-$C_6$ alkyl group optionally substituted by at least one substituent selected from halogen, hydroxyl, carboxyl, cyano, trifluoromethyl, $C_1$-$C_6$ alkyl, $C_3$-$C_6$ cycloalkyl, $NR^{20}R^{21}$, $C(O)NR^{22}R^{23}$, $NR^{24}C(O)R^{25}$, $SO_2NR^{26}R^{27}$, $NR^{28}SO_2R^{29}$ and $S(O)_qR^{30}$, $R^4$ represents a hydrogen atom or a $C_1$-$C_6$ alkyl group optionally substituted by at least one substituent selected from halogen, hydroxyl, carboxyl, cyano, trifluoromethyl, $C_1$-$C_6$ alkyl, $C_3$-$C_6$ cycloalkyl, $NR^{31}R^{32}$, $C(O)NR^{33}R^{34}$, $NR^{35}C(O)R^{36}$, $SO_2NR^{37}R^{38}$, $NR^{39}SO_2R^{40}$ and $S(O)_rR^{41}$.

$R^5$ represents a hydrogen atom or a $C_1$-$C_6$ alkyl group optionally substituted by at least one substituent selected from halogen, hydroxyl, carboxyl, cyano, trifluoromethyl, $C_1$-$C_6$ alkyl, $C_3$-$C_6$ cycloalkyl, $NR^{42}R^{43}$, $C(O)NR^{44}R^{45}$, $NR^{46}C(O)R^{47}$, $SO_2NR^{48}R^{49}$, $NR^{50}SO_2R^{51}$ and $S(O)_sR^{52}$, or $R^3$ and $R^4$ together with the carbon atoms to which they are attached represent a cyclopropyl ring, or $R^4$ and $R^5$ together with the carbon atom to which they are attached form a saturated or unsaturated, 3- to 6-membered carbocyclic or heterocyclic ring which ring may be optionally substituted with at least one substituent selected from halogen, hydroxyl, carboxyl and $C_1$-$C_6$ alkyl;

A and B each independently represent a 5- to 10-membered aromatic ring system optionally comprising at least one ring heteroatom selected from nitrogen, oxygen and sulphur, the ring system being optionally substituted by at least one substituent selected from halogen, carboxyl, hydroxyl, oxo, nitro, cyano, mercapto, $C_3$-$C_6$ cycloalkyl, $C_2$-$C_6$ alkenyl, trifluoromethyl, $C_1$-$C_6$ alkoxy, $C_1$-$C_6$ alkylcarbonyl, $C_1$-$C_6$ alkylcarbonyloxy, $C_1$-$C_6$ alkoxycarbonyl, —$NR^{53}R^{54}$, —$C(O)NR^{55}R^{56}$, $NR^{57}C(O)R^{58}$, $SO_2NR^{59}R^{60}$, $NR^{61}SO_2R^{62}$, $S(O)_vR^{63}$, saturated 4- to 7-membered heterocyclyloxy, benzyloxy, $C_1$-$C_6$ alkylpiperazinyl and a $C_1$-$C_6$ alkyl group (itself optionally substituted by hydroxyl, $C_1$-$C_6$ alkoxy, $NR^{64}R^{65}$, phenyl or morpholinyl);

m, p, q, r, t and v each independently represent 0, 1 or 2;

$X^2$ represents a bond, an oxygen or sulphur atom, SO, $SO_2$, $NR^{66}$, $C(O)NR^{66}$, $NR^{66}C(O)$, $SO_2NR^{66}$, $NR^{66}SO_2$, $C_1$-$C_3$ alkyl, ethenyl or ethynyl;

$R^6$ and $R^7$ each independently represent hydrogen, $C_1$-$C_6$ alkyl or $C_3$-$C_6$ cycloalkyl, or $R^6$ and $R^7$ together with the nitrogen atom to which they are attached form a 4- to 7-membered saturated heterocyclic ring;

$R^9$ and $R^{10}$ each independently represent hydrogen, $C_1$-$C_6$ alkyl or $C_3$-$C_6$ cycloalkyl, or $R^9$ and $R^{10}$ together with the nitrogen atom to which they are attached form a 4- to 7-membered saturated heterocyclic ring;

$R^{11}$ and $R^{12}$ each independently represent hydrogen, $C_1$-$C_6$ alkyl or $C_3$-$C_6$ cycloalkyl, or $R^{11}$ and $R^{12}$ together with the nitrogen atom to which they are attached form a 4- to 7-membered saturated heterocyclic ring;

$R^{15}$ and $R^{16}$ each independently represent hydrogen, $C_1$-$C_6$ alkyl or $C_3$-$C_6$ cycloalkyl, or $R^{15}$ and $R^{16}$ together with the nitrogen atom to which they are attached form a 4- to 7-membered saturated heterocyclic ring;

$R^{20}$ and $R^{21}$ each independently represent hydrogen, $C_1$-$C_6$ alkyl or $C_3$-$C_6$ cycloalkyl, or $R^{20}$ and $R^{21}$ together with the nitrogen atom to which they are attached form a 4- to 7-membered saturated heterocyclic ring;

$R^{22}$ and $R^{23}$ each independently represent hydrogen, $C_1$-$C_6$ alkyl or $C_3$-$C_6$ cycloalkyl, or $R^{22}$ and $R^{23}$ together with the nitrogen atom to which they are attached form a 4- to 7-membered saturated heterocyclic ring;

$R^{26}$ and $R^{27}$ each independently represent hydrogen, $C_1$-$C_6$ alkyl or $C_3$-$C_6$ cycloalkyl, or $R^{26}$ and $R^{27}$ together with the nitrogen atom to which they are attached form a 4- to 7-membered saturated heterocyclic ring;

$R^{31}$ and $R^{32}$ each independently represent hydrogen, $C_1$-$C_6$ alkyl or $C_3$-$C_6$ cycloalkyl, or $R^{31}$ and $R^{32}$ together with the nitrogen atom to which they are attached form a 4- to 7-membered saturated heterocyclic ring;

$R^{33}$ and $R^{34}$ each independently represent hydrogen, $C_1$-$C_6$ alkyl or $C_3$-$C_6$ cycloalkyl, or $R^{33}$ and $R^{34}$ together with the nitrogen atom to which they are attached form a 4- to 7-membered saturated heterocyclic ring;

$R^{37}$ and $R^{38}$ each independently represent hydrogen, $C_1$-$C_6$ alkyl or $C_3$-$C_6$ cycloalkyl, or $R^{37}$ and $R^{38}$ together with the nitrogen atom to which they are attached form a 4- to 7-membered saturated heterocyclic ring;

$R^{42}$ and $R^{43}$ each independently represent hydrogen, $C_1$-$C_6$ alkyl or $C_3$-$C_6$ cycloalkyl, or $R^{42}$ and $R^{43}$ together with the nitrogen atom to which they are attached form a 4- to 7-membered saturated heterocyclic ring;

$R^{44}$ and $R^{45}$ each independently represent hydrogen, $C_1$-$C_6$ alkyl or $C_3$-$C_6$ cycloalkyl, or $R^{44}$ and $R^{45}$ together with the nitrogen atom to which they are attached form a 4- to 7-membered saturated heterocyclic ring;

$R^{48}$ and $R^{49}$ each independently represent hydrogen, $C_1$-$C_6$ alkyl or $C_3$-$C_6$ cycloalkyl, or $R^{48}$ and $R^{49}$ together with the nitrogen atom to which they are attached form a 4- to 7-membered saturated heterocyclic ring;

$R^{53}$ and $R^{54}$ each independently represent hydrogen, $C_1$-$C_6$ alkyl or $C_3$-$C_6$ cycloalkyl, or $R^{53}$ and $R^{54}$ together with the nitrogen atom to which they are attached form a 4- to 7-membered saturated heterocyclic ring;

$R^{55}$ and $R^{56}$ each independently represent hydrogen, $C_1$-$C_6$ alkyl or $C_3$-$C_6$ cycloalkyl, or $R^{55}$ and $R^{56}$ together with the nitrogen atom to which they are attached form a 4- to 7-membered saturated heterocyclic ring;

$R^{59}$ and $R^{60}$ each independently represent hydrogen, $C_1$-$C_6$ alkyl or $C_3$-$C_6$ cycloalkyl, or $R^{59}$ and $R^{60}$ together with the nitrogen atom to which they are attached form a 4- to 7-membered saturated heterocyclic ring;

$R^{64}$ and $R^{65}$ each independently represent hydrogen, $C_1$-$C_6$ alkyl or $C_3$-$C_6$ cycloalkyl, or $R^{64}$ and $R^{65}$ together with the nitrogen atom to which they are attached form a 4- to 7-membered saturated heterocyclic ring;

each group $R^{6a}$, $R^{7a}$, $R^8$, $R^{13}$, $R^{14}$, $R^{17}$, $R^{18}$, $R^{19}$, $R^{24}$, $R^{25}$, $R^{28}$, $R^{30}$, $R^{35}$, $R^{36}$, $R^{39}$, $R^{40}$, $R^{41}$, $R^{46}$, $R^{47}$, $R^{50}$, $R^{51}$, $R^{52}$, $R^{57}$, $R^{58}$, $R^{61}$, $R^{62}$ and $R^{63}$ independently represents a hydrogen atom or a $C_1$-$C_6$ alkyl or $C_3$-$C_6$ cycloalkyl group; and $R^{66}$ represents a hydrogen atom or a $C_1$-$C_6$ alkyl group; or a pharmaceutically acceptable salt thereof.

In the context of the present specification, unless otherwise stated, an alkyl or alkenyl substituent group or an alkyl or alkenyl moiety in a substituent group may be linear or branched. Examples of $C_1$-$C_6$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. Examples of $C_2$-$C_6$ alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1-hexadienyl.

Similarly, an alkylene group/moiety may be linear or branched. Examples of $C_1$-$C_6$ alkylene groups/moieties include methylene, ethylene, n-propylene, n-butylene, n-pentylene, n-hexylene, 1-methylethylene, 2-methylethylene, 1,2-dimethylethylene, 1-ethylethylene, 2-ethylethylene, 1-, 2- or 3-methylpropylene and 1-, 2- or 3-ethylpropylene.

A $C_3$-$C_6$ cycloalkyl group is a cyclopropyl, cyclobutyl, cyclopentyl or cyclohexyl group.

Where, for example, $R^6$ and $R^7$ both represent a $C_1$-$C_6$ alkyl group or both represent a $C_3$-$C_6$ cycloalkyl group, the alkyl or cycloalkyl groups may be the same as, or different from, one another.

A 4- to 7-membered saturated heterocyclic ring as defined, for example, in $R^6$ and $R^7$ or $R^{20}$ and $R^{21}$ will contain no more than two ring heteroatoms: the nitrogen ring atom to which $R^6$ and $R^7$ or $R^{20}$ and $R^{21}$ are attached and optionally a nitrogen or oxygen ring atom.

A saturated 4- to 7-membered heterocyclyloxy substituent group (as defined in A or B) will contain at least one ring heteroatom selected from nitrogen, oxygen and sulphur, and preferably contains a single nitrogen ring atom.

When $R^4$ and $R^5$ together form a saturated or unsaturated, 3- to 6-membered carbocyclic or heterocyclic ring, it should be understood that the ring may be partially unsaturated but not fully unsaturated. A heterocylic ring will contain at least one ring heteroatom selected from nitrogen, oxygen and sulphur.

For the avoidance of doubt, it should be understood that the definitions of the heterocyclic rings in formula (I) are not intended to include unstable structures or any O—O, O—S or S—S bonds and that a substituent, if present, may be attached to any suitable ring atom provided the resulting compound is not unstable.

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

In an embodiment of the invention, n is 0, 1 or 2, particularly 2.

$X^1$ represents a methylene (—CH$_2$—) group.

In an embodiment of the invention, y is 0.

In another embodiment, y is 1 and $R^1$ represents halogen (e.g. fluorine, chlorine, bromine or iodine), hydroxyl, carboxyl, cyano, $C_1$-$C_6$, or $C_1$-$C_4$, or $C_1$-$C_2$ alkyl (e.g. methyl, ethyl, n-propyl, isopropyl, n-butyl, isobutyl, tert-butyl, n-pentyl or n-hexyl), $C_1$-$C_6$, or $C_1$-$C_4$, or $C_1$-$C_2$ alkoxy (e.g. methoxy, ethoxy, n-propoxy, isopropoxy, n-butoxy, isobutoxy, tert-butoxy, n-pentoxy or n-hexoxy), trifluoromethyl, $NR^6R^7$, $C(O)NR^6R^7$, $NR^{6a}C(O)R^{7a}$, $SO_2NR^6R^7$, $NR^{6a}SO_2R^{7a}$ or $S(O)_mR^8$.

In one embodiment, y is 1 and $R^1$ represents hydroxyl.

$R^2$ represents a hydrogen atom or a $C_1$-$C_6$, or $C_1$-$C_4$, or $C_1$-$C_2$ alkyl group (e.g. methyl, ethyl, n-propyl, isopropyl, n-butyl, isobutyl, tert-butyl, n-pentyl or n-hexyl) optionally substituted by at least one substituent (e.g. one, two, three or four substituents independently) selected from halogen (e.g. fluorine, chlorine, bromine or iodine), hydroxyl, carboxyl, cyano, trifluoromethyl, $C_1$-$C_6$, or $C_1$-$C_4$, or $C_1$-$C_2$ alkyl (e.g. methyl, ethyl, n-propyl, isopropyl, n-butyl, isobutyl, tert-butyl, n-pentyl or n-hexyl), $C_3$-$C_6$ cycloalkyl (cyclopropyl, cyclobutyl, cyclopentyl or cyclohexyl), $NR^9R^{10}$, $C(O)NR^{11}R^{12}$, $NR^{13}C(O)R^{14}$, $SO_2NR^{15}R^{16}$, $NR^{17}SO_2R^{18}$ and $S(O)_pR^{19}$.

In an embodiment of the invention, $R^2$ represents a hydrogen atom.

$R^3$ represents a hydrogen atom or a $C_1$-$C_6$, or $C_1$-$C_4$, or $C_1$-$C_2$ alkyl group (e.g. methyl, ethyl, n-propyl, isopropyl, n-butyl, isobutyl, tert-butyl, n-pentyl or n-hexyl) optionally substituted by at least one substituent (e.g. one, two, three or four substituents independently) selected from halogen (e.g. fluorine, chlorine, bromine or iodine), hydroxyl, carboxyl, cyano, trifluoromethyl, $C_1$-$C_6$, or $C_1$-$C_4$, or $C_1$-$C_2$ alkyl (e.g. methyl, ethyl, n-propyl, isopropyl, n-butyl, isobutyl, tert-butyl, n-pentyl or n-hexyl), $C_3$-$C_6$ cycloalkyl (cyclopropyl, cyclobutyl, cyclopentyl or cyclohexyl), $NR^{20}R^{21}$, $C(O)NR^{22}R^{23}$, $NR^{24}C(O)R^{25}$, $SO_2NR^{26}R^{27}$, $NR^{28}SO_2R^{29}$ and $S(O)_qR^{30}$.

In an embodiment of the invention, $R^3$ represents a hydrogen atom.

$R^4$ represents a hydrogen atom or a $C_1$-$C_6$, or $C_1$-$C_4$, or $C_1$-$C_2$ alkyl group (e.g. methyl, ethyl, n-propyl, isopropyl, n-butyl, isobutyl, tert-butyl, n-pentyl or n-hexyl) optionally substituted by at least one substituent (e.g. one, two, three or four substituents independently) selected from halogen (e.g. fluorine, chlorine, bromine or iodine), hydroxyl, carboxyl, cyano, trifluoromethyl, $C_1$-$C_6$, or $C_1$-$C_4$, or $C_1$-$C_2$ alkyl (e.g. methyl, ethyl, n-propyl, isopropyl, n-butyl, isobutyl, tert-butyl, n-pentyl or n-hexyl), $C_3$-$C_6$ cycloalkyl (cyclopropyl, cyclobutyl, cyclopentyl or cyclohexyl), $NR^{31}R^{32}$, $C(O)NR^{33}R^{34}$, $NR^{35}C(O)R^{36}$, $SO_2NR^{37}R^{38}$, $NR^{39}SO_2R^{40}$ and $S(O)_rR^{41}$.

In an embodiment of the invention, $R^4$ represents a hydrogen atom.

$R^5$ represents a hydrogen atom or a $C_1$-$C_6$, or $C_1$-$C_4$, or $C_1$-$C_2$ alkyl group (e.g. methyl, ethyl, n-propyl, isopropyl, n-butyl, isobutyl, tert-butyl, n-pentyl or n-hexyl) optionally substituted by at least one substituent (e.g. one, two, three or four substituents independently) selected from halogen (e.g. fluorine, chlorine, bromine or iodine), hydroxyl, carboxyl, cyano, trifluoromethyl, $C_1$-$C_6$, or $C_1$-$C_4$, or $C_1$-$C_2$ alkyl (e.g. methyl, ethyl, n-propyl, isopropyl, n-butyl, isobutyl, tert-butyl, n-pentyl or n-hexyl), $C_3$-$C_6$ cycloalkyl (cyclopropyl, cyclobutyl, cyclopentyl or cyclohexyl), $NR^{42}R^{43}$, $C(O)NR^{44}R^{45}$, $NR^{46}C(O)R^{47}$, $SO_2NR^{48}R^{49}$, $NR^{50}SO_2R^{51}$ and $S(O)_tR^{52}$.

In an embodiment of the invention, $R^5$ represents a hydrogen atom.

Alternatively, $R^3$ and $R^4$ together with the carbon atoms to which they are attached represent a cyclopropyl ring, or $R^4$ and $R^5$ together with the carbon atom to which they are attached form a saturated or unsaturated, 3-, 4-, 5- or 6-membered carbocyclic or heterocyclic ring which ring may be optionally substituted with at least one substituent (e.g. one, two or three substituents independently) selected from halogen (e.g. fluorine, chlorine, bromine or iodine), hydroxyl, carboxyl and $C_1$-$C_6$, or $C_1$-$C_4$, or $C_1$-$C_2$ alkyl (e.g. methyl, ethyl, n-propyl, isopropyl, n-butyl, isobutyl, tert-butyl, n-pentyl or n-hexyl).

A and B each independently represent a 5- or 6- to 7-, 8-, 9- or 10-membered aromatic ring system optionally comprising at least one ring heteroatom (e.g. one, two, three or four ring heteroatoms independently selected from nitrogen, oxygen and sulphur), the ring system being optionally substituted by at least one substituent (e.g. one, two, three or four substituents independently) selected from halogen (e.g. fluorine, chlorine, bromine or iodine), carboxyl, hydroxyl, oxo (=O), nitro, cyano, mercapto (=S), $C_3$-$C_6$ cycloalkyl (cyclopropyl, cyclobutyl, cyclopentyl or cyclohexyl), $C_2$-$C_6$ or $C_2$-$C_4$ alkenyl (such as ethenyl, prop-1-enyl, prop-2-enyl, but-1-enyl, pent-1-enyl, hex-1-enyl or 2-methyl-pent-2-enyl), trifluoromethyl, $C_1$-$C_6$, or $C_1$-$C_4$, or $C_1$-$C_2$ alkoxy (e.g. methoxy, ethoxy, n-propoxy, isopropoxy, n-butoxy, isobutoxy, tert-butoxy, n-pentoxy or n-hexoxy), $C_1$-$C_6$, or $C_1$-$C_4$, or $C_1$-$C_2$ alkylcarbonyl (e.g. methylcarbonyl, ethylcarbonyl, n-propylcarbonyl, isopropylcarbonyl, n-butylcarbonyl, isobutylcarbonyl, tert-butylcarbonyl, n-pentylcarbonyl or n-hexylcarbonyl), $C_1$-$C_6$, or $C_1$-$C_4$, or $C_1$-$C_2$ alkylcarbonyloxy (e.g. methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy or n-hexylcarbonyloxy), $C_1$-$C_6$, or $C_1$-$C_4$, or $C_1$-$C_2$ alkoxycarbonyl (e.g. methoxycarbonyl, ethoxycarbonyl, n-propoxycarbonyl, isopropoxycarbonyl, n-butoxycarbonyl, isobutoxycarbonyl, tert-butoxycarbonyl, n-pentoxycarbonyl or n-hexoxycarbonyl),

—$NR^{53}R^{54}$,

—$C(O)NR^{55}R^{56}$, $NR^{57}C(O)R^{58}$, $SO_2NR^{59}R^{60}$, $SO_2NR^{59}R^{60}$, $NR^{61}SO_2R^{62}$, $S(O)_vR^{63}$, saturated 4- to 7-membered heterocyclyloxy (e.g. a nitrogen-containing heterocyclyloxy such as pyrrolidinyloxy), benzyloxy, $C_1$-$C_6$, or $C_1$-$C_4$, or $C_1$-$C_2$ alkylpiperazinyl (e.g. methylpiperazinyl) and a $C_1$-$C_6$, or $C_1$-$C_4$, or $C_1$-$C_2$ alkyl (e.g. methyl, ethyl, n-propyl, isopropyl, n-butyl, isobutyl, tert-butyl, n-pentyl or n-hexyl) group (itself optionally substituted by hydroxyl, $NR^{64}R^{65}$ phenyl or morpholinyl).

The 5- to 10-membered aromatic ring system in A or B may be carbocyclic or heterocyclic. Examples of suitable ring systems, which may be monocyclic or polycyclic (e.g. bicyclic or tricyclic) where the two or more rings (at least one of which is aromatic) are fused, include one or more of phenyl, naphthyl, benzofuranyl, benzothienyl, 1,3-benzodioxolyl, 1,4-benzodioxanyl, isoquinolinyl, quinolinyl, 1,2-dihydroquinolinyl, 1,2,3,4-tetrahydroquinolinyl, 2,3-dihydrobenzoxazinyl, 3,4-dihydrobenzoxazinyl, quinazolinyl, 1,2,3,4-tetrahydroquinazolinyl, indazolyl, naphthyridinyl (e.g. 1,8-naphthyridinyl, 2,7-naphthyridinyl), 5,6,7,8-tetrahydro-1,8-naphthyridinyl, isoindolyl, indolinyl, benzisoxazolyl, benzothiazolyl, purinyl, cinnolinyl, quinoxalinyl, 2,3-dihydrobenzofuranyl, pyrazolyl, pyrazinyl, thiazolidinyl, indanyl, thienyl, oxadiazolyl, oxazolyl, isothiazolyl, isoxazolyl, pyridazinyl, thiadiazolyl, pyrrolyl, furanyl, thiazolyl, indolyl, isoindolyl, 2,3-dihydroisoindolyl, imidazolyl, pyrimidinyl, 1,6-dihydropyrimidinyl, benzimidazolyl, triazolyl, tetrazolyl, pyridinyl, oxazolidinyl, imidazolidinyl, azaindolyl, thieno[2,3-b]pyridinyl, thieno[2,3-b]pyrazinyl, thieno[2,3-b]quinolinyl, benzoxazolyl, benzoxazolinyl and benzothiazolinyl.

Preferred 5- to 10-membered aromatic ring systems include phenyl, pyrazolyl, pyridinyl, indolyl, oxazolyl, quinolinyl, pyrimidinyl, thienyl, 2,3-dihydrobenzoxazinyl, 3,4-dihydrobenzoxazinyl, benzothiazinyl, benzoxazolinyl and benzothiazolinyl.

In an embodiment of the invention, A represents a phenyl ring.

In an embodiment of the invention, B represents a 5- to 10-membered aromatic ring system optionally comprising one or two ring heteroatoms independently selected from nitrogen, oxygen and sulphur, the ring system being optionally substituted by at least one substituent (e.g. one, two, three or four substituents independently) selected from halogen, carboxyl, hydroxyl, cyano, $C_1$-$C_6$, or $C_1$-$C_4$, or $C_1$-$C_2$ alkoxy (e.g. methoxy, ethoxy, n-propoxy, isopropoxy, n-butoxy, isobutoxy, tert-butoxy, n-pentoxy or n-hexoxy), —$NR^{53}R^{54}$, —$C(O)NR^{55}R^{56}$, $NR^{57}C(O)R^{58}$, $SO_2NR^{59}R^{60}S(O)_vR^{63}$, pyrrolidinyloxy, benzyloxy, methylpiperazinyl and a $C_1$-$C_6$, or $C_1$-$C_4$, or $C_1$-$C_2$ alkyl (e.g. methyl, ethyl, n-propyl, isopropyl, n-butyl, isobutyl, tert-butyl, n-pentyl or n-hexyl) group (itself optionally substituted by hydroxyl, $C_1$-$C_6$ alkoxy, $NR^{64}R^{65}$, phenyl or morpholinyl).

In a further embodiment of the invention, B represents a 5- to 10-membered aromatic ring system optionally comprising one or two ring heteroatoms independently selected from nitrogen, oxygen and sulphur, the ring system being optionally substituted by one, two or three substituents independently selected from fluorine, chlorine, carboxyl, hydroxyl, cyano, $C_1$-$C_3$ alkoxy (e.g. methoxy or n-propoxy), —$NR^{53}R^{54}$ (e.g. $N(CH_3)_2$), —$C(O)NR^{55}R^{56}$ (e.g. $C(O)NH_2$ or $C(O)N(CH_3)_2$), $NR^{57}C(O)R^{58}$ (e.g. $NHC(O)CH_3$), $SO_2NR^{59}R^{60}$ (e.g. $SO_2N(CH_3)_2$), $S(O)_vR^{63}$ (e.g. $SCH_3$ or $SO_2C_2H_5$), pyrrolidinyloxy, benzyloxy, methylpiperazinyl and $C_1$-$C_3$ alkyl (e.g. methyl, ethyl, or n-propyl), the alkyl substituent group itself being optionally substituted by hydroxyl, methoxy, $NR^{64}R^{65}$ (e.g. $NH_2$ or piperidine), phenyl or morpholinyl.

In a still further embodiment B represents phenyl, pyrazolyl, pyridinyl, indolyl, oxazolyl, quinolinyl, pyrimidinyl, thienyl, 2,3-dihydrobenzoxazinyl, 3,4-dihydrobenzoxazinyl, benzoxazolinyl and benzothiazolinyl each of which may be optionally substituted by one, two or three substituents independently selected from fluorine, chlorine, carboxyl, hydroxyl, cyano, $C_1$-$C_3$ alkoxy (e.g. methoxy or n-propoxy), —$NR^{53}R^{54}$ (e.g. $N(CH_3)_2$), —$C(O)NR^{55}R^{56}$ (e.g. $C(O)NH_2$ or $C(O)N(CH_3)_2$), $NR^{57}C(O)R^{58}$ (e.g. $NHC(O)CH_3$), $SO_2NR^{59}R^{60}$ (e.g. $SO_2N(CH_3)_2$), $S(O)_vR^{63}$ (e.g. $SCH_3$ or $SO_2C_2H_5$), pyrrolidinyloxy, benzyloxy, methylpiperazinyl and $C_1$-$C_3$ alkyl (e.g. methyl or n-propyl), the alkyl substituent group itself being optionally substituted by hydroxyl, $NR^{64}R^{65}$ (e.g. $NH_2$ or piperidine), phenyl or morpholinyl.

In an embodiment of the invention, $X^2$ represents a bond,

In an embodiment of the invention, n represents 0, 1 or 2;

$X^1$ represents a methylene group;

y represents 0 or 1;

$R^1$ represents hydroxyl;

$R^2$ represents a hydrogen atom;

$R^3$ represents a hydrogen atom;

$R^4$ represents a hydrogen atom;

$R^5$ represents a hydrogen atom;

A represents phenyl;

B represents a 5- to 10-membered aromatic ring system optionally comprising one or two ring heteroatoms independently selected from nitrogen, oxygen and sulphur, the ring system being optionally substituted by one, two or three substituents independently selected from fluorine, chlorine, carboxyl, hydroxyl, cyano, $C_1$-$C_3$ alkoxy, $N(CH_3)_2$, $C(O)NH_2$, $C(O)N(CH_3)_2$, $NHC(O)CH_3$, $SO_2N(CH_3)_2$, $SCH_3$, $SO_2C_2H_5$, pyrrolidinyloxy, benzyloxy, methylpiperazinyl and $C_1$-$C_3$ alkyl (itself optionally substituted by hydroxyl, methoxy, $NH_2$, piperidine, phenyl or morpholinyl); and $X^2$ represents a bond.

Examples of compounds of the invention include (S)-N-((S)-2-(3'-Chlorobiphenyl-4-yl)-1-cyanoethyl)piperidine-2-carboxamide, (S)-N-((S)-1-Cyano-2-(3'-(piperidin-1-ylmethyl)biphenyl-4-yl)ethyl)piperidine-2-carboxamide, (S)-N-((S)-2-(biphenyl-4-yl)-1-cyanoethyl)pyrrolidine-2-carboxamide, (S)-N-((S)-2-(4-(1-Benzyl-1H-pyrazol-4-yl)phenyl)-1-cyanoethyl)-piperidine-2-carboxamide,
(S)-N-((S)-2-(4'-Carbamoylbiphenyl-4-yl)-1-cyanoethyl)piperidine-2-carboxamide,
(S)-N-((S)-1-Cyano-2-(3'-cyanobiphenyl-4-yl)ethyl)piperidine-2-carboxamide,
(S)-N-((S)-2-(3'-(Aminomethyl)biphenyl-4-yl)-1-cyanoethyl)piperidine-2-carboxamide,
(S)-N-((S)-2-(3'-Acetamidobiphenyl-4-yl)-1-cyanoethyl)piperidine-2-carboxamide,
(S)-N-((S)-1-Cyano-2-(4'-(morpholinomethyl)biphenyl-4-yl)ethyl)piperidine-2-carboxamide,
(S)-N-((S)-1-Cyano-2-(4-(pyridin-3-yl)phenyl)ethyl)piperidine-2-carboxamide,
(S)-N-((S)-1-Cyano-2-(4'-hydroxy-2'-methylbiphenyl-4-yl)ethyl)piperidine-2-carboxamide,
4'-((S)-2-Cyano-2-((S)-piperidine-2-carboxamido)ethyl)biphenyl-3-carboxylic acid,
(S)-N-((S)-1-Cyano-2-(2'-((R)-pyrrolidin-3-yloxy)biphenyl-4-yl)ethyl)piperidine-2-carboxamide,
(S)-N-((S)-2-(4-(1H-Indol-2-yl)phenyl)-1-cyanoethyl)piperidine-2-carboxamide,
(2S)-N-[(1S)-1-cyano-2-(3'-methoxybiphenyl-4-yl)ethyl]piperidine-2-carboxamide,
Piperidine-2-carboxylic acid (2-biphenyl-4-yl-1-cyanoethyl)-amide,
(2S,4R)-N-((S)-2-(biphenyl-4-yl)-1-cyanoethyl)-4-hydroxypyrrolidine-2-carboxamide,
(R)-N-((S)-2-(biphenyl-4-yl)-1-cyanoethyl)thiazolidine-4-carboxamide,
(S)-N-((S)-1-cyano-2-(3'-cyanobiphenyl-4-yl)ethyl)azetidine-2-carboxamide,
(2S)-N-[(1S)-1-Cyano-2-[4-[4-(dimethylsulfamoyl)phenyl]phenyl]ethyl]piperidine-2-carboxamide,
(2S)-N-[(1S)-1-Cyano-2-(4-1,2-oxazol-4-ylphenyl)ethyl]piperidine-2-carboxamide,
(2S)-N-[(1S)-1-Cyano-2-[4-(3-methylsulfanylphenyl)phenyl]ethyl]piperidine-2-carboxamide,
(2S)-N-[(1S)-1-Cyano-2-[4-(4-hydroxyphenyl)phenyl]ethyl]piperidine-2-carboxamide,
(2S)-N-[(1S)-1-Cyano-2-[4-(4-cyanophenyl)phenyl]ethyl]piperidine-2-carboxamide,
(2S)-N-[(1S)-1-Cyano-2-[4-(4-methoxyphenyl)phenyl]ethyl]piperidine-2-carboxamide,
(2S)-N-[(1S)-1-Cyano-2-[4-(1-methylpyrazol-4-yl)phenyl]ethyl]piperidine-2-carboxamide,
(2S)-N-[(1S)-1-Cyano-2-[4-[4-(3-hydroxypropyl)phenyl]phenyl]ethyl]piperidine-2-carboxamide,
(2S)-N-[(1S)-2-(4-Benzo[1,3]dioxol-5-yl)phenyl)-1-cyanoethyl]piperidine-2-carboxamide,
(2S)-N-[(1S)-1-Cyano-2-[4-(3,4-difluorophenyl)phenyl]ethyl]piperidine-2-carboxamide,
(2S)-N-[(1S)-1-Cyano-2-[4-(4-fluoro-2-phenylmethoxyphenyl)phenyl]ethyl]piperidine-2-carboxamide,
(2S)-N-[(1S)-1-Cyano-2-[4-(3-fluoro-4-methoxy-phenyl)phenyl]ethyl]piperidine-2-carboxamide,
(2S)-N-[(1S)-1-Cyano-2-[4-(3,4-dimethoxyphenyl)phenyl]ethyl]piperidine-2-carboxamide,
(2S)-N-[(1S)-1-Cyano-2-[4-(2,4-dimethoxyphenyl)phenyl]ethyl]piperidine-2-carboxamide,
(2S)-N-[(1S)-2-[4-(3-Carbamoylphenyl)phenyl]-1-cyanoethyl]piperidine-2-carboxamide,
(2S)-N-[(1S)-1-Cyano-2-[4-(2,5-dioxabicyclo[4.4.0]deca-7,9,11-trien-8-yl)phenyl]ethyl]piperidine-2-carboxamide,
(2S)-N-[(1S)-2-[4-[4-(Aminomethyl)phenyl]phenyl]-1-cyano-ethyl]piperidine-2-carboxamide,
(2S)-N-[(1S)-1-Cyano-2-[4-(2-dimethylaminopyrimidin-5-yl)phenyl]ethyl]piperidine-2-carboxamide,
(2S)-N-[(1S)-1-Cyano-2-[4-(4-methylthiophen-3-yl)phenyl]ethyl]piperidine-2-carboxamide,
(2S)-N-[(1S)-1-Cyano-2-[4-(3-fluoro-4-propoxy-phenyl)phenyl]ethyl]piperidine-2-carboxamide,
(2S)-N-[(1S)-1-Cyano-2-[4-(2-methoxypyridin-3-yl)phenyl]ethyl]piperidine-2-carboxamide,
(2S)-N-[(1S)-1-Cyano-2-[4-(2-methylpyrazol-3-yl)phenyl]ethyl]piperidine-2-carboxamide,
(2S)-N-[(1S)-1-Cyano-2-[4-[3-(dimethylcarbamoyl)phenyl]phenyl]ethyl]piperidine-2-carboxamide,
(2S)-N-[(1S)-1-Cyano-2-[4-(4-ethylsulfonyl-2-methyl-phenyl)phenyl]ethyl]piperidine-2-carboxamide,
(2S)-N-[(1S)-1-Cyano-2-[4-(3,5-difluoro-2-methoxy-phenyl)phenyl]ethyl]piperidine-2-carboxamide,
(2S)-N-[(1S)-1-Cyano-2-[4-[3-(hydroxymethyl)phenyl]phenyl]ethyl]piperidine-2-carboxamide,
(2S)-N-[(1S)-1-Cyano-2-[4-(2-methoxypyrimidin-5-yl)phenyl]ethyl]piperidine-2-carboxamide,
(2S)-N-[(1S)-1-Cyano-2-[4-[6-(4-methylpiperazin-1-yl)pyridin-3-yl]phenyl]ethyl]piperidine-2-carboxamide,
(2S)-N-[(1S)-1-Cyano-2-[4-(2-hydroxyphenyl)phenyl]ethyl]piperidine-2-carboxamide,
(2S)-N-[(1S)-1-Cyano-2-[4-(quinolin-8-yl)phenyl)ethyl]piperidine-2-carboxamide,
(2S)-N-[(1S)-1-Cyano-2-[4-(2-methylphenyl)phenyl]ethyl]piperidine-2-carboxamide,
(2S)-N-[(1S)-1-Cyano-2-[4-(2-phenylmethoxyphenyl)phenyl]ethyl]piperidine-2-carboxamide,
(2S)-N-[(1S)-1-Cyano-2-[4-(2-methylpyridin-3-yl)phenyl]ethyl]piperidine-2-carboxamide,
(S)-N-((S)-1-Cyano-2-(4-(6-cyanopyridin-3-yl)phenyl)ethyl)piperidine-2-carboxamide,
(S)-N-((S)-1-Cyano-2-(4-(3-(2-hydroxyethyl)-2-oxo-2,3-dihydrobenzo[d]thiazol-5-yl)phenyl)ethyl)piperidine-2-carboxamide,
(S)-N-((S)-1-cyano-2-(4-(3-(2-methoxyethyl)-2-oxo-2,3-dihydrobenzo[d]thiazol-5-yl)phenyl)ethyl)piperidine-2-carboxamide,
(S)-N-((S)-1-Cyano-2-(4'-cyano-3'-fluorobiphenyl-4-yl)ethyl)piperidine-2-carboxamide,
(S)-N-((S)-1-Cyano-2-(4'-cyano-3'-(methylthio)biphenyl-4-yl)ethyl)-piperidine-2-carboxamide,
(S)-N-((S)-1-Cyano-2-(4'-cyano-3'-(methylsulfonyl)biphenyl-4-yl)ethyl)piperidine-2-carboxamide,
(S)-N-((S)-1-Cyano-2-(4'-cyano-3'-(ethylsulfonyl)biphenyl-4-yl)ethyl)piperidine-2-carboxamide,
(S)-N-((S)-1-Cyano-2-(4'-cyano-3'-(propylsulfonyl)biphenyl-4-yl)ethyl)piperidine-2-carboxamide,
(2S)-N-((1S)-2-(4'-Carbamoyl-3'-(methylsulfinyl)biphenyl-4-yl)-1-cyanoethyl)piperidine-2-carboxamide,
(2S)-N-((1S)-1-Cyano-2-(4'-cyano-3'-(2-methyl-1H-imidazol-1-yl)biphenyl-4-yl)ethyl)piperidine-2-carboxamide,
(S)-N-((S)-1-cyano-2-(3'-cyano-4'-(methylthio)biphenyl-4-yl)ethyl)piperidine-2-carboxamide,
(S)-N-((S)-1-Cyano-2-(3'-cyano-4'-(methylsulfonyl)biphenyl-4-yl)ethyl)piperidine-2-carboxamide,
(S)-tert-Butyl 2-((S)-cyano-2-(3'-cyano-4'-(propylsulfonyl)biphenyl-4-yl)ethylcarbamoyl)piperidine-1-carboxylate,
(S)-N-((S)-1-Cyano-2-(4-(3-methyl-2-oxo-2,3-dihydrobenzo[d]thiazol-5-yl)phenyl)ethyl)piperidine-2-carboxamide,
(2S)-N-{(1S)-1-Cyano-2-[4-(1,1-dioxido-2,3-dihydro-1,2-benzisothiazol-5-yl)phenyl]ethyl}piperidine-2-carboxamide, (S)-N-((S)-1-Cyano-2-(4-(3-oxo-3,4-dihydro-2H-benzo[b][1,4]thiazin-7-yl)phenyl)ethyl)piperidine-2-carboxamide,
(2S)-N-{(1S)-1-Cyano-2-[4-(2-methyl-1,1-dioxido-2,3-dihydro-1,2-benzisothiazol-5-yl)phenyl]ethyl}piperidine-2-carboxamide,
(S)-N-((S)-1-Cyano-2-(4'-ethylbiphenyl-4-yl)ethyl)piperidine-2-carboxamide trifluoroacetate,
(S)-N-((S)-1-Cyano-2-(4'-(N-methylsulfamoyl)biphenyl-4-yl)ethyl)piperidine-2-carboxamide trifluoroacetate,
(S)-N-((S)-2-(4'-(Azetidin-1-ylsulfonyl)biphenyl-4-yl)-1-cyanoethyl)piperidine-2-carboxamide trifluoroacetate,
(S)-N-((S)-1-Cyano-2-(4'-(N-(2-hydroxyethyl)sulfamoyl)biphenyl-4-yl)ethyl)piperidine-2-carboxamide,
(S)-N-((S)-1-Cyano-2-(4'-(methylcarbamoyl)biphenyl-4-yl)ethyl)piperidine-2-carboxamide trifluoroacetate,
(S)-N-((S)-1-Cyano-2-(4'-(pyrrolidine-1-carbonyl)biphenyl-4-yl)ethyl)piperidine-2-carboxamide trifluoroacetate,
(S)-N-((S)-1-Cyano-2-(4'-(4-methylpiperazine-1-carbonyl)biphenyl-4-yl)ethyl)piperidine-2-carboxamide trifluoroacetate,
(S)-N-((S)-1-Cyano-2-(6-(4-cyanophenyl)pyridin-3-yl)ethyl)piperidine-2-carboxamide trifluoroacetate,
(S)-N-((S)-1-Cyano-2-(6-(3-cyanophenyl)pyridin-3-yl)ethyl)piperidine-2-carboxamide trifluoroacetate,
(S)-N-((S)-1-Cyano-2-(6-(2-hydroxyphenyl)pyridin-3-yl)ethyl)piperidine-2-carboxamide,
(S)-N-((S)-1-Cyano-2-(6-(4-(N,N-dimethylsulfamoyl)phenyl)pyridin-3-yl)ethyl)piperidine-2-carboxamide trifluoroacetate,
(S)-N-((S)-2-(6-(3-Chloro-5-(dimethylcarbamoyl)phenyl)pyridin-3-yl)-1-cyanoethyl)piperidine-2-carboxamide trifluoroacetate,
(S)-N-((S)-1-Cyano-2-(4'-(trifluoromethyl)biphenyl-4-yl)ethyl)piperidine-2-carboxamide trifluoroacetate,
(S)-N-((S)-1-Cyano-2-(3'-(piperidine-1-carbonyl)biphenyl-4-yl)ethyl)piperidine-2-carboxamide trifluoroacetate,
(S)-N-((S)-1-Cyano-2-(3'-(thiazol-2-ylcarbamoyl)biphenyl-4-yl)ethyl)piperidine-2-carboxamide trifluoroacetate,
(S)-N-((S)-1-Cyano-2-(3'-(2-cyanoethylcarbamoyl)biphenyl-4-yl)ethyl)piperidine-2-carboxamide,
(S)-N-((S)-2-(3'-(2-amino-2-oxoethyl)biphenyl-4-yl)-1-cyanoethyl)piperidine-2-carboxamide trifluoroacetate,
(S)-N-((S)-1-Cyano-2-(3'-(N,N-dimethylsulfamoyl)biphenyl-4-yl)ethyl)piperidine-2-carboxamide trifluoroacetate,
(S)-N-((S)-1-Cyano-2-(3'-(pyrrolidin-1-ylsulfonyl)biphenyl-4-yl)ethyl)piperidine-2-carboxamide trifluoroacetate,
(S)-N-((S)-1-Cyano-2-(3'-(methylsulfonamidomethyl)biphenyl-4-yl)ethyl)piperidine-2-carboxamide trifluoroacetate,
(S)-N-((S)-2-(3'-(Acetamidomethyl)biphenyl-4-yl)-1-cyanoethyl)-piperidine-2-carboxamide trifluoroacetate,
(S)-N-((S)-1-Cyano-2-(4'-(4-cyanopiperidin-1-ylsulfonyl)biphenyl-4-yl)ethyl)piperidine-2-carboxamide trifluoroacetate,
(S)-N-((S)-1-Cyano-2-(4'-(morpholinosulfonyl)biphenyl-4-yl)ethyl)piperidine-2-carboxamide trifluoroacetate,
(S)-N-((S)-1-Cyano-2-(4'-(4-methylpiperazin-1-ylsulfonyl)biphenyl-4-yl)ethyl)piperidine-2-carboxamide trifluoroacetate,
(S)-N-((S)-1-Cyano-2-(4-(3-methyl-2-oxo-2,3-dihydrobenzo[d]oxazol-5-yl)phenyl)ethyl)piperidine-2-carboxamide,
(S)-N-((S)-1-Cyano-2-(4-(3-(2-methoxyethyl)-2-oxo-2,3-dihydrobenzo[d]-oxazol-5-yl)phenyl)ethyl)piperidine-2-carboxamide,
(S)-N-((S)-1-Cyano-2-(4-(3-methyl-2-oxo-2,3-dihydrobenzo[d]thiazol-6-yl)phenyl)ethyl)piperidine-2-carboxamide,
(S)-N-((S)-1-Cyano-2-(4-(3-(2-hydroxyethyl)-2-oxo-2,3-dihydrobenzo[d]thiazol-6-yl)phenyl)ethyl)piperidine-2-carboxamide,
(S)-N-((S)-1-Cyano-2-(4'-cyanobiphenyl-3-yl)ethyl)piperidine-2-carboxamide trifluoroacetate,
(S)-N-((S)-1-Cyano-2-(4'-(cyanomethyl)-3'-(methylsulfonyl)biphenyl-4-yl)ethyl)-piperidine-2-carboxamide trifluoroacetate,
(S)-N-((S)-1-Cyano-2-(4-(phenylsulfonyl)phenyl)ethyl)piperidine-2-carboxamide,
(S)-N-((1R,2R)-1-Cyano-2-(4'-cyanobiphenyl-4-yl)cyclopropyl)piperidine-2-carboxamide trifluoroacetate,
(S)-N-((1R,2R)-2-(4'-(Azetidin-1-ylsulfonyl)biphenyl-4-yl)-1-cyanocyclopropyl)piperidine-2-carboxamide trifluoroacetate,
(S)-N-((S)-1-Cyano-2-(4'-(trifluoromethoxy)biphenyl-4-yl)ethyl)piperidine-2-carboxamide,
(S)-N-((S)-1-Cyano-2-(4'-(methylsulfonyl)biphenyl-4-yl)ethyl)piperidine-2-carboxamide,
((2S)-N-(1-Cyano-2-(4'-(4-ethylpiperazin-1-ylsulfonyl)biphenyl-4-yl)ethyl)piperidine-2-carboxamide ditrifluoroacetate,
(2S)-N-(1-Cyano-2-(4'-(4-methyl-1,4-diazepan-1-ylsulfonyl)biphenyl-4-yl)ethyl)piperidine-2-carboxamide ditrifluoroacetate,
(S)-N-((S)-1-Cyano-2-(3'-(morpholinomethyl)biphenyl-4-yl)ethyl)piperidine-2-carboxamide ditrifluoroacetate, or
(S)-N-((S)-1-Cyano-2-(4-(1,2,3,4-tetrahydroisoquinolin-6-yl)phenyl)ethyl)piperidine-2-carboxamide ditrifluoroacetate and pharmaceutically acceptable salts of any one thereof.

It should be noted that each of the chemical compounds listed above represents a particular and independent aspect of the invention.

The present invention further provides a process for the preparation of a compound of formula (I) or a pharmaceutically acceptable salt thereof as defined above which comprises reacting a compound of formula (II)

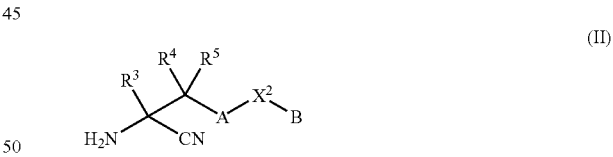

wherein $R^3$, $R^4$, $R^5$, A, $X^2$ and B are as defined in formula (I), with a compound of formula (III)

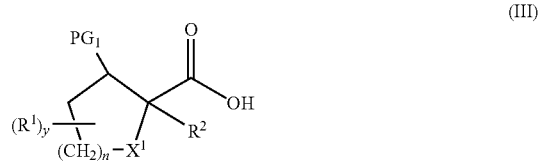

wherein $PG_1$ represents a protecting group and n, $X^1$, y, $R^1$ and $R^2$ are as defined in formula (I), and optionally thereafter carrying out one or more of the following procedures:

converting a compound of formula (I) into another compound of formula (I)

removing any protecting groups forming a pharmaceutically acceptable salt.

The process of the invention is conveniently carried out in the presence of a base such as diisopropylethylamine or triethylamine and an activating agent such as a "uronium" reagent (for example, 2-(1-H-benzotriazole-1-yl)-1,1,3,3-tetramethyluronium tetrafluoroborate) or a dehydrating agent (for example, propane phosphonic acid anhydride). The reaction is conveniently carried out in an organic solvent such as N,N-dimethylformamide or tetrahydrofuran at a temperature, for example, in the range from 20° C. to 100° C., in particular at ambient temperature (25° C.).

Compounds of formula (II) may be prepared by contacting a compound of formula (IV)

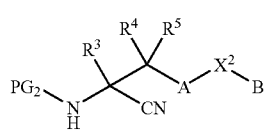

(IV)

wherein $PG_2$ represents a protecting group (e.g. tert-butoxycarbonyl) and $R^3$, $R^4$, $R^5$, A, $X^2$ and B are as defined in formula (II), with a suitable reagent to remove the protecting group $PG_2$. An example of a suitable reagent is formic acid.

Compounds of formula (IV) in which A and B both represent a phenyl group and $X^2$ represents a bond may be prepared by reacting a compound of formula (V)

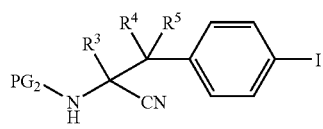

(V)

wherein $PG_2$, $R^3$, $R^4$ and $R^5$ are as defined in formula (IV), with a compound of formula (VI) or an ester thereof

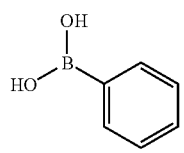

(VI)

in the presence of a catalyst such as bis[bis(1,2-diphenylphosphino)ethane]palladium (0) and a base such as potassium carbonate. The reaction is conveniently carried out in a solvent such as dioxane/water mixture at a temperature, for example, in the range from 20° C. to 100° C., particularly at 75° C.

Compounds of formula (V) may be prepared from a compound of formula (VII)

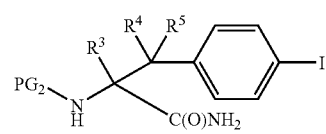

(VII)

in which $PG_2$, $R^3$, $R^4$ and $R^5$ are as defined in formula (V), using standard literature procedures for the dehydration of an amide, for example with (methoxycarbonylsulfamoyl)triethyl ammonium hydroxide, which can be prepared in situ with triethylamine and methyl chlorosulfonylcarbamate, in a solvent such as DCM at a temperature in the range from –20° C. to 25° C., for example at 0° C.

Compounds of formula (VII) may be prepared by reacting a compound of formula (VIII)

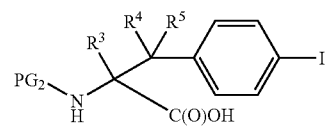

(VIII)

in which $PG_2$, $R^3$, $R^4$ and $R^5$ are as defined in formula (VII), with an aqueous ammonia solution, using standard literature procedures for the formation of an amide, for example, in the presence of a base such as N-ethyl-morpholine and an activating agent such as a "uronium" reagent (for example, 2-(1-H-benzotriazole-1-yl)-1,1,3,3-tetramethyluronium tetrafluoroborate). The reaction is conveniently carried out in an organic solvent such as N,N-dimethylformamide, at a temperature in the range from –20° C. to 100° C., for example at 0° C.

Compounds of formula (VIII) are either commercially available, are known in the literature (e.g. from *Tetrahedron: Asymmetry*, 1998, 9, 503) or may be prepared using known techniques.

Other compounds of formula (IV) in which one or both of A and B represent a heteroaryl group and $X^2$ represents a bond may be prepared by reacting a compound of formula (X)

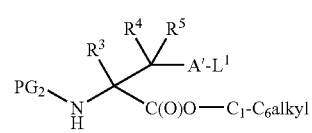

(X)

in which $PG_2$, $R^3$, $R^4$ and $R^5$ are as defined in formula (IV), A' represents an aryl or heteroaryl group and $L^1$ represents a leaving group such as halogen, with a compound of formula (VI) or formula (XI), B'—B(OH)$_2$, in which B' represents a heteroaryl group to form a compound of formula (XII)

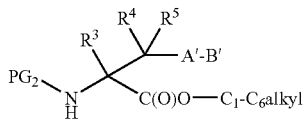

(XII)

in which PG$_2$, R$^3$, R$^4$, R$^5$, A' and B' are as defined above. Compounds of formula (XII) can then be converted to compounds of formula (IV) by processes known in the art, for example, as described in *Bioorg. Med. Chem. Lett.* 2002, 12, 3059 or Published US Patent Application No. 2007/0099835.

The present invention further provides a process for the preparation of a compound of formula (I) or a pharmaceutically acceptable salt thereof as defined above which comprises reacting a compound of formula (XIII)

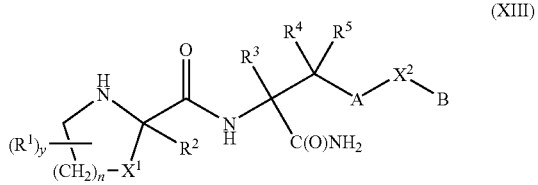

(XIII)

wherein A, B, X$^1$, y, n, R$^1$, R$^2$, R$^3$, R$^4$ and R$^5$ are as defined above, using standard literature procedures for the dehydration of an amide, for example with (methoxycarbonylsulfamoyl)tri-ethyl ammonium hydroxide, which can be prepared in situ with triethylamine and methyl chlorosulfonylcarbamate, in a solvent such as DCM at a temperature in the range from −20° C. to 25° C., for example at 0° C.

A compound of formula (XIII) in which X$^2$ represents a bond may be prepared by reacting a compound of formula (XIV)

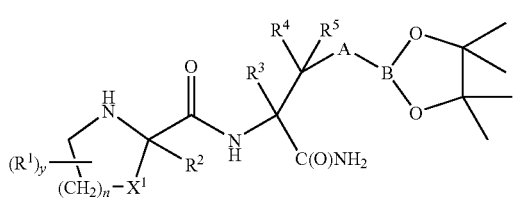

(XIV)

with a halide of formula (XV) in which B is defined as in formula (I)

B—Br/I        (XV)

in the presence of a catalyst such as bis[bis(1,2-diphenylphosphino)ethane]palladium (0) and a base such as potassium carbonate. The reaction is conveniently carried out in a solvent such as dioxane/water mixture at a temperature, for example, in the range from 20° C. to 100° C., particularly at 75° C.

A compound of formula (XIV) may be prepared by reacting a compound of formula (XVI) with 4,4,4',4',5,5,5',5'-octamethyl-2,2'-bi(1,3,2-dioxaborolane) in the presence of a suitable catalyst such as 1,1'-bis(diphenylphosphino)ferrocene-palladium(II) dichloride DCM complex and 1,1'-bis(diphenylphosphino)ferrocene, with a suitable base such as potassium acetate, in a solvent such as dimethylsulfoxide at a temperature in the range 60° C. to 100° C., for example at 80° C.

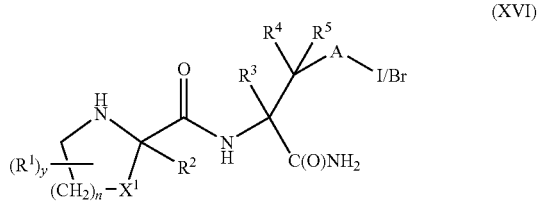

(XVI)

A compound of formula (XVI) may be prepared by reacting a compound of formula (XVII)

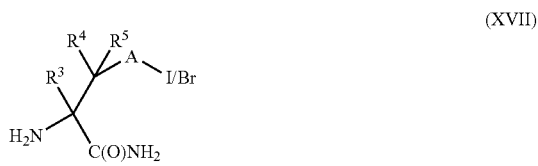

(XVII)

with a compound of formula (III)

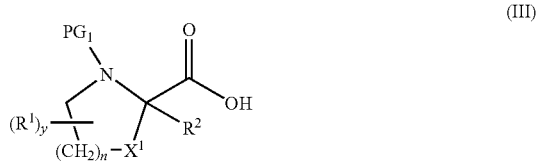

(III)

in the presence of a base such as diisopropylethylamine or triethylamine and a dehydrating agent (for example, propane phosphonic acid anhydride). The reaction is conveniently carried out in an organic solvent such as N,N-dimethylformamide or tetrahydrofuran at a temperature, for example, in the range from 20° C. to 100° C., in particular at ambient temperature (25° C.).

Compounds of formula (XVII) may be prepared by reacting a compound of formula (XVIII)

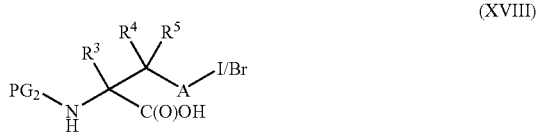

(XVIII)

in which PG$_2$, R$^3$, R$^4$ and R$^5$ are as defined in formula (VII), with an aqueous ammonia solution, using standard literature procedures for the formation of an amide, for example, in the presence of a base such as N-ethyl-morpholine and an activating agent such as a "uronium" reagent (for example, 2-(1-H-benzotriazole-1-yl)-1,1,3,3-tetramethyluronium tetrafluoroborate). The reaction is conveniently carried out in an organic solvent such as N,N-dimethylformamide, at a temperature in the range from −20° C. to 100° C., for example at 0° C.

Compounds of formula (VIII) are either commercially available, are known in the literature (e.g. from *Tetrahedron: Asymmetry*, 1998, 9, 503) or may be prepared using known techniques.

Compounds of formula (IV) in which $X^2$ represents oxygen, sulphur or $NR^{66}$ may be prepared as described in the following reaction scheme 1 in which $PG_2$, $R^3$, $R^4$, $R^5$, A and B are as defined in formula (IV), $X^{2'}$ represents oxygen, sulphur or $NR^{66}$, Y represents O-alkyl (e.g. O-t-butyl), OH or $NH_2$ and $L^2$ represents a leaving group (e.g. halogen):

Compounds of formula (IV) can be obtained from those of formula (XX) (step (ii), Reaction Scheme 1) using methods outlined above for the formation of compounds of formula (V). In turn, compounds of formula (XX) can be obtained from those of formula (XIX) by displacement under thermal conditions, if necessary, with a catalyst such as palladium(0) with the appropriate alcohol, amine or thiol (step (i), Reaction Scheme 1). For $X^2$=O, N or S, examples of such transformations are known in the literature and are described in *Org. Lett.* 2002, 4, 2885; *J. Am. Chem. Soc* 1999, 121, 4369; *Curr. Org. Chem.* 2004, 8, 1235; *J. Med. Chem.* 2005, 48, 4254 and references therein. Alternatively, compounds of formula (XX), where $X^2$ represents O or N, can be prepared from compounds of formula (XIX), where $L^2$ represents OH or $NH_2$, with the corresponding boronic acids of formula (VI) or (XI). Examples of this transformation are also known in the literature (*Bioorg. Med. Chem. Lett.* 2006, 16, 6316; *J. Org. Chem.* 2007, 72, 666). Compounds of formula (IV) in which $X^2$ represents SO or $SO_2$ may be prepared from the corresponding thioether compound of formula (IV) in which $X^2$ represents sulphur by oxidation with a suitable oxidising agent such as Oxone®.

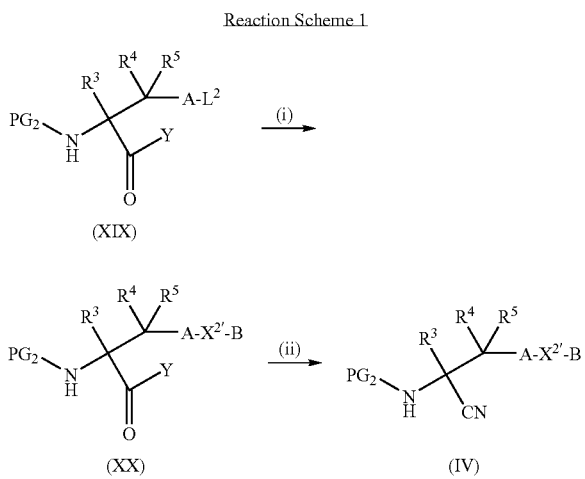

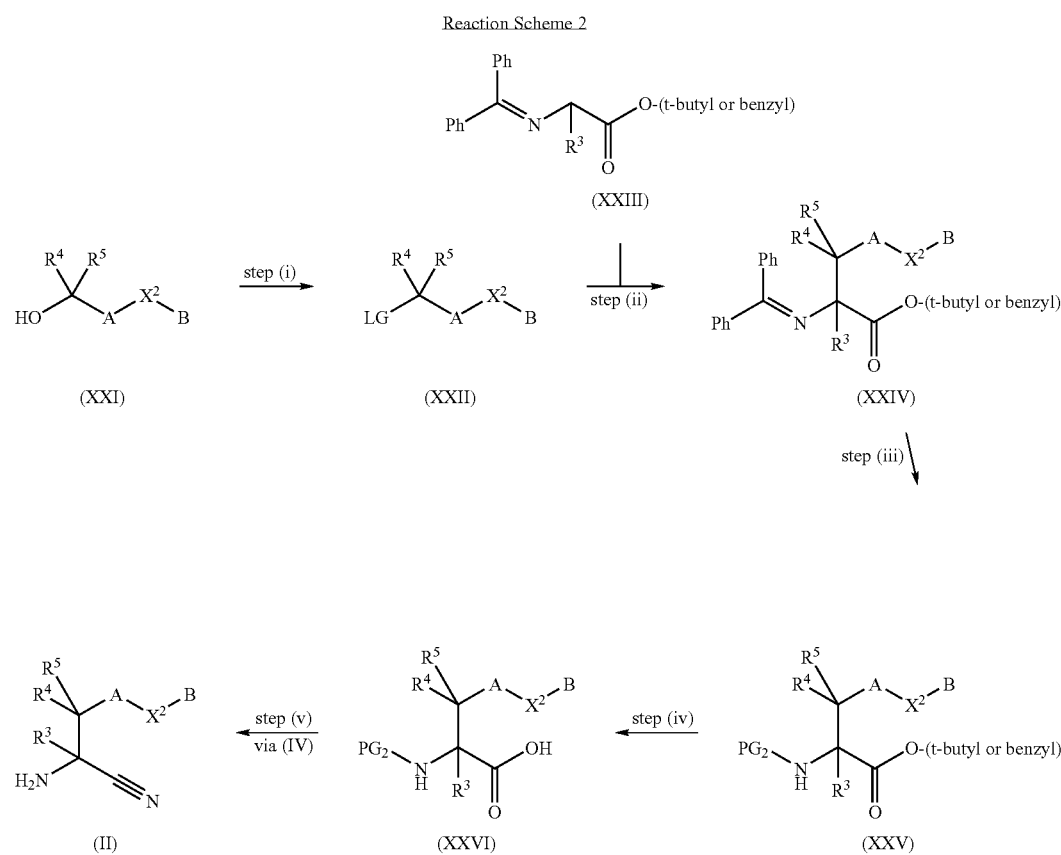

Compounds of formula (II) in which $X^2$ is $C(O)NR^{66}$, $NR^{66}C(O)$, $S_2NR^{66}$, $NR^{66}SO_2$, $C_1$-$C_3$ alkyl, ethenyl, or ethynyl may be prepared via alternative methodology shown in Reaction Scheme 2. Compounds of formula (II) can be formed from those of formula (XXVI) (step (v)) using methods outlined above for the formation of compounds of formula (v). Compounds of formula (XXVI) can be accessed (step (iv)) from deprotection of the ester group in the compound of formula (XXV) with lithium hydroxide in aqueous THF.

Compounds of formula (XXV) can be accessed from compounds of formula (XXIV) by a protecting group exchange via deprotection of the diphenylmethylene imine group with aqueous citric acid, followed by protection with a group such as tert-butoxycarbonyl. Compounds of formula (XXIV) can be accessed with methodology utilising asymmetric phase-transfer catalytic alkylation of a glycine imine of formula (XXIII) with an electrophile of formula (XXII), for example, as described in *Synlett* 2004, 326. The electrophilic compounds of formula (XXII), where LG is for example p-toluenesulfonate, methanesulfonate or halide (for example bromide) can be accessed from activation of the alcohol moiety in a compound formula (XXI), for example by methods according to Houben-Weyl, Methoder Organischen Chemie, Alkohole III, 6/1b, Thieme-Verlag 1984, $4^{th}$ Ed., pp. 927-939; Comprehensive Organic Transformations. A guide to functional group preparations, VCH Publishers 1989, $1^{st}$ Ed., pp. 353-363 and *J. Org. Chem.* 1971, 36, 3044-45. Compounds of formula (XXI) in which $X^2$ is $CONR^{66}$ (e.g. *Tetrahedron Lett.* 2002, 43, 7221), $NR^{66}CO$ (e.g. *Tetrahedron Lett.* 2005, 46, 8401), $SO_2NR^{66}$ (e.g. WO2006038594(A1)), $NR^{66}SO_2$ (e.g. *Bioorganic Med. Chem.* 2007, 15, 2156, *Bioorganic Med. Chem.* 1998, 6, 15), $C_1$-$C_3$ alkyl (e.g. *J. Org. Chem.* 2001, 66, 2874; *Chem. Commun.* 2004, 3, 316; US 2007/0066820(A1); WO 2006/057870(A1); *J. Org. Chem.* 1984, 49, 1607), ethenyl (e.g. *J. Org. Chem.* 2005, 70, 6066, *Chem. Commun.* 2004, 3, 316); or ethynyl (e.g. WO 2007/071766(A2,A3)) are known in the literature where their preparations are described.

Compounds of formula (IV) in which $R^3$ and $R^4$ together with the carbon atoms to which they are attached represent a cyclopropyl ring are known, for example, from WO 2007/012180.

Compounds of formulae (VI), (X) and (XI) are either commercially available, are known in the literature or may be prepared using known techniques.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a hydrochloride, hydrobromide, trifluoroacetate, sulphate, phosphate, acetate, fumarate, maleate, tartrate, lactate, citrate, pyruvate, succinate, oxalate, methanesulphonate or p-toluenesulphonate.

The compounds of formula (I) and pharmaceutically acceptable salts thereof may exist in solvated, for example hydrated, as well as unsolvated forms, and the present invention encompasses all such solvated forms.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) and their pharmaceutically acceptable salts have activity as pharmaceuticals, in particular as inhibitors of dipeptidyl peptidase I activity, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and *mycobacterium avium*, leprosy; other infectious diseases, such as fungal diseases, *chlamydia, candida, aspergillus*, cryptococcal meningitis, *pneumocystis carnii*, cryptosporidiosis, histoplasmosis, toxoplasmosis, trypanosome infection and leishmaniasis.

Thus, the present invention provides a compound of formula (I) or a pharmaceutically acceptable salt thereof as hereinbefore defined for use in therapy.

In a further aspect, the present invention provides the use of a compound of formula (I) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, the compounds of the invention (including pharmaceutically acceptable salts) may be used in the treatment of asthma {such as bronchial, allergic, intrinsic, extrinsic or dust asthma, particularly chronic or inveterate asthma (for example late asthma or airways hyper-responsiveness)}, chronic obstructive pulmonary disease (COPD) or allergic rhinitis.

The invention also provides a method of treating, or reducing the risk of, an obstructive airways disease or condition (e.g. asthma or COPD) which comprises administering to a patient in need thereof a therapeutically effective amount of a compound of formula (I) or a pharmaceutically acceptable salt thereof as hereinbefore defined.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals— The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or a pharmaceutically acceptable salt thereof as hereinbefore defined in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

Dry powder formulations and pressurized HFA aerosols of the compounds of the invention (that is, compounds of formula (I) and pharmaceutically acceptable salts thereof) may be administered by oral or nasal inhalation. For inhalation, the compound is desirably finely divided. The finely divided compound preferably has a mass median diameter of less than 10 micrometers (μm), and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethyl-cellulose as a thickening agent or other excipients known to those skilled in art.

The compounds of the invention (that is, compounds of formula (I) and pharmaceutically acceptable salts thereof) may also be administered in conjunction with other compounds used for the treatment of the above conditions.

The invention therefore further relates to combination therapies wherein a compound of the invention or a pharmaceutical composition or formulation comprising a compound of the invention is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with the following agents: non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention with a monoclonal antibody targeting B-Lymphocytes (such as CD20 (rituximab), MRA-aIL16R and T-Lymphocytes, CTLA4-Ig, HuMax I1-15).

The present invention still further relates to the combination of a compound of the invention with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C-X-C family) and $CX_3CR1$ for the $C-X_3-C$ family.

The present invention further relates to the combination of a compound of the invention with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention and a receptor antagonist for leukotrienes (LT) B4, LTC4, LTD4, and LTE4 selected from the group consisting of the phenothiazin-3-1s such as L-651, 392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention and a proton pump inhibitor (such as omeprazole) or a gastroprotective histamine type 2 receptor antagonist.

The present invention further relates to the combination of a compound of the invention and an antagonist of the histamine type 4 receptor.

The present invention still further relates to the combination of a compound of the invention and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention and an anticholinergic agents including muscarinic receptor (M1, M2, and M3) antagonist such as atropine, hyoscine, glycopyrrolate, ipratropium bromide, tiotropium bromide, oxitropium bromide, pirenzepine or telenzepine.

The present invention still further relates to the combination of a compound of the invention and a beta-adrenoreceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention and a chromone, such as sodium cromoglycate or nedocromil sodium.

The present invention still further relates to the combination of a compound of the invention with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention with an agent that modulates a nuclear hormone receptor such as PPARs.

The present invention still further relates to the combination of a compound of the invention together with an immunoglobulin (Ig) or Ig preparation or an antagonist or antibody modulating Ig function such as anti-IgE (for example omalizumab).

The present invention further relates to the combination of a compound of the invention and another systemic or topically-applied anti-inflammatory agent, such as thalidomide or a derivative thereof, a retinoid, dithranol or calcipotriol.

The present invention still further relates to the combination of a compound of the invention and combinations of aminosalicylates and sulfapyridine such as sulfasalazine, mesalazine, balsalazide, and olsalazine; and immunomodulatory agents such as the thiopurines.

The present invention further relates to the combination of a compound of the invention together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention and an agent for the treatment of acute or chronic pain, such as a centrally or peripherally-acting analgesic (for example an opioid or derivative thereof), carbamazepine, phenyloin, sodium valproate, amitryptiline or other anti-depressant agents, paracetamol, or a non-steroidal anti-inflammatory agent.

The present invention further relates to the combination of a compound of the invention together with a parenterally or topically-applied (including inhaled) local anaesthetic agent such as lignocaine or a derivative thereof.

A compound of the present invention can also be used in combination with an anti-osteoporosis agent including a hormonal agent such as raloxifene, or a biphosphonate such as alendronate.

The present invention still further relates to the combination of a compound of the invention together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cyclin dependent kinase); (viii) glucose-6 phosphate dehydrogenase inhibitor; (ix) kinin-B$_1$.- or B$_2$.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK$_1$ or NK$_3$ receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2×7; (xxvii) inhibitor of transcription factor activation such as NFkB, API, or STATS; or (xxviii) a glucocorticoid receptor agonist.

In a further aspect the present invention provides a combination (for example for the treatment of COPD, asthma or allergic rhinitis) of a compound of formula (I) or a pharmaceutically acceptable salt thereof as hereinbefore defined and one or more agents independently selected from:
- a non-steroidal glucocorticoid receptor (GR-receptor) agonist;
- a selective $\beta_2$ adrenoceptor agonist (such as metaproterenol, isoproterenol, isoprenaline, albuterol, salbutamol, formoterol, salmeterol, terbutaline, orciprenaline, bitolterol mesylate, pirbuterol or indacaterol);
- a phosphodiesterase inhibitor (such as a PDE4 inhibitor);
- a protease inhibitor (such as a neutrophil elastase or matrix metalloprotease MMP-12 inhibitor);
- a glucocorticoid;
- an anticholinergic agent;
- a modulator of chemokine receptor function (such as a CCR1 receptor antagonist); and
- an inhibitor of kinase function (such as the kinases p38 or IKK).

The invention also provides a pharmaceutical product comprising, in combination, a preparation of a first active ingredient which is a compound of formula (I) or a pharmaceutically acceptable salt thereof as hereinbefore defined, and a preparation of a second active ingredient which is
- a non-steroidal glucocorticoid receptor (GR-receptor) agonist;
- a selective $\beta_2$ adrenoceptor agonist;
- a phosphodiesterase inhibitor;
- a protease inhibitor;
- a glucocorticoid;
- an anticholinergic agent;
- a modulator of chemokine receptor function; or
- an inhibitor of kinase function;

for simultaneous, sequential or separate use in therapy.

In another aspect, the invention provides a kit comprising a preparation of a first active ingredient which is a compound of formula (I) or a pharmaceutically acceptable salt thereof as hereinbefore defined, and a preparation of a second active ingredient which is
- a non-steroidal glucocorticoid receptor (GR-receptor) agonist;
- a selective $\beta_2$ adrenoceptor agonist;
- a phosphodiesterase inhibitor;
- a protease inhibitor;
- a glucocorticoid;
- an anticholinergic agent;
- a modulator of chemokine receptor function; or
- an inhibitor of kinase function;

and instructions for the simultaneous, sequential or separate administration of the preparations to a patient in need thereof.

A compound of the invention can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholino propoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy) quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The invention will now be illustrated by the following non-limiting Examples in which, unless stated otherwise:

(i) when given, $^1$H NMR data is quoted and is in the form of delta values for major diagnostic protons, given in parts per million (ppm) relative to tetramethylsilane (TMS) as an internal standard, determined at 300 MHz or 400 MHz using perdeuterio d6-DMSO ($CD_3SOCD_3$) or $CDCl_3$ as the solvent unless otherwise stated;

(ii) mass spectra (MS) were run with an electron energy of 70 electron volts in the chemical ionisation (CI) mode using a direct exposure probe. Where indicated ionisation was effected by electrospray ionisation (ES), or atmospheric pressure chemical ionisation (APCI), or multimode ionisation, a combination of ES ionisation and APCI. Where values for m/z are given, generally only ions which indicate the parent mass are reported, and the mass ions quoted are the positive or negative mass ions: $[M]^+$, $[M+H]^+$ or $[M-H]^-$;

(iii) the title and sub-title compounds of the examples and preparations were named using the IUPAC name program Struct=Name 9.0.7 from CambridgeSoft Corporation.

(iv) unless stated otherwise, reverse phase HPLC was conducted using a Symmetry®, NovaPak® or Xterra® reverse phase silica column, all available from Waters Corp.; and (vi) the following abbreviations are used:

| | |
|---|---|
| AIBN | 2,2'-Azobisisobutyronitrile |
| Burgess reagent | Methyl (carboxysulfamoyl)triethyl ammonium hydroxide inner salt |
| CbzCl | Benzyloxycarbonylchloride |
| d | Day(s) |
| DCE | 1,2-Dichloroethane |
| DCM | Dichloromethane |
| DMF | N,N-Dimethylformamide |
| DMSO | Dimethyl sulfoxide |
| g | Gram(s) |
| h | Hour(s) |
| HATU | 2-(1H-7-Azabenzotriazol-1-yl)-1,1,3,3-tetramethyluronium hexafluorophosphate |
| HM-N | Argonaut Isolute ® diatomaceous earth cartridge |
| HPLC | High performance liquid chromatography |
| Hunig's Base | Diisopropylethylamine (DIPEA) |
| LCMS | Liquid chromatography- mass spectroscopy |
| min | Minute(s) |
| mL | Millilitre(s) |
| n-BuLi | n-Butyllithium |
| NMP | 1-Methylpyrrolidin-2-one |
| RPHPLC | Reverse phase high performance liquid chromatography |
| RT | Room temperature |
| SCX | Strong cation exchange resin |
| TBAF | Tetrabutylammonium fluoride |
| TBTU | O-(Benzotriazol-1-yl)-N,N,N',N'-tetramethyluronium tetrafluoroborate |
| TEA | Triethylamine |
| TFA | Trifluoroacetic acid |
| THF | THF |

INTERMEDIATE 1 tert-Butyl (2S)-2-({[(1S)-1-cyano-2-(4-iodophenyl)ethyl]amino}-carbonyl)piperidine-1-carboxylate

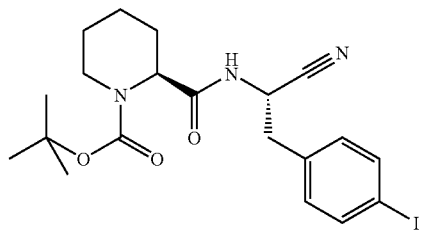

a) N-(tert-Butoxycarbonyl)-4-iodo-(L)-phenylalaninamide

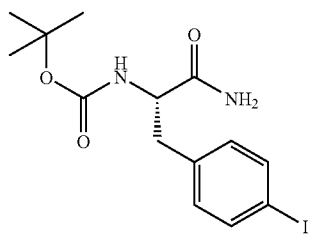

N-(tert-Butoxycarbonyl)-4-iodo-(L)-phenylalanine [*Tetrahedron: Asymmetry*, 1998, 9, 503] (12.73 g) was dissolved in DMF (120 mL) and to the resulting solution was added N-ethyl-morpholine (6.2 mL) and 2-(1-H-benzotriazole-1-yl)-1,1,3,3-tetramethyluronium tetrafluoroborate (10.45 g). The reaction mixture was stirred at room temperature for 0.5 h then cooled to 0° C. Aqueous ammonia (35%, 3.6 mL) was added and the mixture was allowed to reach room temperature overnight. The reaction mixture was poured into water (800 mL) and the precipitate that formed was removed by filtration and dried to give the sub-title compound (10.3 g) as a white solid.

$^1$H NMR (299.947 MHz, d6-DMSO) δ 7.62 (d, J=8.1 Hz, 2H), 7.36 (s, 1H), 7.07 (d, J=8.3 Hz, 2H), 7.01 (s, 1H), 6.80 (d, J=8.7 Hz, 1H), 4.10-4.00 (m, 1H), 2.94-2.86 (m, 1H), 2.73-2.62 (m, 1H), 1.30 (s, 9H)

m/z 389 [M–H]$^-$ b) 4-Iodo-(L)-phenylalaninamide

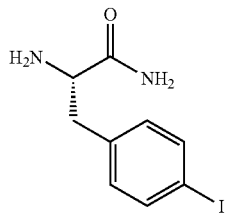

N-(tert-Butoxycarbonyl)-4-iodo-(L)-phenylalaninamide (4.24 g) was dissolved in DCM (20 mL) and to the solution was added TFA (20 mL). The reaction mixture was stirred, at room temperature, for 0.5 h then concentrated to dryness under reduced pressure. The crude material obtained was loaded onto an SCX cartridge. Non-basic impurities were washed off with a 1:1 mixture of DCM and methanol, then the cartridge was eluted with 10% ammonia in methanol. Eluent from the latter was concentrated to dryness to give the free base of the sub-title compound (3 g) as a white solid.

$^1$H NMR (299.947 MHz, d6-DMSO) δ 7.63-7.59 (m, 2H), 7.29 (s, 1H), 7.04 (dt, J=8.7, 2.1 Hz, 2H), 6.94 (s, 1H), 3.32-3.28 (m, 1H), 2.84 (dd, J=13.4, 5.1 Hz, 1H), 2.60-2.53 (m, 1H), 1.68 (s, 2H).

m/z 291 [M+H]$^+$ c) (S)-tert-Butyl 2-((S)-1-amino-3-(4-iodophenyl)-1-oxopropan-2-ylcarbamoyl)piperidine-1-carboxylate

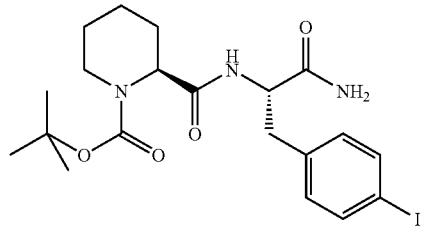

4-Iodo-(L)-phenylalaninamide (2 g), (2S)-1-(tert-butoxycarbonyl)piperidine-2-carboxylic acid (2.4 g) and disopropylethylamine (3 mL) were dissolved in DMF (10 mL) and to the solution was added 2-(1-H-benzotriazole-1-yl)-1,1,3,3-tetramethyluronium tetrafluoroborate (3.3 g). The reaction mixture was stirred at room temperature overnight. The reaction mixture was diluted with diethyl ether (200 mL) then washed with water (250 mL) and brine (4×250 mL). The organics were dried over magnesium sulfate, filtered and concentrated in vacuo. Crude product was purified by flash silica chromatography eluting with ethyl acetate to give the sub-title compound (2.88 g) as an oil.

$^1$H NMR (299.946 MHz, CDCl$_3$) δ 7.63 (dd, J=6.4, 1.8 Hz, 2H), 6.98 (dd, J=8.6, 2.0 Hz, 2H), 6.49 (d, J=7.9 Hz, 1H), 6.18-6.04 (m, 1H), 5.48 (s, 1H), 4.77-4.62 (m, 2H), 3.90-3.78 (m, 1H), 3.15-3.00 (m, 2H), 2.43-2.31 (m, 1H), 2.24-2.14 (m, 1H), 1.68-1.43 (m, 14H).

m/z 401 [M-BOC+H]$^+$ d) (S)-tert-Butyl 2-((S)-1-cyano-2-(4-iodophenyl)ethylcarbamoyl)piperidine-1-carboxylate

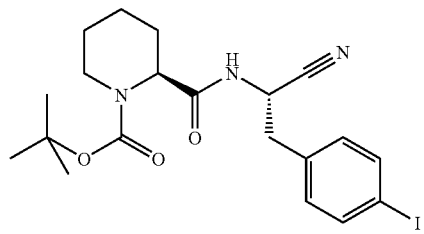

(S)-tert-Butyl 2-((S)-1-amino-3-(4-iodophenyl)-1-oxopropan-2-ylcarbamoyl)piperidine-1-carboxylate (2.88 g) was dissolved in DCM (40 mL) and to the solution was added (methoxycarbonylsulfamoyl)triethyl ammonium hydroxide (3.42 g). The reaction mixture was stirred under nitrogen, at room temperature overnight, then concentrated in vacuo. Crude material was purified by flash silica chromatography eluting with 20% ethyl acetate in isohexane to give the title compound (2.7 g) as a white solid.

$^1$H NMR (299.946 MHz, CDCl$_3$) δ 7.68 (dt, J=8.6, 2.0 Hz, 2H), 7.02-6.99 (m, 2H), 6.54 (s, 1H), 5.20-5.08 (m, 1H), 4.68 (s, 1H), 3.94 (s, 1H), 3.15-2.96 (m, 2H), 2.49-2.32 (m, 1H), 2.24-2.14 (m, 1H), 1.67-1.32 (m, 14H).

m/z 482 [M−H]$^−$

INTERMEDIATE 2

(S)-4'-(2-Amino-2-cyanoethyl)biphenyl-3-carbonitrile

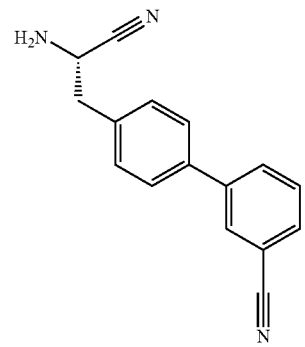

a) (S)-tert-Butyl 1-cyano-2-(4-iodophenyl)ethylcarbamate

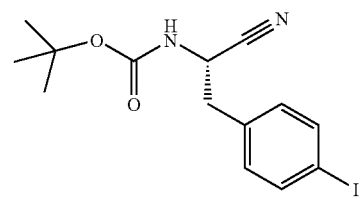

Triethylamine (43.2 mL) in DCM (150 mL) was stirred, under nitrogen, in a cold water bath and methyl chlorosulfonylcarbamate (21.01 g) in DCM (200 mL) was added dropwise. Once addition was complete, the cold water bath was removed and the mixture was stirred at room temperature for 30 min. (S)-tert-Butyl 1-amino-3-(4-iodophenyl)-1-oxopropan-2-ylcarbamate (18.9 g) was added and the mixture was stirred at room temperature for 18 h. The mixture was washed with water and brine then dried over magnesium sulfate, filtered and concentrated in vacuo. The crude product was purified by flash silica chromatography, eluting with 20% ethyl acetate in isohexane. Pure fractions were evaporated to dryness to afford (S)-tert-butyl 1-cyano-2-(4-iodophenyl) ethylcarbamate (16.46 g).

$^1$H NMR (299.946 MHz, CDCl$_3$) δ 7.70 (dt, J=8.7, 2.1 Hz, 2H), 7.03 (d, J=8.1 Hz, 2H), 4.89-4.67 (m, 2H), 3.02 (m, 2H), 1.44 (s, 9H).

b) (S)-tert-Butyl 1-cyano-2-(3'-cyanobiphenyl-4-yl)ethylcarbamate

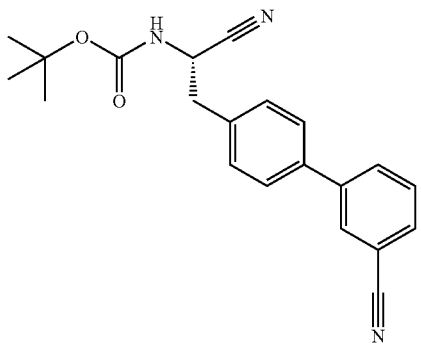

A solution of 3-cyanophenylboronic acid (4.74 g), (S)-tert-butyl 1-cyano-2-(4-iodophenyl)ethylcarbamate (10 g) and bis[bis(1,2-diphenylphosphino)-ethane]palladium (0) (0.243 g) in dioxane (100 mL) under nitrogen, was stirred for 10 min. A solution of potassium carbonate (7.43 g) in water (30 mL) was added and the resulting solution was stirred at 75° C. for 3 h. The cooled mixture was poured into water containing brine and extracted with ethyl acetate (3×150 mL). The combined organics were washed with saturated brine (3×50 mL), dried over sodium sulfate and adsorbed onto silica. The crude product was purified by flash silica chromatography, eluting with 20% ethyl acetate in isohexane. Pure fractions were evaporated to dryness to afford (S)-tert-butyl 1-cyano-2-(3'-cyanobiphenyl-4-yl)ethylcarbamate (8.42 g) as a pale yellow solid.

$^1$H NMR (399.824 MHz, CDCl$_3$) δ 7.86 (s, 1H), 7.80 (dt, J=7.9, 1.3 Hz, 1H), 7.65 (dt, J=7.7, 1.2 Hz, 1H), 7.59-7.53 (m, 3H), 7.41 (d, J=7.9 Hz, 2H), 4.94-4.74 (m, 2H), 3.17 (dd, J=13.7, 5.8 Hz, 1H), 3.11 (dd, J=13.7, 7.0 Hz, 1H), 1.45 (s, 9H).

c) (S)-4'-(2-Amino-2-cyanoethyl)biphenyl-3-carbonitrile

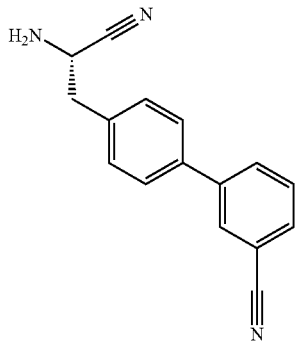

A suspension of (S)-tert-butyl 1-cyano-2-(3'-cyanobiphenyl-4-yl)ethylcarbamate (8.4 g) in formic acid (100 mL) was stirred and heated to 50° C. for 10 min. The mixture was concentrated in vacuo. The crude material was dissolved inmethanol (10 mL) and loaded on to an 50 g SCX cartridge. The impurities were washed through with methanol (100 mL) and discarded. The product was eluted with 1N methanolic ammonia (150 mL) and evaporated in vacuo. The residue was further purified by flash chromatography, eluting with ethyl acetate to afford (S)-4'-(2-amino-2-cyanoethyl)biphenyl-3-carbonitrile (3.32 g).

$^1$H NMR (299.946 MHz, CDCl$_3$) δ 7.89-7.77 (m, 2H), 7.65 (dt, J=7.7, 1.1 Hz, 1H), 7.60-7.52 (m, 3H), 7.43 (d, J=8.1 Hz, 2H), 4.05-3.94 (m, 1H), 3.18-3.03 (m, 2H), 1.73-1.63 (m, 2H)

INTERMEDIATE 3

(S)-2-Amino-3-(4-iodophenyl)propanenitrile

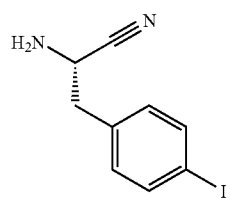

(S)-tert-Butyl 1-cyano-2-(4-iodophenyl)ethylcarbamate (1.4 g) and formic acid (3 mL) were combined and heated at 50° C. for 10 min. Solvent was removed in vacuo and crude material was loaded onto an SCX cartridge. Non-basic impurities were washed off with methanol, then product was eluted with 10% ammonia in methanol. Solvent was removed in vacuo to give (S)-2-amino-3-(4-iodophenyl)propanenitrile (0.900 g).

$^1$H NMR (399.826 MHz, d6-DMSO) δ 7.68 (d, J=8.2 Hz, 2H), 7.11 (d, J=8.2 Hz, 2H), 3.93 (dd, J=7.9, 6.9 Hz, 1H), 3.39-3.28 (m, 2H), 2.92-2.80 (m, 2H).

INTERMEDIATE 4

(S)-tert-Butyl 2-((S)-1-cyano-2-(4'-cyano-3'-fluorobiphenyl-4-yl)ethylcarbamoyl)piperidine-1-carboxylate

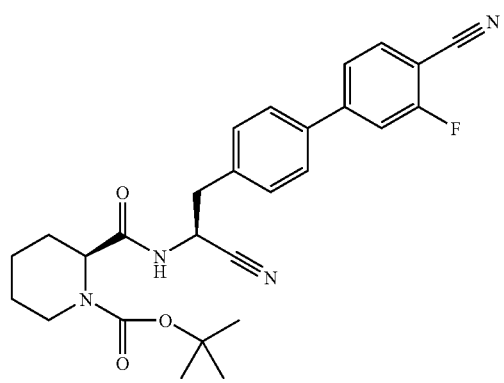

a) (S)-tert-Butyl 1-cyano-2-(4'-cyano-3'-fluorobiphenyl-4-yl)ethylcarbamate

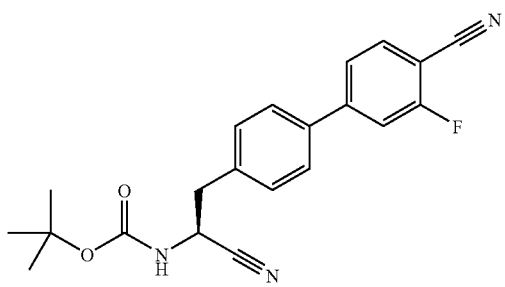

A solution of 4-cyano-3-fluorophenylboronic acid (0.736 g) dissolved in dioxane (10 mL) was added to a stirred solution of (S)-tert-butyl 1-cyano-2-(4-iodophenyl)ethylcarbamate (1.51 g) and bis[bis(1,2-diphenylphosphino)ethane]palladium (0) (0.037 g) in dioxane (20 mL) under nitrogen. The resulting mixture was stirred for 10 min. A solution of potassium carbonate (1.121 g) in water (5 mL) was added and the resulting solution was stirred at 75° C. for 3 h. The cooled mixture was evaporated to dryness. The residue was taken up in ethyl acetate (150 mL) and washed with saturated brine (3×50 mL), dried over sodium sulfate and adsorbed onto silica. The crude product was purified by flash silica chromatography, eluting with 20% ethyl acetate in isohexane. Pure fractions were evaporated to dryness to afford the subtitle compound as a colourless solid (0.568 g).

$^1$H NMR (299.946 MHz, CDCl$_3$) δ 7.70 (dd, J=8.0, 6.6 Hz, 1H), 7.59 (dt, J=8.4, 2.0 Hz, 2H), 7.49 (d, J=1.5 Hz, 1H), 7.45 (dd, J=6.2, 1.6 Hz, 1H), 7.42 (d, J=8.8 Hz, 2H), 4.94-4.76 (m, 2H), 3.23-3.06 (m, 2H), 1.45 (s, 9H)

b) (S)-4'-(2-Amino-2-cyanoethyl)-3-fluorobiphenyl-4-carbonitrile

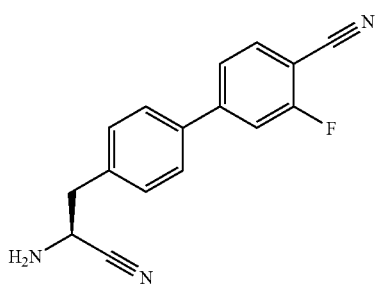

(S)-tert-Butyl 1-cyano-2-(4'-cyano-3'-fluorobiphenyl-4-yl)ethylcarbamate (0.580 g) was stirred in formic acid (8 mL) and heated at 50° C. for 10 min. The cooled mixture was evaporated, dissolved in methanol and applied to a 10 g SCX column. The column was washed with methanol then eluted with 10% ammonia in methanol. The eluate was evaporated to give a solid (0.335 g).

$^1$H NMR (399.824 MHz, CDCl$_3$) δ 7.69 (dd, J=8.2, 6.7 Hz, 1H), 7.58 (dt, J=8.3, 1.9 Hz, 2H), 7.47 (dd, J=8.1, 1.7 Hz, 1H), 7.44 (d, J=8.0 Hz, 2H), 7.42 (dd, J=10.1, 1.4 Hz, 1H), 4.02-3.96 (m, 1H), 3.15-3.05 (m, 2H), 1.66 (s, 2H)

c) (S)-tert-Butyl 2-((S)-1-cyano-2-(4'-cyano-3'-fluorobiphenyl-4-yl)ethylcarbamoyl)-piperidine-1-carboxylate

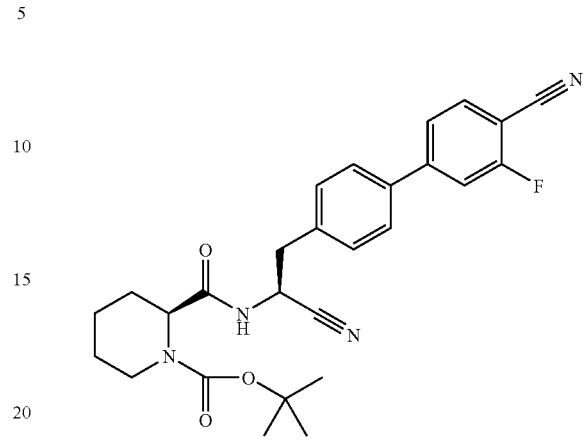

A 50% solution of propane phosphonic acid anhydride (0.964 g) (T3P) in DMF was added to a stirred solution of (S)-1-(tert-butoxycarbonyl)piperidine-2-carboxylic acid (0.290 g), (S)-4'-(2-amino-2-cyanoethyl)-3-fluorobiphenyl-4-carbonitrile (0.335 g) and triethylamine (0.880 mL) in DMF (3 mL) at 0° C. The resulting solution was allowed to warm to RT and stirred for 18 h. The mixture was poured into water and brine and the mixture extracted with ethyl acetate. The organics were washed with saturated brine, dried and evaporated. The crude product was purified by flash silica chromatography, eluting with 30% ethyl acetate in isohexane. Pure fractions were evaporated to dryness to afford (S)-tert-butyl 2-((S)-1-cyano-2-(4'-cyano-3'-fluorobiphenyl-4-yl)ethylcarbamoyl)piperidine-1-carboxylate as a colourless solid (0.443 g).

$^1$H NMR (399.824 MHz, CDCl$_3$) δ 7.70 (t, J=7.2 Hz, 1H), 7.57 (d, J=7.7 Hz, 2H), 7.46 (d, J=8.2 Hz, 2H), 7.43-7.38 (m, 3H), 5.26-5.15 (m, 1H), 4.72-4.65 (m, 1H), 4.04-3.88 (m, 1H), 3.22-3.11 (m, 2H), 2.58-2.40 (m, 1H), 2.25-2.15 (m, 2H), 1.69-1.58 (m, 4H), 1.45 (s, 9H).

INTERMEDIATE 5

(S)-tert-Butyl 2-((S)-2-(6-bromopyridin-3-yl)-1-cyanoethylcarbamoyl)piperidine-1-carboxylate

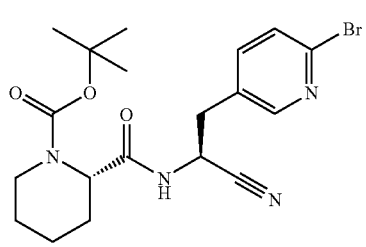

a) (S)-tert-Butyl 2-amino-3-(6-bromopyridin-3-yl) propanoate

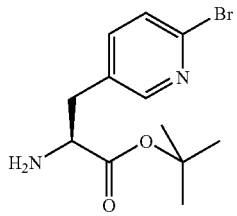

Prepared according to the procedures detailed in Patent WO2006/127948.

To a slurry of 2-bromo-5-methylpyridine (10.29 g) and N-bromosuccinimide (5.32 g) in carbon tetrachloride (150 mL) was added AIBN (200 mg) and the reaction vessel was purged with nitrogen. The reaction mixture was heated, under reflux, for 1.5 h then allowed to cool to room temperature. The reaction mixture was filtered and the filtrate was concentrated in vacuo to give 2-bromo-5-(bromomethyl)pyridine (4 g). This, together with tert-butyl 2-(diphenylmethyleneamino) acetate (4.71 g) and (2S,4S,5R)-2-((R)-allyloxy(quinolin-4-yl)methyl)-1-(anthracen-9-ylmethyl)-5-vinyl-1-azoniabicyclo[2.2.2]octane bromide (1.073 g) was dissolved in DCM (100 mL) and the solution was cooled to −78° C. under nitrogen. 2-tert-Butylimino-2-diethylamino-1,3-dimethyl-perhydro-1,3,2-diazaphosphorine (5 mL) was added dropwise over 5 min and the mixture was stirred at −78° C. for 7 h then allowed to reach RT overnight. The reaction mixture was concentrated in vacuo and partitioned between ethyl acetate and water. The ethyl acetate was washed with brine, dried over magnesium sulfate, filtered and concentrated in vacuo. The material obtained, (S)-tert-butyl 3-(6-bromopyridin-3-yl)-2-(diphenylmethyleneamino)propanoate (6 g), was dissolved in THF (75 mL) and to the solution was added citric acid (22 g) in water (75 mL). The mixture was stirred vigorously for 6 h then concentrated in vacuo and loaded onto an SCX cartridge. The cartridge was washed with water then methanol. The product was eluted with 10% ammonia in methanol. The solvent was removed in vacuo to give the sub-title compound (4.0 g).

m/z 301/303 [M+H]$^+$ b) (S)-2-Amino-3-(6-bromopyridin-3-yl)propanoic Acid

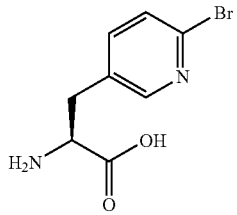

(S)-tert-Butyl 2-amino-3-(6-bromopyridin-3-yl)propanoate (4 g) was dissolved in DCM (20 mL) and the solution obtained was treated with TFA (20 mL). The mixture was stirred for 0.5 h, concentrated in vacuo, azeotroping with toluene, and loaded onto an NH$_2$-silica cartridge. Non acidic impurities were eluted with acetonitrile, then the desired product was eluted with 10% acetic acid in acetonitrile. Solvent was removed in vacuo to give the sub-title compound (2.5 g).

m/z 245/257 [M+H]$^+$ c) (S)-3-(6-Bromopyridin-3-yl)-2-(tert-butoxycarbonylamino)propanoic Acid

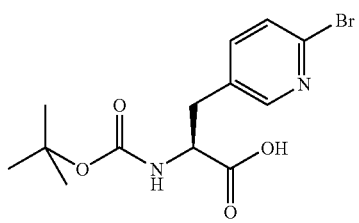

A slurry of (S)-2-amino-3-(6-bromopyridin-3-yl)propanoic acid (2.4 g) in dioxane (20 mL) was cooled to 0° C. and sodium hydroxide (19.59 mL, 1M) was added followed by di-tert-butyldicarbonate (2.73 mL). The reaction mixture was stirred at 0° C. for 1 h then at RT for 2 h. The pH of the reaction mixture was checked and brought to pH9 by addition of a drop of sodium hydroxide (1M). Solvent was removed in vacuo and the residue was partitioned between ethyl acetate and water. The water was brought to pH 2-3 with 2M hydrochloric acid and product was extracted with ethyl acetate. The ethyl acetate was washed with brine, dried over magnesium sulfate, filtered and concentrated in vacuo to give the sub-title compound (1.82 g).

$^1$H NMR (399.826 MHz, d6-DMSO) δ 8.25 (d, J=2.1 Hz, 1H), 7.64 (dd, J=8.2, 2.3 Hz, 1H), 7.57 (d, J=8.2 Hz, 1H), 7.19 (d, J=8.5 Hz, 1H), 4.16-4.09 (m, 1H), 3.08-3.01 (m, 1H), 2.84-2.76 (m, 1H), 1.30 (s, 9H) 1 resonance missing (acid).

d) (S)-tert-Butyl 1-amino-3-(6-bromopyridin-3-yl)-1-oxopropan-2-ylcarbamate

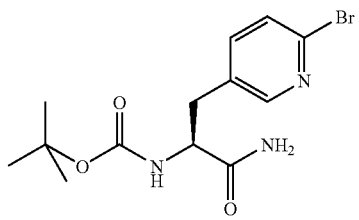

(S)-3-(6-Bromopyridin-3-yl)-2-(tert-butoxycarbonylamino)propanoic acid (1.72 g), N-ethylmorpholine (1.261 mL) and TBTU (2.4 g) were combined in DMF (5 mL) and the solution was stirred, at room temperature for 0.5 h then it was cooled to 0° C. Aqueous 880 ammonia (0.827 mL) was added and the mixture was allowed to reach RT overnight. The reaction mixture was diluted with ethyl acetate, washed with water then brine, dried over magnesium sulfate, filtered and concentrated in vacuo to give the sub-title compound (1.5 g).

e) (S)-2-Amino-3-(6-bromopyridin-3-yl)propanamide

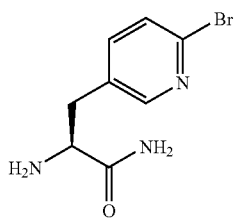

(S)-tert-Butyl 1-amino-3-(6-bromopyridin-3-yl)-1-oxopropan-2-ylcarbamate (1.5 g) was dissolved in DCM (20 mL) and to the solution was added TFA (10 mL). The reaction mixture was stirred for 0.5 h then concentrated in vacuo. Crude material was dissolved in methanol and loaded onto an SCX cartridge. Non-basic impurities were washed off with methanol, then product was eluted with 10% ammonia in methanol to give the sub-title compound (1.0 g).

$^1$H NMR (399.826 MHz, d6-DMSO) δ 8.22 (d, J=2.1 Hz, 1H), 7.60 (dd, J=8.2, 2.6 Hz, 1H), 7.55 (d, J=8.2 Hz, 1H), 7.32 (s, 1H), 6.98 (s, 1H), 3.37-3.27 (m, 1H), 2.86 (dd, J=13.6, 5.1 Hz, 1H), 2.62 (dd, J=13.6, 8.2 Hz, 1H), 1.91 (s, 2H)

f) (S)-tert-Butyl 2-((S)-1-amino-3-(6-bromopyridin-3-yl)-1-oxopropan-2-ylcarbamoyl)piperidine-1-carboxylate

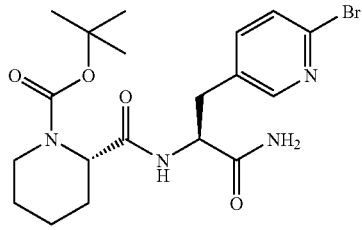

(S)-2-Amino-3-(6-bromopyridin-3-yl)propanamide (1 g), (S)-1-(tert-butoxycarbonyl)piperidine-2-carboxylic acid (0.939 g) and triethylamine (2.86 mL) in DMF (3 mL) were stirred under nitrogen at 0° C. 2,4,6-Tripropyl-1,3,5,2,4,6-trioxatriphosorinan-2,4,6-trioxide (3.13 g) was added and stirring at 0° C. was continued for 1 h. The reaction mixture was allowed to reach RT then it was diluted with ethyl acetate, washed with water and brine sequentially, dried over magnesium sulfate, filtered and concentrated in vacuo to give the sub-title compound (1.740 g).

m/z 355/357 [M+H]$^+$ g) (S)-tert-Butyl 2-((S)-2-(6-bromopyridin-3-yl)-1-cyanoethylcarbamoyl)piperidine-1-carboxylate

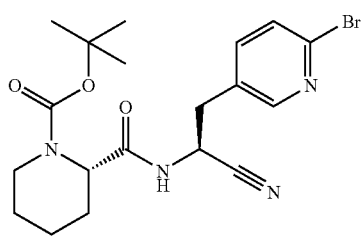

Triethylamine (3.46 mL) in DCM (5 mL) was stirred under nitrogen and to the solution was added a solution of methyl chlorosulfonylcarbamate (1.658 g) in DCM (5 mL). The mixture was stirred at room temperature for 15 min then a solution of (S)-tert-butyl 2-((S)-1-amino-3-(6-bromopyridin-3-yl)-1-oxopropan-2-ylcarbamoyl)piperidine-1-carboxylate (1.74 g) in DCM (5 mL) was added. Stirring was continued overnight. The reaction mixture was washed with water then brine, dried over magnesium sulfate, filtered and concentrated in vacuo. Crude product was purified by flash silica chromatography eluting with 40% ethyl acetate in isohexane to give the title compound (1.2 g) as a white solid.

$^1$H NMR (299.947 MHz, d6-DMSO) δ 8.64 (d, J=7.9 Hz, 1H), 8.31-8.27 (m, 1H), 7.73-7.66 (m, 1H), 7.61 (d, J=8.3 Hz, 1H), 5.16-5.07 (m, 1H), 4.58-4.33 (m, 1H), 3.80-3.69 (m, 1H), 3.23-3.11 (m, 2H), 2.88-2.77 (m, 1H), 1.96-1.86 (m, 1H), 1.58-1.20 (m, 13H), 1.06-0.90 (m, 1H)

INTERMEDIATE 6

(S)-tert-Butyl 2-((1R,2R)-2-(4-bromophenyl)-1-(methoxycarbonyl)cyclopropylcarbamoyl)piperidine-1-carboxylate

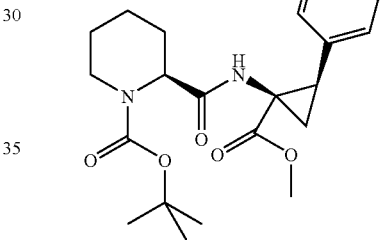

a) 5-(4-Bromobenzylidene)-2,2-dimethyl-1,3-dioxane-4,6-dione

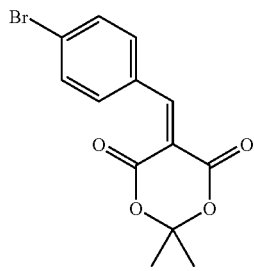

A mixture of N,N,N-trimethylhexadecan-1-aminium bromide (15.76 g), 4-bromobenzaldehyde (80 g) and 2,2-dimethyl-1,3-dioxane-4,6-dione (68.6 g) was heated and stirred at 60° C. for 1 h, during which time a solid precipitated from solution. The mixture was allowed to cool to room temperature. The solid was collected by filtration and washed with cold water (600 mL). dried in vacuo at 50° C. to give 5-(4-bromobenzylidene)-2,2-dimethyl-1,3-dioxane-4,6-dione (108 g) as a colourless solid.

$^1$H NMR (299.946 MHz, CDCL3) δ 8.35 (s, 1H), 7.94 (dd, J=8.6, 1.2 Hz, 2H), 7.63 (d, J=15.5 Hz, 2H), 1.85 (s, 6H).

b) 1-(4-Bromophenyl)-6,6-dimethyl-5,7-dioxaspiro[2.5]octane-4,8-dione

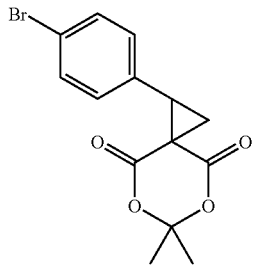

To a cooled solution of 5-(4-bromobenzylidene)-2,2-dimethyl-1,3-dioxane-4,6-dione (1.48 g) in DMF (20 mL) at 0-5° C. was added by dropwise addition a prepared solution of the dimethylsufoxonium-methylide from sodium hydride (60% in oil) (0.209 g), trimethylsulfoxonium iodide (1.152 g) in DMF (20 mL) at room temperature. Upon completion of addition the mixture was stirred at this temperature for a further 20 min. The mixture was then carefully poured onto a stirred mixture of ice/water and ethyl acetate. The crude product was extracted into ethyl acetate, washed well with saturated brine and dried over sodium sulfate. Filtration and evaporation gave the crude product. This sample was then recrystallised from a mixture of ethyl acetate:isohexane (3:1) to give the subtitle compound (0.670 g) as a colourless solid.

$^1$H NMR (299.946 MHz, CDCL3) δ 7.48 (d, J=8.3 Hz, 2H), 7.20 (d, J=8.5 Hz, 2H), 3.39 (t, J=9.4 Hz, 1H), 2.63 (dd, J=9.3, 4.9 Hz, 1H), 2.55 (ddd, J=9.5, 4.9, 0.6 Hz, 1H), 1.73 (d, J=9.8 Hz, 6H).

c) (E)-2-(4-Bromophenyl)-1-(methoxycarbonyl)cyclopropanecarboxylic Acid

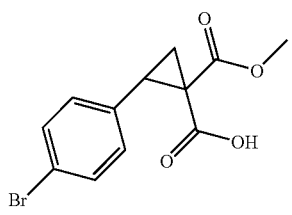

To a suspension of 1-(4-bromophenyl)-6,6-dimethyl-5,7-dioxaspiro[2.5]octane-4,8-dione (0.437 g) in methanol (5 mL) was added a stock solution (10 mL) prepared from potassium hydroxide (0.75 g) in methanol (100 mL). Upon addition a clear solution ensued and this mixture was stirred for 1 h. The mixture was evaporated to dryness and the residue taken up into water, filtered and then the filtrate was acidified to pH 3 by the addition of 1N hydrochloric acid. The oily precipitate was extracted into ethyl acetate and dried over sodium sulfate. Filtration and evaporation gave the subtitle compound (0.350 g) as a colourless gum.

$^1$H NMR (399.824 MHz, CDCl$_3$) δ 7.42 (dd, J=8.7, 2.1 Hz, 2H), 7.13 (d, J=8.5 Hz, 2H), δ 3.87 (s, 3H), 3.26 (t, J=9.1 Hz, 1H), 2.43 (dd, J=8.8, 5.0 Hz, 1H), 2.18 (dd, J=9.5, 4.9 Hz, 1H), acid resonance absent.

d) (Z)-Methyl 2-(4-bromophenyl)-1-(tert-butoxycarbonylamino)cyclopropanecarboxylate

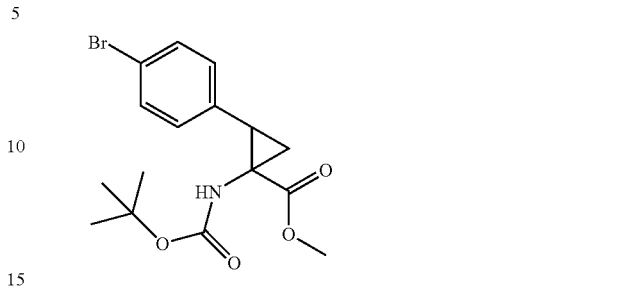

A mixture of diphenyl phosphorazidate (7.59 g), 2-(4-bromophenyl)-1-(methoxycarbonyl)cyclopropanecarboxylic acid (7.5 g), triethylamine (3.84 mL) in a mixture of toluene (300 mL) and tert-butanol (300 mL) was heated at 85° C. for 10 h. The mixture was diluted with water and the mixture was extracted with ether, washed with 5% aqueous citric acid, followed by saturated sodium hydrogen carbonate solution and dried over magnesium sulfate. The crude product was purified by flash silica chromatography, eluting with 1:1 diethyl ether/isohexane. Pure fractions were evaporated to dryness to afford methyl 2-(4-bromophenyl)-1-(tert-butoxycarbonylamino)cyclo-propanecarboxylate (4.60 g) as a colourless solid.

$^1$H NMR (399.824 MHz, CDCl$_3$) δ 7.43 (dt, J=8.8, 2.2 Hz, 2H), 7.06 (d, J=8.5 Hz, 2H), 4.58 (s, 1H), 3.78 (s, 3H), 2.92 (t, J=8.8 Hz, 1H), 2.13-2.02 (m, 1H), 1.75-1.65 (m, 1H), 1.35 (s, 9H).

e) (Z)-Methyl 1-amino-2-(4-bromophenyl)cyclopropanecarboxylate Hydrochloride

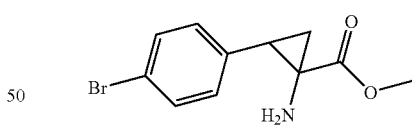

To a solution of (Z)-methyl 2-(4-bromophenyl)-1-(tert-butoxycarbonylamino)cyclo-propanecarboxylate (0.23 g) in dioxane (10 mL) was added 4.0 M hydrogen chloride in dioxane solution (10 mL) and the mixture allowed to stand for 1 h at RT. The mixture was evaporated to dryness and the residue triturated with diethyl ether to give a beige solid. This was collected and dried to afford the subtitle compound (0.161 g).

$^1$H NMR (399.826 MHz, d6-DMSO) δ 8.72 (s, 3H), 7.47 (dd, J=63.6, 8.2 Hz, 4H), 3.78 (s, 3H), 3.02 (t, J=9.1 Hz, 1H), 1.97-1.89 (m, 2H).

f) (S)-tert-Butyl 2-((1R,2R)-2-(4-bromophenyl)-1-(methoxycarbonyl)-cyclopropylcarbamoyl)piperidine-1-carboxylate

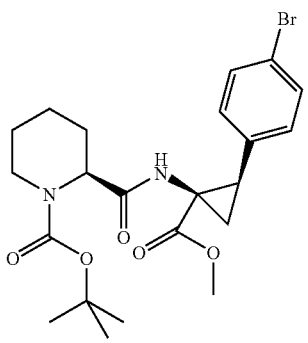

To a solution of (S)-1-(tert-butoxycarbonyl)piperidine-2-carboxylic acid (0.116 g) in DMF (10 mL) was added Hunig's Base (0.240 mL) followed by HATU (0.192 g). The mixture was allowed to stir at room temp for 10 min. To this solution was added in one portion (Z)-methyl 1-amino-2-(4-bromophenyl)cyclopropanecarboxylate hydrochloride (0.140 g) and the mixture stirred overnight. The mixture was evaporated to dryness, the residue extracted into ether and washed well with water and brine, then dried over sodium sulfate. The crude product was purified by flash silica chromatography, eluting with 50% diethyl ether/isohexane to give two diastereomers. Pure fractions were evaporated to dryness to afford the title compound (0.052 g).

$^1$H NMR (299.947 MHz, d6-DMSO) δ 7.91 (s, 1H), 7.26 (dd, J=79.7, 8.2 Hz, 4H), 4.32 (s, 1H), 3.72-3.52 (m, 4H), 3.10-2.94 (m, 1H), 2.78 (t, J=28.6 Hz, 1H), 1.80-1.53 (m, 3H), 1.44-1.03 (m, 14H).

Notes on Assignment of Stereochemistry

The stereochemistry of Intermediate 6 was assigned by derivatisation to known compounds [Mapelli, C.; Kimura, H.; Stammer, Charles H. Synthesis of four diastereomeric enkephalins incorporating cyclopropyl phenylalanine. *International Journal of Peptide & Protein Research* 1986, 28(4), 347-59].

(S)-tert-Butyl 2-((1R,2R)-2-(4-bromophenyl)-1-(methoxycarbonyl)-cyclopropylcarbamoyl)piperidine-1-carboxylate

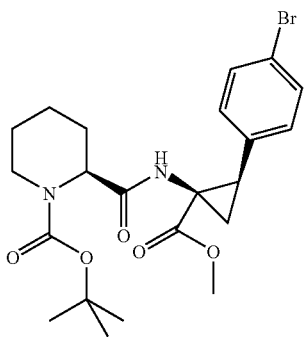

a) (1R,2R)-Methyl 1-amino-2-(4-bromophenyl)cyclopropanecarboxylate Hydrochloride b) (1S,2S)-Methyl 1-amino-2-(4-bromophenyl)cyclopropanecarboxylate Hydrochloride

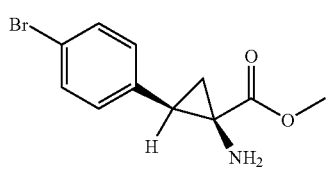

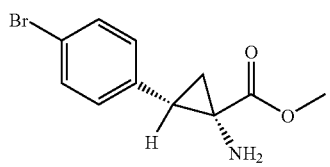

(Z)-Methyl 1-amino-2-(4-bromophenyl)cyclopropanecarboxylate hydrochloride racemate (1.3 g) was separated using a CHIRALPAK AD-H column eluting with neat methanol to give the two individual enantiomers with unassigned stereochemistry.

Sample (b) chiral purity 97.96% and sample (a) 86.21% (13.79% other enantiomer).

a) (1R,2R)-methyl 1-amino-2-phenylcyclopropanecarboxylate

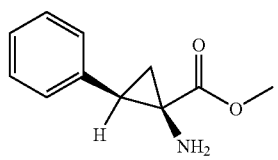

A mixture of (1R,2R)-methyl 1-amino-2-(4-bromophenyl)cyclopropanecarboxylate hydrochloride (120 mg) and palladium on carbon (10%) (47.3 mg) in methanol (20 mL) was stirred at 5 bar of hydrogen for 48 h. The catalyst was removed by filtration and the filtrate evaporated to dryness. The residue was purified by preparative HPLC on a Phenomenex Gemini column using a 95-5% gradient of aqueous 0.1% ammonia in acetonitrile as eluent. The fractions containing the desired compound were evaporated to dryness to afford (1R,2R)-methyl 1-amino-2-phenylcyclopropanecarboxylate (18 mg) as a colourless oil.

¹H NMR (399.824 MHz, CDCl₃) δ 7.35-7.22 (m, 5H), 3.77 (s, 3H), 2.83 (dd, J=9.4, 7.8 Hz, 1H), 1.84 (dd, J=9.7, 4.9 Hz, 1H), 1.57 (s, 2H), 1.44 (dd, J=7.6, 5.0 Hz, 1H).

b)
(1R,2R)-1-Amino-2-phenylcyclopropanecarboxylic Acid Hydrochloride

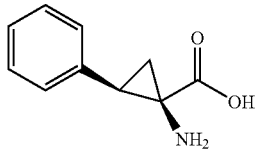

A mixture of (1R,2R)-methyl 1-amino-2-phenylcyclopropanecarboxylate (14 mg), water (4 mL) and hydrochloric acid (37% w/v, 6 mL) was heated under reflux for 6 h. The mixture was evaporated to dryness, triturated with diethyl ether and the solid collected and dried to give the subtitle compound (14 mg) as a colourless solid.

Optical Rotation: [α]D=+82.23 at 589 nm, solvent water, c=1.362 g/mL

Chiral purity 86.21% (contains 13.79% (1S,2S) enantiomer)

¹H NMR (399.825 MHz, D₂O) δ 7.50-7.40 (m, 5H), 3.27 (t, J=9.1 Hz, 1H), 2.05 (dd, J=9.9, 6.8 Hz, 1H), 1.90 (t, J=7.6 Hz, 1H).

Literature value: [α]D=+100 (c=0.7, water).

Mapelli, C.; Kimura, H.; Stammer, Charles H. Synthesis of four diastereomeric enkephalins incorporating cyclopropyl phenylalanine. *International Journal of Peptide & Protein Research* 1986, 28(4), 347-59.

Comparing rotation value to literature this sample and former precursors were assigned the (1R,2R) stereochemistry.

(S)-tert-Butyl 2-((1R,2R)-2-(4-bromophenyl)-1-(methoxycarbonyl)cyclopropyl-carbamoyl)piperidine-1-carboxylate

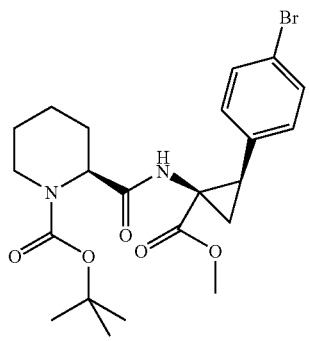

To a solution of (S)-1-(tert-butoxycarbonyl)piperidine-2-carboxylic acid (9.05 mg) in DMF (3 mL) was added Hunig's Base (0.019 mL) followed by HATU (15 mg). The mixture was allowed to stir at room temp for 10 min. To this solution was added in one portion (1R,2R)-methyl 1-amino-2-(4-bromophenyl)cyclopropanecarboxylate hydrochloride (11 mg) and the mixture was stirred overnight. The mixture was evaporated to dryness, the residue extracted into diethyl ether and washed well with water and brine, then dried over sodium sulfate. The sample was passed through a small silica plug/ eluting with diethyl ether to give (S)-tert-butyl 2-((1R,2R)-2-(4-bromophenyl)-1-(methoxycarbonyl)cyclopropylcarbamoyl)piperidine-1-carboxylate (6 mg) as a colourless oil.

NMR and TLC corresponds with Intermediate 6 therefore Intermediate 6 can be assigned (1R,2R) stereochemistry.

INTERMEDIATE 7

(S)-tert-Butyl 2-((1S,2S)-2-(4-bromophenyl)-1-(methoxycarbonyl)cyclopropylcarbamoyl)piperidine-1-carboxylate

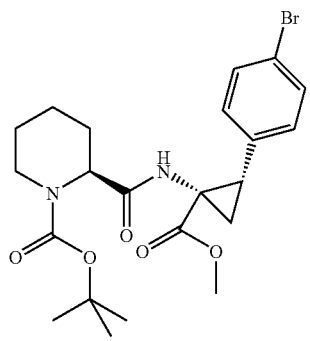

Obtained from Intermediate 6, step (f).

¹H NMR (299.947 MHz, d6-DMSO) δ 7.77 (s, 1H), 7.39 (d, J=8.2 Hz, 2H), 7.13 (d, J=8.5 Hz, 2H), 4.40 (s, 1H), 3.70 (s, 1H), 3.63 (s, 3H), 2.98 (t, J=8.7 Hz, 1H), 2.67 (t, J=12.1 Hz, 1H), 1.87 (d, J=13.1 Hz, 1H), 1.82-1.67 (m, 2H), 1.46-0.99 (m, 14H).

INTERMEDIATE 8

(1R,2R)-2-(4-Bromophenyl)-1-((S)-1-(tert-butoxycarbonyl)piperidine-2-carboxamido)cyclopropanecarboxylic Acid

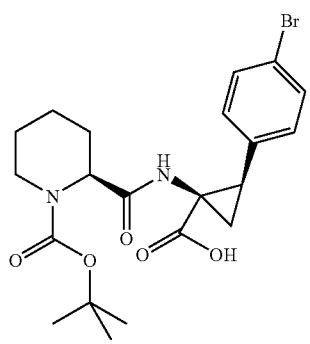

To a stirred solution of (S)-tert-butyl 2-((1R,2R)-2-(4-bromophenyl)-1-(methoxycarbonyl)-cyclopropylcarbamoyl)piperidine-1-carboxylate (3 g) in THF (45 mL) and water (30 mL) was added lithium hydroxide monohydrate (0.298 g). The mixture was stirred at RT for 2 h. The mixture was partitioned between 0.1 N HCl(aq) and ethyl acetate, and the aqueous phase was extracted twice more with ethyl acetate.

The combined organic phases were dried over sodium sulphate, filtered and concentrated in vacuo to leave the title compound (2.90 g) as a white solid.

$^1$H NMR (399.826 MHz, d6-DMSO) δ 12.46 (s, 1H), 7.99 (s, 0.5H), 7.95 (s, 0.5H), 7.43-7.35 (m, 2H), 7.13 (d, J=6.4 Hz, 2H), 4.46 (s, 0.5H), 4.34 (s, 0.5H), 3.74-3.66 (m, 0.5H), 3.63-3.53 (m, 0.5H), 3.32 (s, 1H), 2.99-2.89 (m, 1H), 2.74-2.63 (m, 0.5H), 2.58-2.49 (m, 0.5H), 1.89-1.82 (m, 1H), 1.76-1.66 (m, 2H), 1.37 (s, 4.5H), 1.27 (s, 4.5H), 1.21-0.82 (m, 4H); 1:1 mixture of rotamers.

m/z [M-BOC+H]+=367, 369; [M-H]-=465, 467.

INTERMEDIATE 9

(S)-tert-Butyl 2-((1R,2R)-2-(4-bromophenyl)-1-carbamoyl-cyclopropylcarbamoyl)piperidine-1-carboxylate

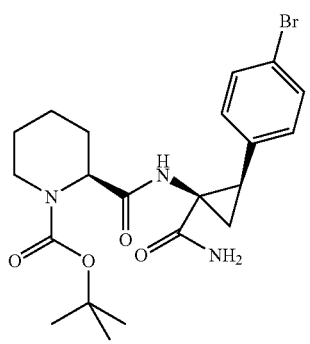

(1R,2R)-2-(4-Bromophenyl)-1-((S)-1-(tert-butoxycarbonyl)piperidine-2-carboxamido)cyclopropanecarboxylic acid (3 g) was dissolved in DMF (17 mL) and to the solution was added N-ethylmorpholine (1.219 mL) followed by TBTU (3.09 g). The reaction mixture was stirred at RT for 20 min then it was cooled to 0° C. Aqueous ammonia (1.461 mL) was added and the mixture was allowed to reach RT over 1 h. The reaction appeared to have proceeded ~70%, so it was left to stir for a further 2 h. LCMS showed little change so further TBTU (400 mg) and ammonia (0.3 mL) were added, and the mixture stirred for a further 2 h. The reaction mixture was partitioned between ethyl acetate and diluted brine, and reextracted into ethyl acetate twice more. The combined organic phases were dried over sodium sulfate, filtered and concentrated in vacuo to afford the title compound (2.75 g) as a pale gum.

m/z [M-BOC+H]+=366, 368.

INTERMEDIATE 10

(S)-tert-Butyl 2-((1R,2R)-2-(4-bromophenyl)-1-cyanocyclopropylcarbamoyl)piperidine-1-carboxylate

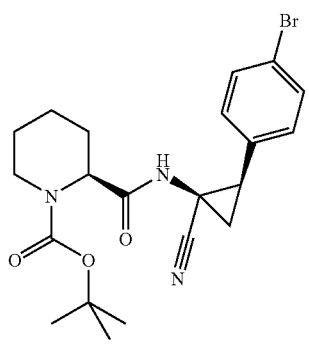

Triethylamine (5.26 mL) in DCM (50 mL) was stirred, under nitrogen, in a cold water bath and methyl chlorosulfonylcarbamate (2.56 g) was added portionwise. Once addition was complete, the cold water bath was removed and the mixture was stirred at room temperature for 30 min. (S)-tert-Butyl 2-((1R,2R)-2-(4-bromophenyl)-1-carbamoylcyclopropylcarbamoyl)piperidine-1-carboxylate (2.75 g) in DCM (60 mL) was added dropwise and the mixture was stirred at RT for 18 h. The mixture was washed with water and brine then dried over magnesium sulfate, filtered and concentrated in vacuo. The crude product was purified by flash silica chromatography, eluting with 1:2 through 1:1 ethyl acetate in isohexane. Appropriate fractions were concentrated in vacuo to yield the title compound (2.2 g) as a colourless gum.

$^1$H NMR (399.826 MHz, d6-DMSO) δ 8.44 (s, 1H), 7.46 (d, J=8.2 Hz, 2H), 7.18 (d, J=8.5 Hz, 2H), 4.46-4.30 (m, 1H), 3.71-3.53 (m, 1H), 3.05 (t, J=9.1 Hz, 2H), 2.44-2.29 (m, 1H), 1.97 (d, J=9.4 Hz, 2H), 1.77 (d, 3=13.8 Hz, 1H), 1.40-1.26 (m, 10H), 1.17 (t, J=7.7 Hz, 2H), 0.79-0.66 (m, 1H).

m/z [M-BOC+H]+=348, 350; [M-H]-=446, 448.

INTERMEDIATE 12 tert-Butyl (2S)-2-({[(1S)-1-cyano-2-(3-iodophenyl)ethyl]amino}-carbonyl)piperidine-1-carboxylate

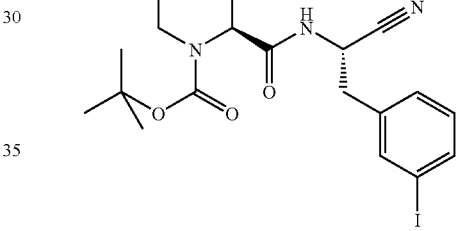

Prepared analogously to the method used for Intermediate 1, starting from N-(tert-butoxycarbonyl)-3-iodo-(L)-phenylalanine, a synthesis of which is described in Patent WO2005058943.

EXAMPLES

Method 1

EXAMPLE 1

(S)-N-((S)-2-(3'-Chlorobiphenyl-4-yl)-1-cyanoethyl)piperidine-2-carboxamide Trifluoroacetate

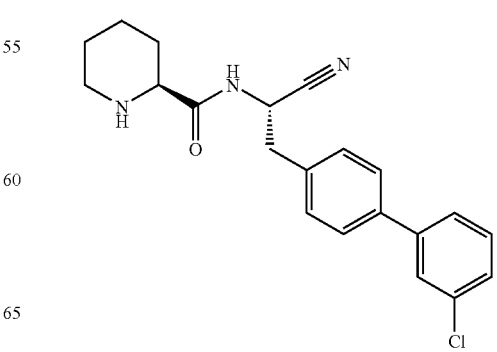

(S)-tert-Butyl 2-((S)-1-cyano-2-(4-iodophenyl)ethylcarbamoyl)piperidine-1-carboxylate (0.15 g) and bis[bis(1,2-diphenylphosphino)ethane]palladium(0) (2.80 mg) were dissolved in THF (2.5 mL) and stirred under nitrogen. 3-Chlorophenylboronic acid (0.063 g) in methanol (0.5 mL) was added and the mixture was stirred, at room temperature, for 10 min. Potassium carbonate (2M, 0.310 mL) was added and the reaction mixture was heated at 75° C. overnight. The crude reaction mixture was poured onto an Isolute® HM-N cartridge and product was eluted with DCM. The DCM was removed by evaporation under reduced pressure and the residue was dissolved in formic acid (5 mL). The acidic solution was heated at 50° C. for 0.5 h then concentrated in vacuo. The crude material was dissolved in methanol (5 mL) and loaded on to a 10 g SCX cartridge. The impurities were washed through with methanol (200 mL) and discarded. The product was eluted with 1N methanolic ammonia (200 mL) and evaporated in vacuo to give a white solid. This was purified by preparative HPLC on a Waters X-Bridge column using a 95-5% gradient of aqueous 0.1% TFA in acetonitrile as eluent. The fractions containing the desired compound were evaporated to dryness to afford the TFA salt of the title compound (0.07 g) as a white solid.

$^1$H NMR (299.947 MHz, d6-DMSO) δ 9.30 (d, J=6.9 Hz, 1H), 9.03-8.93 (m, 1H), 8.83-8.67 (m, 1H), 7.75-7.62 (m, 4H), 7.53-7.39 (m, 4H), 5.06 (q, J=7.5 Hz, 1H), 3.83-3.72 (m, 2H), 3.00-2.86 (m, 1H), 2.09-2.01 (m, 1H), 1.81-1.41 (m, 6H) m/z 368 [M+H]$^+$

Method 2

EXAMPLE 2

(S)-N-((S)-1-Cyano-2-(3'-(piperidin-1-ylmethyl)biphenyl-4-yl)ethyl)piperidine-2-carboxamide di-trifluoroacetate

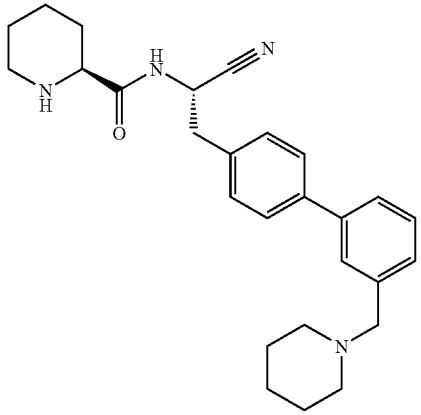

(S)-tert-Butyl 2-((S)-1-cyano-2-(4-iodophenyl)ethylcarbamoyl)piperidine-1-carboxylate (0.150 g) and bis[bis(1,2-diphenylphosphino)ethane]palladium (0) (2.80 mg) were dissolved in dioxane (5.0 mL) and stirred under nitrogen. 1-(3-(4,4,5,5-tetramethyl-1,3,2-dioxaborolan-2-yl)benzyl)piperidine hydrochloride (0.157 g) was added and the mixture was stirred, at room temperature, for 10 min. Potassium carbonate (2 M, 0.466 mL) was added and the reaction mixture was heated at 75° C. overnight. The crude reaction mixture was poured onto an Isolute HM-N cartridge and the product was eluted with DCM. The DCM was removed by evaporation under reduced pressure and the crude residue was dissolved in formic acid (5 mL). This acidic solution was heated at 50° C. for 0.5 h then concentrated in vacuo. The crude product was purified by RPHPLC on a Sunfire column using a 95-5% gradient of aqueous 0.1% TFA in acetonitrile as eluent. The fractions containing the desired compound were evaporated to dryness to afford the TFA salt of the title compound (0.06 g) as a white solid.

$^1$H NMR (399.826 MHz, d6-DMSO) δ 9.73 (s, 1H), 9.38 (d, J=6.9 Hz, 1H), 9.09-9.02 (m, 1H), 8.82-8.73 (m, 1H), 7.83 (s, 1H), 7.77 (d, J=8.2 Hz, 1H), 7.70-7.66 (m, 2H), 7.56 (t, J=7.7 Hz, 1H), 7.50-7.43 (m, 3H), 5.05 (q, J=7.4 Hz, 1H), 4.35 (d, J=4.9 Hz, 2H), 3.83-3.75 (m, 1H), 3.36 (d, J=11.8 Hz, 2H), 3.27-3.18 (m, 3H), 2.96-2.86 (m, 3H), 2.10-2.04 (m, 1H), 1.86-1.75 (m, 3H), 1.73-1.31 (m, 8H) m/z 431 [M+H]$^+$

Method 3

EXAMPLE 3

(S)-N-((S)-2-(Biphenyl-4-yl)-1-cyanoethyl)pyrrolidine-2-carboxamide

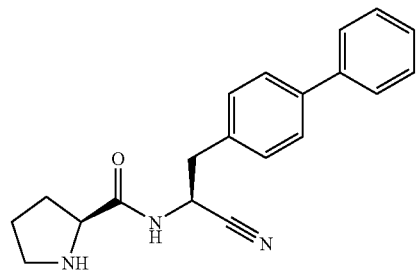

a) (S)-tert-Butyl 2-((S)-2-(biphenyl-4-yl)-1-cyanoethylcarbamoyl)pyrrolidine-1-carboxylate

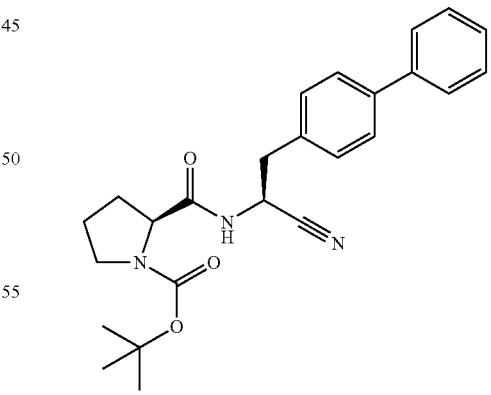

A solution of propane phosphonic acid anhydride (T3P, 50% in DMF, 344 mg) was added to a stirred solution of (S)-2-amino-3-(biphenyl-4-yl)propanenitrile (100 mg), N-tert-butoxycarbonyl-(L)-proline (107 mg) and triethylamine (0.314 mL) in DMF (3 mL) at 20° C. The resulting solution was stirred at 20° C. for 1 hour. Water (15 mL) was added and the mixture extracted with ethyl acetate (3×5 mL).

The organics were washed with saturated brine (5×5 mL), dried over sodium sulfate and evaporated to afford the subtitle compound (178 mg).

¹H NMR (299.946 MHz, CDCl₃) δ 7.60-7.54 (m, 4H), 7.48-7.41 (m, 2H), 7.39-7.29 (m, 3H), 5.27-5.04 (m, 1H), 4.33-4.18 (m, 1H), 3.56-3.23 (m, 2H), 3.22-3.04 (m, 2H), 2.52-2.06 (m, 1H), 1.92-1.68 (m, 3H), 1.45 (s, 9H).

b) (S)-N-((S)-2-(Biphenyl-4-yl)-1-cyanoethyl)pyrrolidine-2-carboxamide

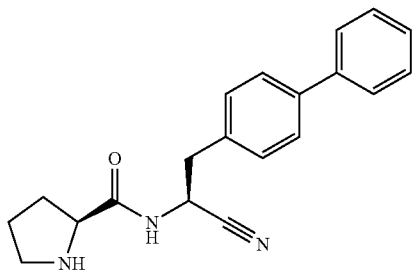

A solution of (S)-tert-butyl 2-((S)-2-(biphenyl-4-yl)-1-cyanoethylcarbamoyl)pyrrolidine-1-carboxylate (178 mg) in formic acid (5 mL) was stirred and heated at 50° C. for 10 min. The solvent was evaporated. The crude material was dissolved in methanol (2 mL) and loaded on to a 10 g SCX cartridge. The impurities were washed through with methanol (20 mL) and discarded. The product was eluted with 0.7 N methanolic ammonia (15 mL) and evaporated in vacuo. The residue was triturated with ethyl acetate (3 mL) and the solid collected, washed with a little ethyl acetate and dried to afford the title compound (92 mg).

¹H NMR (399.826 MHz, d6-DMSO) δ 8.64 (d, J=8.6 Hz, 1H), 7.66-7.58 (m, 4H), 7.46 (t, J=7.6 Hz, 2H), 7.38-7.33 (m, 3H), 5.05-4.97 (m, 1H), 3.53 (m, 14H), 3.20 (d, J=7.8 Hz, 2H), 2.95-2.85 (m, 1H), 2.81 (m, 1H), 2.67 (m, 1H), 1.82 (m, 1H), 1.53-1.31 (m, 3H).

EXAMPLE 4

(S)-N-((S)-2-(4-(1-Benzyl-1H-pyrazol-4-yl)phenyl)-1-cyanoethyl)-piperidine-2-carboxamide Trifluoroacetate

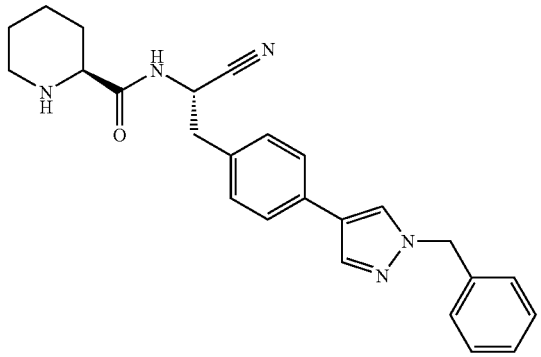

Prepared by a process analogous to the process described in Method 1, Example 1.

¹H NMR (399.826 MHz, d6-DMSO) δ 9.26 (d, J=7.4 Hz, 1H), 9.00-8.83 (m, 1H), 8.80-8.65 (m, 1H), 8.27 (d, J=3.8 Hz, 1H), 7.91 (d, J=4.6 Hz, 1H), 7.56-7.50 (m, 2H), 7.37-7.24 (m, 7H), 5.34 (s, 2H), 5.04-4.97 (m, 1H), 3.80-3.71 (m, 1H), 3.24-3.00 (m, 3H), 2.97-2.86 (m, 1H), 2.10-2.02 (m, 1H), 1.80-1.40 (m, 5H)

m/z 414 [M+H]⁺

EXAMPLE 5

(S)-N-((S)-2-(4'-Carbamoylbiphenyl-4-yl)-1-cyanoethyl)piperidine-2-carboxamide Trifluoroacetate

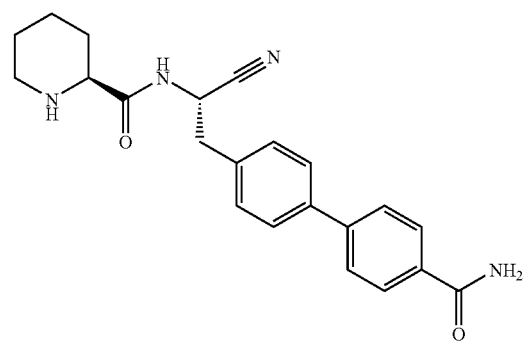

Prepared by a process analogous to the process described in Method 2, Example 2.

¹H NMR (399.826 MHz, d6-DMSO) δ 9.31 (d, J=7.2 Hz, 1H), 9.01-8.95 (m, 1H), 8.80-8.69 (m, 1H), 8.02 (s, 1H), 7.97 (d, J=8.5 Hz, 2H), 7.77-7.70 (m, 4H), 7.44 (d, J=8.2 Hz, 2H), 7.39 (s, 1H), 5.06 (q, J=7.5 Hz, 1H), 3.82-3.73 (m, 2H), 3.26-3.17 (m, 2H), 2.98-2.87 (m, 1H), 2.06 (d, J=12.8 Hz, 1H), 1.81-1.44 (m, 5H) m/z 377 [M+H]⁺

EXAMPLE 6

(S)-N-((S)-1-Cyano-2-(3'-cyanobiphenyl-4-yl)ethyl)piperidine-2-carboxamide Trifluoroacetate

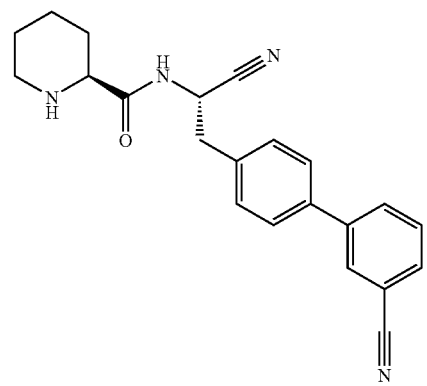

Prepared by a process analogous to the process described in Method 2, Example 2.

¹H NMR (299.947 MHz, d6-DMSO) δ 9.31 (d, J=7.3 Hz, 1H), 9.02-8.90 (m, 1H), 8.83-8.71 (m, 1H), 8.17 (s, 1H), 8.04 (d, J=7.9 Hz, 1H), 7.84 (d, J=7.5 Hz, 1H), 7.78-7.64 (m, 3H), 7.46 (d, J=8.1 Hz, 2H), 5.07 (q, J=7.4 Hz, 1H), 3.83-3.71 (m, 1H), 3.21 (d, J=7.1 Hz, 3H), 2.98-2.86 (m, 1H), 2.10-2.01 (m, 1H), 1.81-1.42 (m, 5H)

m/z 359 [M+H]$^+$

EXAMPLE 7

(S)-N-((S)-2-(3'-(Aminomethyl)biphenyl-4-yl)-1-cyanoethyl)piperidine-2-carboxamide Ditrifluoroacetate

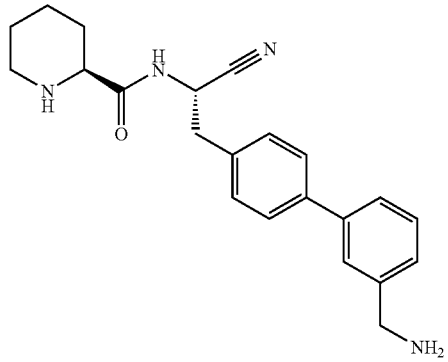

Prepared by a process analogous to the process described in Method 1, Example 1.

$^1$H NMR (399.826 MHz, d6-DMSO) δ 9.37 (d, J=7.2 Hz, 1H), 9.09-8.92 (m, 1H), 8.84-8.67 (m, 1H), 8.34-8.22 (m, 3H), 7.80 (s, 1H), 7.71-7.65 (m, 3H), 7.52 (t, J=7.7 Hz, 1H), 7.47-7.42 (m, 3H), 5.16-5.01 (m, 1H), 4.12 (d, J=5.4 Hz, 2H), 3.83-3.75 (m, 1H), 3.26-3.18 (m, 3H), 2.98-2.87 (m, 1H), 2.09-2.03 (m, 1H), 1.81-1.41 (m, 5H)

m/z 362 [M+H]$^+$

EXAMPLE 8

(S)-N-((S)-2-(3'-Acetamidobiphenyl-4-yl)-1-cyanoethyl)piperidine-2-carboxamide Trifluoroacetate

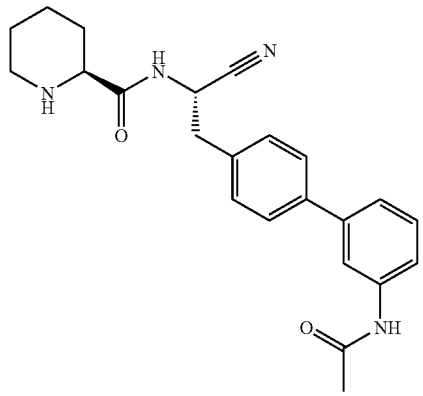

Prepared by a process analogous to the process described in Method 2, Example 2.

$^1$H NMR (399.826 MHz, d6-DMSO) δ 10.04 (s, 1H), 9.29 (d, J=7.2 Hz, 1H), 9.00-8.94 (m, 1H), 8.80-8.70 (m, 1H), 7.96 (s, 1H), 7.58 (d, J=8.2 Hz, 2H), 7.48 (d, J=8.5 Hz, 1H), 7.43-7.35 (m, 3H), 7.31 (d, J=7.7 Hz, 1H), 5.06 (q, J=7.4 Hz, 1H), 3.82-3.74 (m, 1H), 3.25-3.16 (m, 3H), 2.98-2.87 (m, 1H), 2.08-2.02 (m, 4H), 1.80-1.43 (m, 5H)

m/z 391 [M+H]$^+$

EXAMPLE 9

(S)-N-((S)-1-Cyano-2-(4'-(morpholinomethyl)biphenyl-4-yl)ethyl)piperidine-2-carboxamide Trifluoroacetate

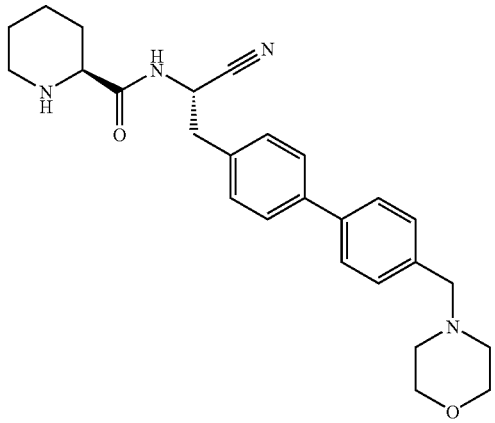

Prepared by a process analogous to the process described in Method 1, Example 1.

$^1$H NMR (399.826 MHz, d6-DMSO) δ 9.36 (d, J=7.2 Hz, 1H), 9.10-9.00 (m, 1H), 8.84-8.70 (m, 1H), 7.79 (d, J=8.2 Hz, 2H), 7.70 (d, J=8.2 Hz, 2H), 7.59 (d, J=8.2 Hz, 2H), 7.44 (d, J=8.5 Hz, 2H), 5.08-5.02 (m, 1H), 4.39 (s, 2H), 4.02-3.59 (m, 5H), 3.33-3.10 (m, 7H), 2.98-2.87 (m, 1H), 2.10-2.03 (m, 1H), 1.81-1.44 (m, 5H)

m/z 433 [M+H]$^+$

EXAMPLE 10

(S)-N-((S)-1-Cyano-2-(4-(pyridin-3-yl)phenyl)ethyl)piperidine-2-carboxamide Trifluoroacetate

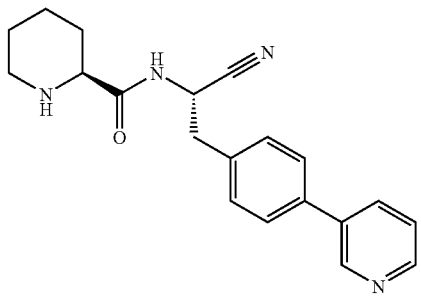

Prepared by a process analogous to the process described in Method 1, Example 1.

$^1$H NMR (399.826 MHz, d6-DMSO) δ 9.40-9.29 (m, 1H), 9.01-8.87 (m, 2H), 8.80-8.66 (m, 1H), 8.61 (dd, J=4.9, 1.5 Hz, 1H), 8.17 (dt, J=8.1, 1.9 Hz, 1H), 7.73 (t, J=7.9 Hz, 2H), 7.56 (dd, J=7.9, 4.9 Hz, 1H), 7.49-7.44 (m, 2H), 5.19-5.04 (m,

1H), 3.82-3.74 (m, 1H), 3.28-3.09 (m, 2H), 2.98-2.87 (m, 1H), 2.09-2.03 (m, 1H), 1.94-1.22 (m, 6H)

m/z 335 [M+H]+

EXAMPLE 11

(S)-N-((S)-1-Cyano-2-(4'-hydroxy-2'-methylbiphenyl-4-yl)ethyl)piperidine-2-carboxamide Trifluoroacetate

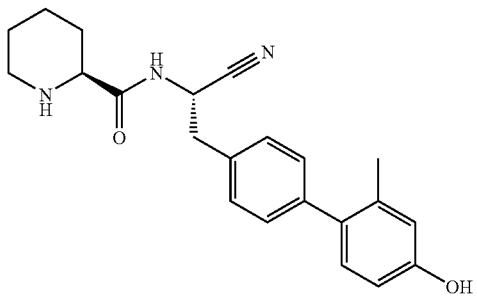

Prepared by a process analogous to the process described in Method 1, Example 1.

¹H NMR (399.826 MHz, d6-DMSO) δ 9.40-9.34 (m, 1H), 9.30 (d, J=7.2 Hz, 1H), 9.02-8.93 (m, 1H), 8.81-8.70 (m, 1H), 7.33 (d, J=8.2 Hz, 2H), 7.27-7.21 (m, 2H), 6.98 (d, J=8.2 Hz, 1H), 6.70-6.63 (m, 2H), 5.06-4.98 (m, 1H), 3.81-3.73 (m, 1H), 3.26-3.16 (m, 3H), 2.99-2.88 (m, 1H), 2.15 (s, 3H), 2.05-1.99 (m, 1H), 1.79-1.43 (m, 5H)

m/z 364 [M+H]+

EXAMPLE 12

4'-((S)-2-Cyano-2-((S)-piperidine-2-carboxamido)ethyl)biphenyl-3-carboxylic Acid Trifluoroacetate

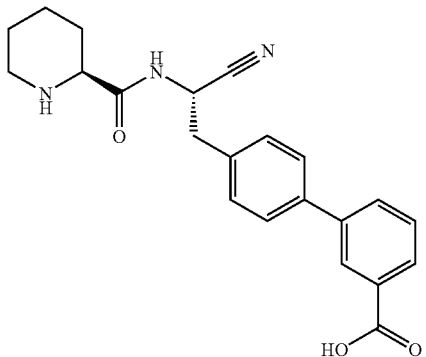

Prepared by a process analogous to the process described in Method 1, Example 1.

¹H NMR (399.826 MHz, d6-DMSO) δ 9.24 (1H, d), 8.18 (1H, s), 7.97-7.89 (2H, m), 7.72-7.66 (2H, m), 7.60 (1H, t), 7.44 (2H, d), 5.07 (1H, q), 3.76-3.69 (1H, m), 3.37-3.14 (5H, m), 2.95-2.83 (1H, m), 2.06-1.98 (1H, m), 1.79-1.41 (5H, m).

m/z 378 [M+H]+

EXAMPLE 13

(S)-N-((S)-1-Cyano-2-(2'-((R)-pyrrolidin-3-yloxy)biphenyl-4-yl)ethyl)piperidine-2-carboxamide Ditrifluoroacetate

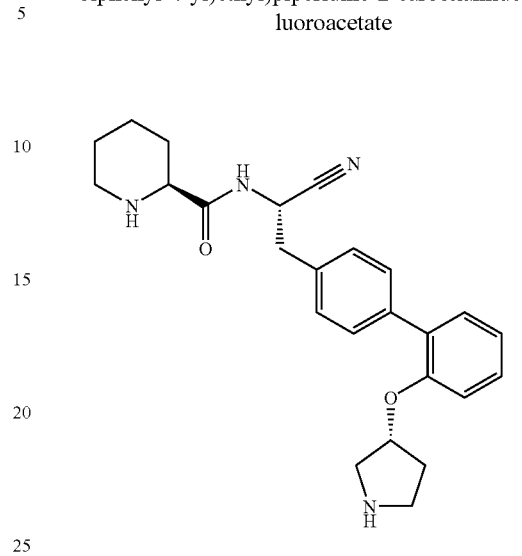

Prepared by a process analogous to the process described in Method 2, Example 2.

¹H NMR (399.826 MHz, d6-DMSO) δ 9.40 (d, J=7.2 Hz, 1H), 9.21-9.01 (m, 3H), 8.86-8.70 (m, 1H), 7.54-7.46 (m, 2H), 7.39-7.32 (m, 4H), 7.15-7.08 (m, 2H), 5.08-4.98 (m, 2H), 3.84-3.76 (m, 1H), 3.56-3.08 (m, 6H), 2.98-2.87 (m, 1H), 2.21-2.11 (m, 1H), 2.09-1.98 (m, 2H), 1.80-1.45 (m, 6H)

m/z 417 [M−H]−

EXAMPLE 14

(S)-N-((S)-2-(4-(1H-Indol-2-yl)phenyl)-1-cyanoethyl)piperidine-2-carboxamide Trifluoroacetate

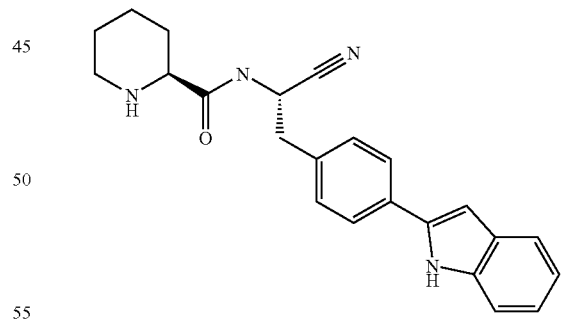

Prepared by a process analogous to the process described in Method 2, Example 2.

¹H NMR (399.826 MHz, d6-DMSO) δ 11.51 (s, 1H), 9.37-9.26 (m, 1H), 8.94-8.68 (m, 2H), 7.82 (t, J=8.5 Hz, 2H), 7.52 (d, J=7.7 Hz, 1H), 7.42-7.37 (m, 3H), 7.10 (t, J=7.2 Hz, 1H), 6.99 (t, J=7.0 Hz, 1H), 6.91 (d, J=1.5 Hz, 1H), 5.18-5.03 (m, 1H), 3.81-3.75 (m, 1H), 3.25-3.16 (m, 3H), 2.96-2.88 (m, 1H), 2.08-2.03 (m, 1H), 1.80-1.23 (m, 5H)

m/z 373 [M+H]+

EXAMPLE 15

(2S)-N-[(1S)-1-Cyano-2-(3'-methoxybiphenyl-4-yl)ethyl]piperidine-2-carboxamide Trifluoroacetate

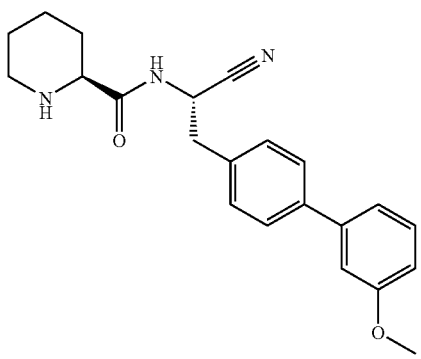

Prepared by a process analogous to the process described in Method 1, Example 1.

¹H NMR (399.826 MHz, CD₄OD) δ 7.53 (2H, d), 7.33-7.29 (4H, m), 7.14-7.08 (2H, m), 6.88 (1H, d), 4.89 (1H, br s), 4.05 (1H, br s), 3.85 (3H, s), 3.45 (1H, br s), 3.19-3.00 (3H, m), 2.11-1.50 (6H, m).

m/z 364 [M+H]⁺

EXAMPLE 16

Piperidine-2-carboxylic acid (2-biphenyl-4-yl-1-cyano-ethyl)-amide

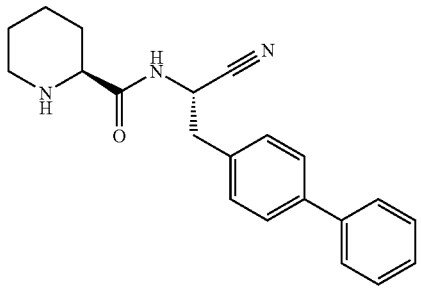

Prepared by a process analogous to the process described in Method 1, Example 1.

¹H NMR (399.826 MHz, d6-DMSO) δ 9.23 (d, J=10.3 Hz, 1H), 7.65-7.61 (m, 4H), 7.46-7.40 (m, 4H), 7.39-7.33 (m, 1H), 5.01 (q, J=7.5 Hz, 1H), 4.29 (s, 1H), 3.80 (d, J=13.6 Hz, 1H), 3.28-3.19 (m, 3H), 2.96-2.89 (m, 1H), 2.49 (t, J=2.6 Hz, 2H), 2.11-2.07 (m, 1H), 1.80-1.45 (m, 3H)

m/z [M+H]⁺=334

EXAMPLE 17

(2S,4R)-N-((S)-2-(Biphenyl-4-yl)-1-cyanoethyl)-4-hydroxypyrrolidine-2-carboxamide Prepared by a process analogous to the process described in Method 3, Example 3.

a) (2S,4R)-tert-Butyl 2-((S)-2-(biphenyl-4-yl)-1-cyanoethylcarbamoyl)-4-hydroxypyrrolidine-1-carboxylate ¹H NMR (399.824 MHz, CDCl₃) δ 7.59-7.54 (m, 4H), 7.47-7.42 (m, 2H), 7.38-7.31 (m, 3H), 5.21-5.07 (m, 1H), 4.40 (t, J=6.7 Hz, 2H), 3.41-3.34 (m, 2H), 3.20-3.06 (m, 2H), 2.63-2.51 (m, 1H), 2.03-1.92 (m, 1H), 1.59 (d, J=3.8 Hz, 1H), 1.46 (s, 9H).

b) (2S,4R)-N-((S)-2-(Biphenyl-4-yl)-1-cyanoethyl)-4-hydroxypyrrolidine-2-carboxamide ¹H NMR (399.826 MHz, d6-DMSO) δ 8.67 (d, J=8.2 Hz, 1H), 7.62 (m, 4H), 7.46 (t, J=7.6 Hz, 2H), 7.35 (m, 3H), 5.01 (m, 1H), 4.59 (d, J=3.3 Hz, 1H), 4.02 (s, 1H), 3.69 (t, J=8.2 Hz, 1H), 3.19 (d, J=7.7 Hz, 2H), 3.16-2.98 (m, 1H), 2.69 (m, 2H), 1.81 (m, 1H), 1.31 (m, 1H)

EXAMPLE 19

(S)-N-((S)-1-Cyano-2-(3'-cyanobiphenyl-4-yl)ethyl)azetidine-2-carboxamide

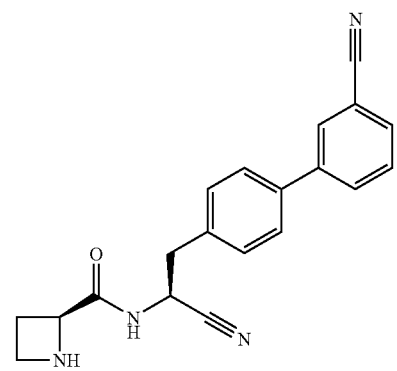

Prepared by a process analogous to the process described in Method 3, Example 3 using Intermediate 2.

a) (S)-tert-Butyl 2-((S)-1-cyano-2-(3'-cyanobiphenyl-4-yl)ethylcarbamoyl)azetidine-1-carboxylate ¹H NMR (399.824 MHz, CDCl₃) δ 7.84 (td, J=1.5, −0.1 Hz, 1H), 7.80 (dt, J=7.8, 1.5 Hz, 1H), 7.64 (dt, J=7.7, 1.4 Hz, 1H), 7.58-7.52 (m, 3H), 7.40 (d, J=8.2 Hz, 2H), 5.18-5.07 (m, 1H), 4.67 (t, J=7.9 Hz, 1H), 3.91 (q, J=8.2 Hz, 1H), 3.72 (dd, J=13.8, 8.5 Hz, 1H), 3.24-3.12 (m, 2H), 2.54-2.30 (m, 2H), 1.44 (s, 9H)

b) (S)-N-((S)-1-Cyano-2-(3'-cyanobiphenyl-4-yl)ethyl)azetidine-2-carboxamide ¹H NMR (399.826 MHz, d6-DMSO) δ 8.74 (d, J=8.5 Hz, 1H), 8.15 (s, 1H), 8.02 (d, J=7.9 Hz, 1H), 7.82 (d, J=7.4 Hz, 1H), 7.74 (d, J=7.7 Hz, 2H), 7.66 (t, J=7.7 Hz, 1H), 7.46 (d, J=7.7 Hz, 2H), 5.06 (q, J=7.9 Hz, 1H), 4.12 (t, J=8.2 Hz, 1H), 3.53 (q, J=7.9 Hz, 1H), 3.26 (d, J=7.7 Hz, 2H), 3.19-3.11 (m, 1H), 2.43-2.31 (m, 2H), 1.92-1.81 (m, 1H)

Method 4 for Parallel Synthesis

To each boronic acid or ester (0.4 mmol) was added (S-tert-butyl 2-((S)-1-cyano-2-(4-iodophenyl)ethylcarbamoyl)piperidine-1-carboxylate (0.31 mmol) in dioxane (3 mL). Bis[bis(1,2-diphenylphosphino)ethane]palladium (0) (2 mg) was added and the resulting mixtures were stirred for 10 min. An aqueous solution of potassium carbonate (2M, 0.3 mL) was added and the reaction mixtures were heated at 75° C. overnight. After cooling to room temperature, each reaction mixture was poured onto an Isolute HM-N cartridge and the crude product was eluted with DCM. The DCM was evaporated under reduced pressure and to each residue was added formic acid (2 mL). The solutions formed were heated at 50° C. for 1 h. The formic acid was then removed in vacuo. Dimethylsulfoxide (0.5 mL) was added to each of the residues and the crude solutions formed were purified by mass directed RPHPLC on an Atlantis C18 MS 30 mm column using a 95-05% gradient of aqueous 0.1% TFA in acetonitrile as eluent. The fractions containing the desired compound were evaporated to dryness to afford the compounds in Table 1 below.

TABLE 1

| Ex. No. | Name | Structure | m/z |
|---|---|---|---|
| 20 | (2S)-N-[(1S)-1-Cyano-2-[4-[4-(dimethylsulfamoyl)phenyl]phenyl]ethyl]piperidine-2-carboxamide trifluoroacetate | 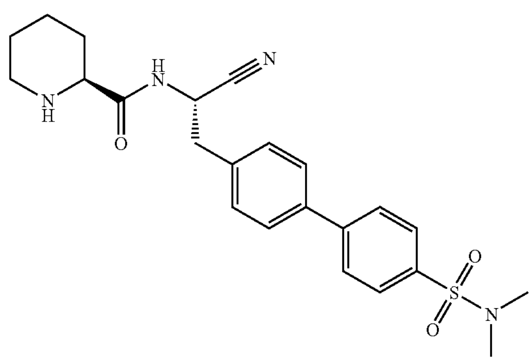 | 441[M + H]⁺ |
| 21 | (2S)-N-[(1S)-1-Cyano-2-(4-1,2-oxazol-4-ylphenyl)ethyl]piperidine-2-carboxamide trifluoroacetate | 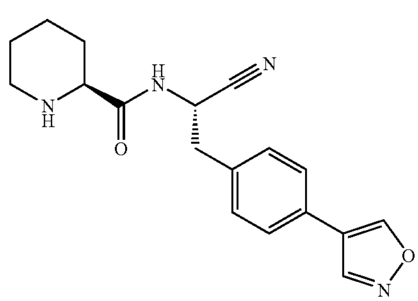 | 325[M + H]⁺ |

TABLE 1-continued parallel synthesis compounds

| Ex. No. | Name | Structure | m/z |
|---|---|---|---|
| 22 | (2S)-N-[(1S)-1-Cyano-2-[4-(3-methylsulfanylphenyl)phenyl]ethyl]piperidine-2-carboxamide trifluoroacetate | 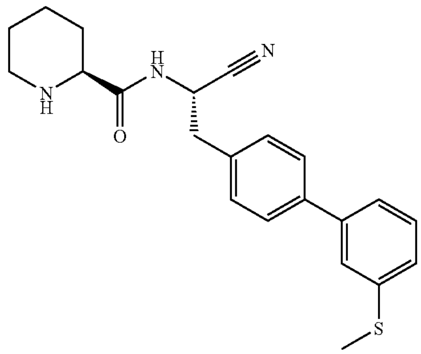 | 380[M + H]+ |
| 23 | (2S)-N-[(1S)-1-Cyano-2-[4-(4-hydroxyphenyl)phenyl]ethyl]piperidine-2-carboxamide trifluoroacetate | 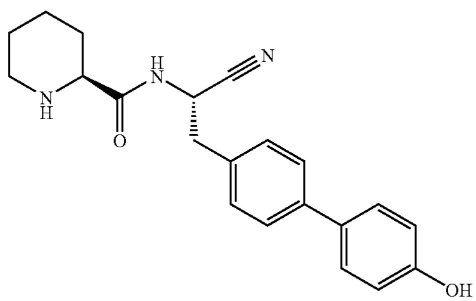 | 350[M + H]+ |
| 24 | (2S)-N-[(1S)-1-Cyano-2-[4-(4-cyanophenyl)phenyl]ethyl]piperidine-2-carboxamide trifluoroacetate | 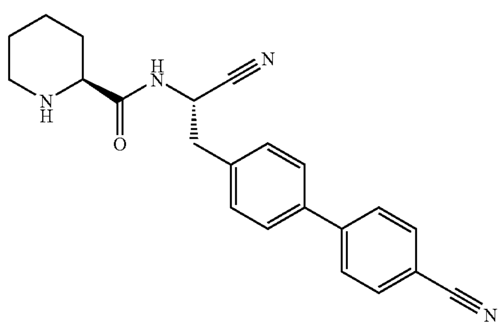 | 359[M + H]+ |
| 25 | (2S)-N-[(1S)-1-Cyano-2-[4-(4-methoxyphenyl)phenyl]ethyl]piperidine-2-carboxamide trifluoroacetate | 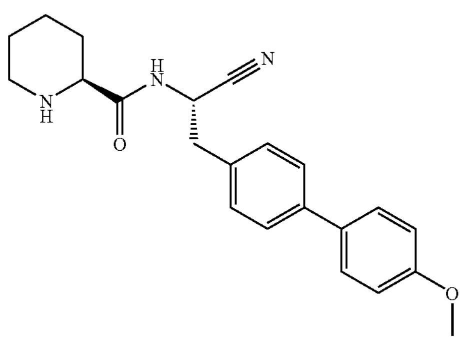 | 364[M + H]+ |

TABLE 1-continued parallel synthesis compounds

| Ex. No. | Name | Structure | m/z |
|---|---|---|---|
| 26 | (2S)-N-[(1S)-1-Cyano-2-[4-(1-methylpyrazol-4-yl)phenyl]ethyl]piperidine-2-carboxamide trifluoroacetate | 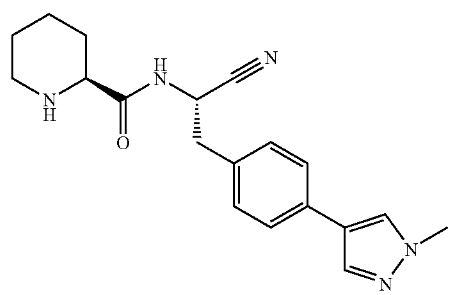 | 338[M + H]+ |
| 27 | (2S)-N-[(1S)-1-Cyano-2-[4-[4-(3-hydroxypropyl)phenyl]phenyl]ethyl]piperidine-2-carboxamide trifluoroacetate | 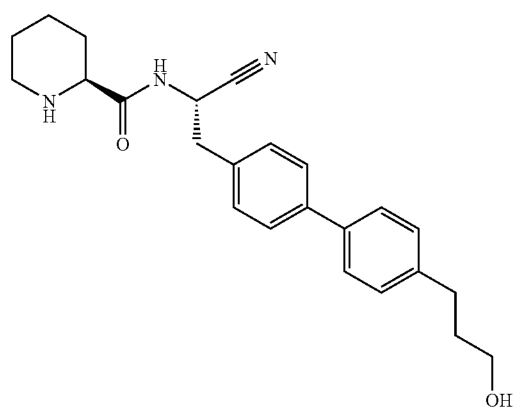 | 392[M + H]+ |
| 28 | (2S)-N-[(1S)-2-(4-Benzo[1,3]dioxol-5-ylphenyl)-1-cyano-ethyl]piperidine-2-carboxamide trifluoroacetate | 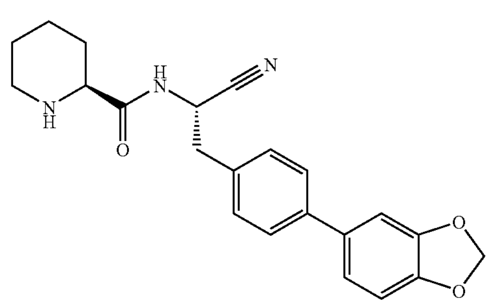 | 378[M + H]+ |
| 29 | (2S)-N-[(1S)-1-Cyano-2-[4-(3,4-difluorophenyl)phenyl]ethyl]piperidine-2-carboxamide trifluoroacetate | 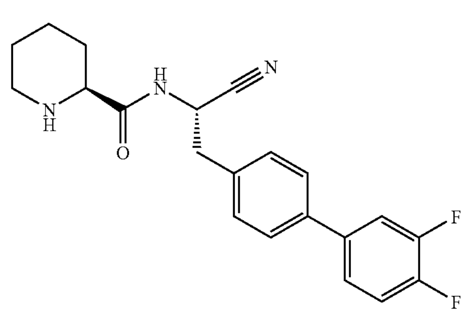 | 370[M + H]+ |

TABLE 1-continued parallel synthesis compounds

| Ex. No. | Name | Structure | m/z |
|---|---|---|---|
| 30 | (2S)-N-[(1S)-1-Cyano-2-[4-(4-fluoro-2-phenylmethoxy-phenyl)phenyl]ethyl]piperidine-2-carboxamide trifluoroacetate | 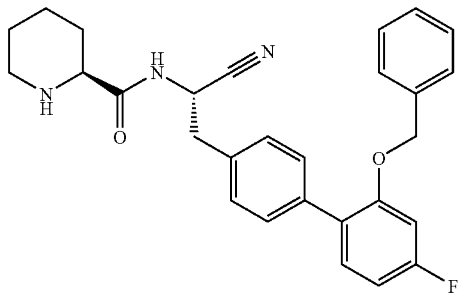 | 458[M + H]+ |
| 31 | (2S)-N-[(1S)-1-Cyano-2-[4-(3-fluoro-4-methoxy-phenyl)phenyl]ethyl]piperidine-2-carboxamide trifluoroacetate | 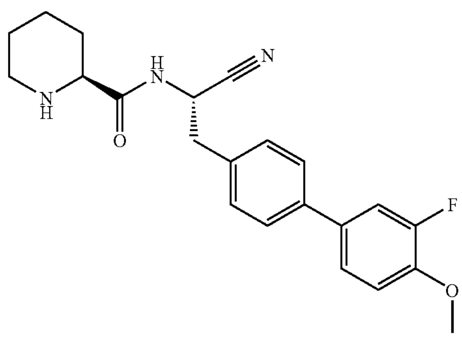 | 382[M + H]+ |
| 32 | (2S)-N-[(1S)-1-Cyano-2-[4-(3,4-dimethoxyphenyl)phenyl]ethyl]piperidine-2-carboxamide trifluoroacetate | 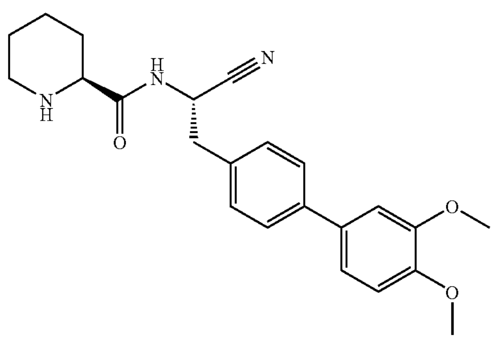 | 394[M + H]+ |
| 33 | (2S)-N-[(1S)-1-Cyano-2-[4-(2,4-dimethoxyphenyl)phenyl]ethyl]piperidine-2-carboxamide trifluoroacetate | 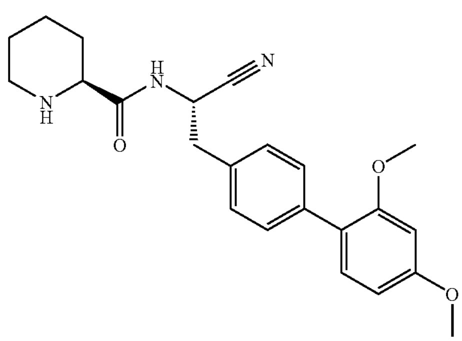 | 394[M + H]+ |

TABLE 1-continued parallel synthesis compounds

| Ex. No. | Name | Structure | m/z |
|---|---|---|---|
| 34 | (2S)-N-[(1S)-2-[4-(3-Carbamoylphenyl)phenyl]-1-cyano-ethyl]piperidine-2-carboxamide trifluoroacetate | 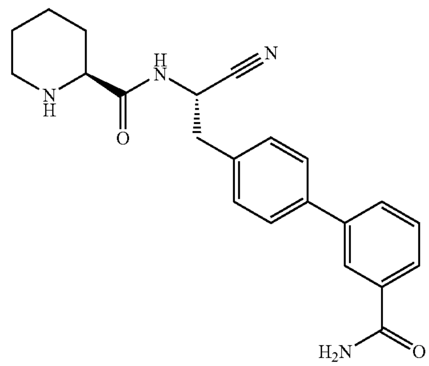 | 377[M + H]+ |
| 35 | (2S)-N-[(1S)-1-Cyano-2-[4-(2,5-dioxabicyclo[4.4.0]deca-7,9,11-trien-8-yl)phenyl]ethyl]piperidine-2-carboxamide trifluoroacetate | 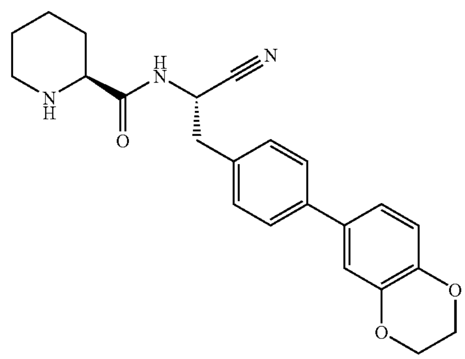 | 392[M + H]+ |
| 36 | (2S)-N-[(1S)-2-[4-[4-(Aminomethyl)phenyl]phenyl]-1-cyano-ethyl]piperidine-2-carboxamide trifluoroacetate | 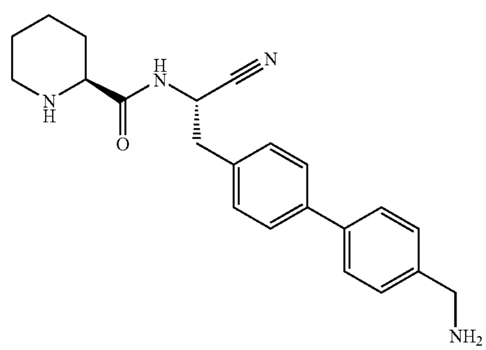 | 363[M + H]+ |
| 37 | (2S)-N-[(1S)-1-Cyano-2-[4-(2-dimethylaminopyrimidin-5-yl)phenyl]ethyl]piperidine-2-carboxamide trifluoroacetate | 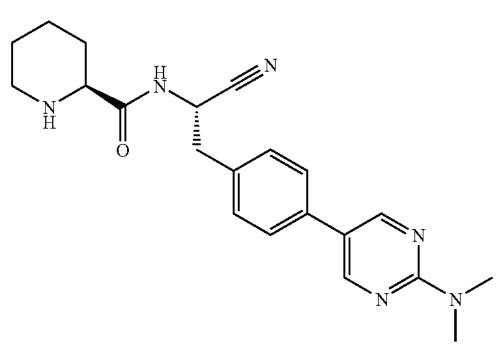 | 379[M + H]+ |

TABLE 1-continued parallel synthesis compounds

| Ex. No. | Name | Structure | m/z |
|---|---|---|---|
| 38 | (2S)-N-[(1S)-1-Cyano-2-[4-(4-methylthiophen-3-yl)phenyl]ethyl]piperidine-2-carboxamide trifluoroacetate | 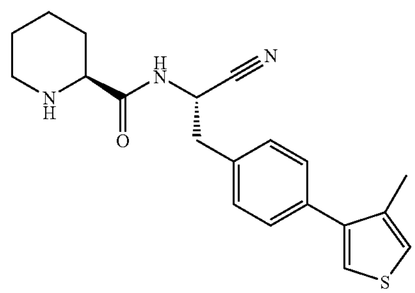 | 354[M + H]+ |
| 39 | (2S)-N-[(1S)-1-Cyano-2-[4-(3-fluoro-4-propoxy-phenyl)phenyl]ethyl]piperidine-2-carboxamide trifluoroacetate | 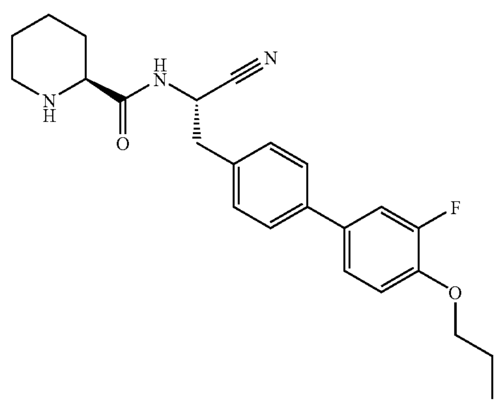 | 410[M + H]+ |
| 40 | (2S)-N-[(1S)-1-Cyano-2-[4-(2-methoxypyridin-3-yl)phenyl]ethyl]piperidine-2-carboxamide trifluoroacetate | 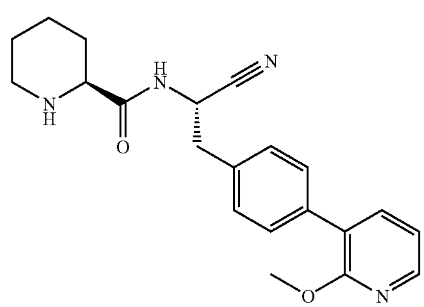 | 365[M + H]+ |
| 41 | (2S)-N-[(1S)-1-Cyano-2-[4-(2-methylpyrazol-3-yl)phenyl]ethyl]piperidine-2-carboxamide trifluoroacetate | 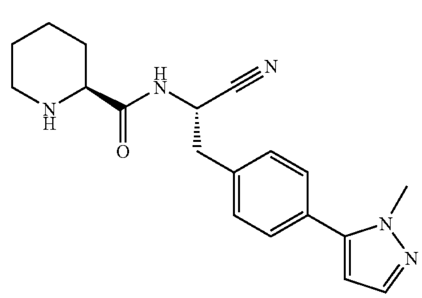 | 338[M + H]+ |

TABLE 1-continued parallel synthesis compounds

| Ex. No. | Name | Structure | m/z |
|---|---|---|---|
| 42 | (2S)-N-[(1S)-1-Cyano-2-[4-[3-(dimethylcarbamoyl)phenyl]phenyl]ethyl]piperidine-2-carboxamide trifluoroacetate | 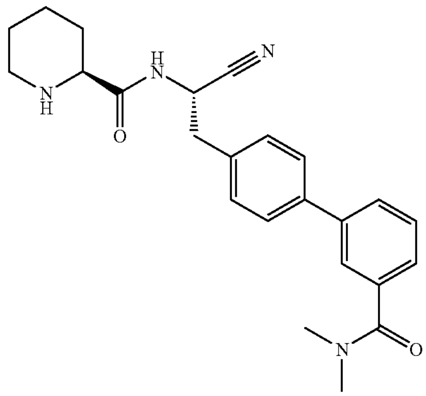 | 405[M + H]+ |
| 43 | (2S)-N-[(1S)-1-Cyano-2-[4-(4-ethylsulfonyl-2-methyl-phenyl)phenyl]ethyl]piperidine-2-carboxamide trifluoroacetate | 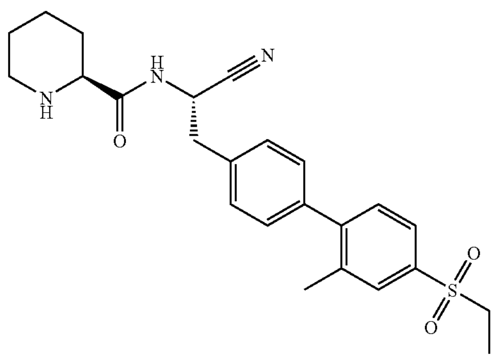 | 440[M + H]+ |
| 44 | (2S)-N-[(1S)-1-Cyano-2-[4-(3,5-difluoro-2-methoxy-phenyl)phenyl]ethyl]piperidine-2-carboxamide trifluoroacetate | 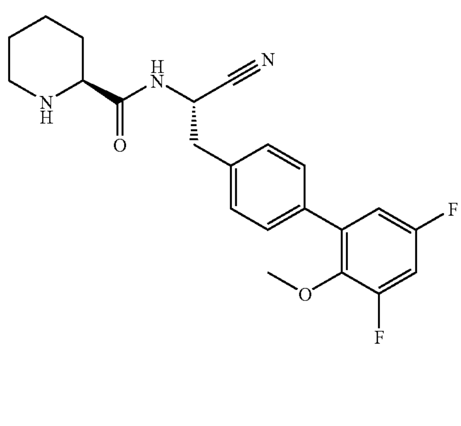 | 400[M + H]+ |

TABLE 1-continued parallel synthesis compounds

| Ex. No. | Name | Structure | m/z |
|---|---|---|---|
| 45 | (2S)-N-[(1S)-1-Cyano-2-[4-[3-(hydroxymethyl)phenyl]phenyl]ethyl]piperidine-2-carboxamide trifluoroacetate | 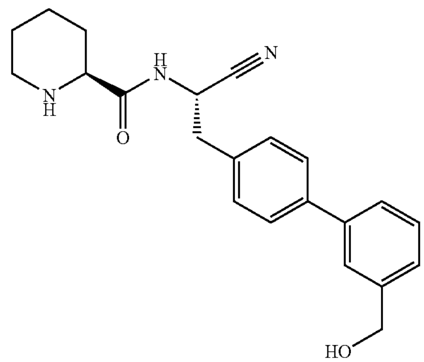 | 364[M + H]+ |
| 46 | (2S)-N-[(1S)-1-Cyano-2-[4-(2-methoxypyrimidin-5-yl)phenyl]ethyl]piperidine-2-carboxamide trifluoroacetate | 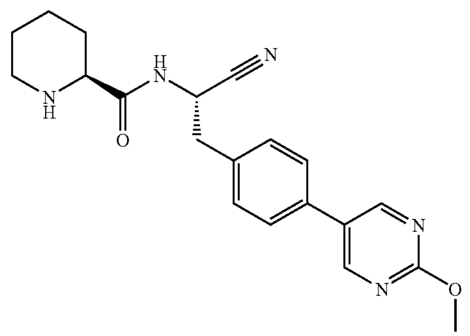 | 366[M + H]+ |
| 47 | (2S)-N-[(1S)-1-Cyano-2-[4-[6-(4-methylpiperazin-1-yl)pyridin-3-yl]phenyl]ethyl]piperidine-2-carboxamide trifluoroacetate | 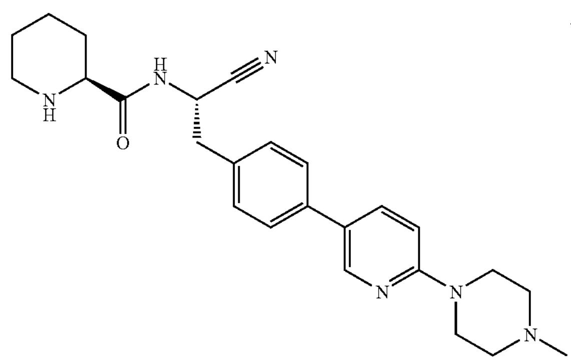 | 433[M + H]+ |
| 48 | (2S)-N-[(1S)-1-Cyano-2-[4-(2-hydroxyphenyl)phenyl]ethyl]piperidine-2-carboxamide trifluoroacetate | 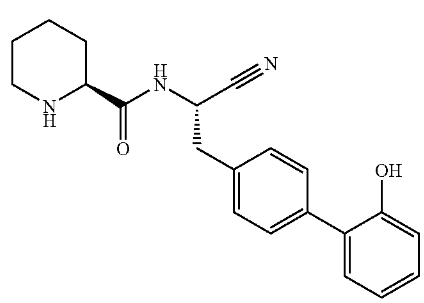 | 350[M + H]+ |

TABLE 1-continued parallel synthesis compounds

| Ex. No. | Name | Structure | m/z |
|---|---|---|---|
| 49 | (2S)-N-[(1S)-1-Cyano-2-(4-quinolin-8-ylphenyl)phenyl]piperidine-2-carboxamide trifluoroacetate | 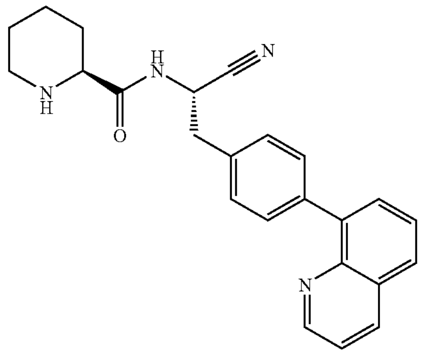 | 385[M + H]⁺ |
| 50 | (2S)-N-[(1S)-1-Cyano-2-[4-(2-methylphenyl)phenyl]ethyl]piperidine-2-carboxamide trifluoroacetate | 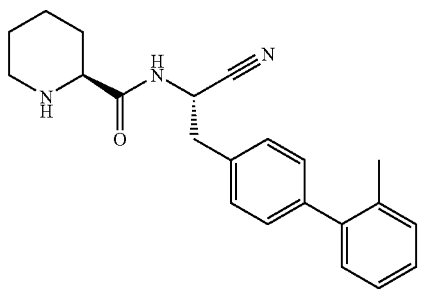 | 348[M + H]⁺ |
| 51 | (2S)-N-[(1S)-1-Cyano-2-[4-(2-phenylmethoxyphenyl)phenyl]ethyl]piperidine-2-carboxamide trifluoroacetate | 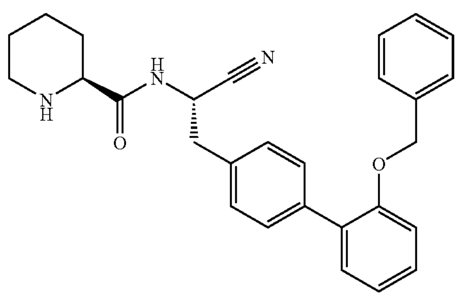 | 440[M + H]⁺ |
| 52 | (2S)-N-[(1S)-1-Cyano-2-[4-(2-methylpyridin-3-yl)phenyl]ethyl]piperidine-2-carboxamide trifluoroacetate | 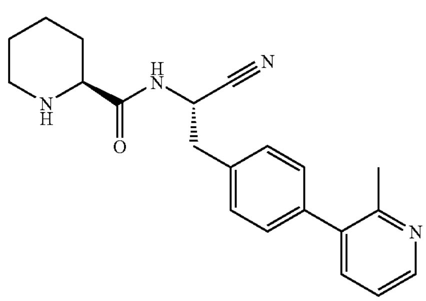 | 349[M + H]⁺ |

EXAMPLE 53

(S)-N-((S)-1-Cyano-2-(4-(6-cyanopyridin-3-yl)phenyl)ethyl)piperidine-2-carboxamide

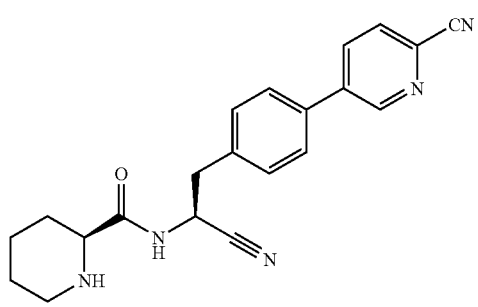

a) (S)-tert-Butyl 2-((S)-1-amino-1-oxo-3-(4-(4,4,5,5-tetramethyl-1,3,2-dioxaborolan-2-yl)phenyl)propan-2-ylcarbamoyl)piperidine-1-carboxylate

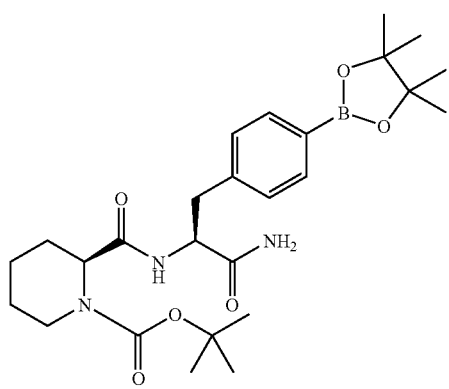

1,1'-Bis(diphenylphosphino)ferrocene (0.097 g) and 1,1'-bis(diphenylphosphino)ferrocene-palladium(II) dichloride DCM complex (0.141 g) were stirred in dry dimethylsulfoxide (5 mL) under nitrogen for 10 minutes. Potassium acetate (1.016 g), (S)-tert-butyl 2-((S)-1-amino-3-(4-iodophenyl)-1-oxopropan-2-ylcarbamoyl)piperidine-1-carboxylate (1.73 g) dissolved in dry DMSO (5 mL) and 4,4,4',4',5,5,5',5'-octamethyl-2,2'-bi(1,3,2-dioxaborolane) (1.165 g) were added and the reaction was heated at 80° C. overnight. The reaction mixture was cooled, diluted with water and extracted with ethyl acetate. The extracts were washed with brine then dried and evaporated. The crude material was purified by flash silica chromatography, eluting with ethyl acetate to give the subtitle compound as a colourless foam (1.28 g).

$^1$H NMR (399.824 MHz, CDCl$_3$) δ 7.75 (d, J=7.9 Hz, 2H), 7.24 (d, J=7.9 Hz, 2H), 6.48-6.39 (m, 1H), 5.30-5.23 (m, 1H), 4.72 (q, J=7.6 Hz, 1H), 4.67-4.62 (m, 1H), 3.22-3.14 (m, 1H), 3.13-3.06 (m, 1H), 2.48-2.36 (m, 1H), 2.25-2.18 (m, 1H), 1.53-1.45 (m, 4H), 1.42 (s, 9H), 1.33 (s, 12H).

m/z [M-BOC+H]$^+$=402.

b) (S)-tert-Butyl 2-((S)-1-amino-3-(4-(6-cyanopyridin-3-yl)phenyl)-1-oxopropan-2-ylcarbamoyl)piperidine-1-carboxylate

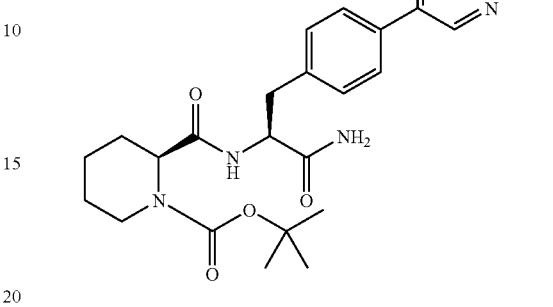

A solution of (S)-tert-butyl 2-((S)-1-amino-1-oxo-3-(4-(4,4,5,5-tetramethyl-1,3,2-dioxaborolan-2-yl)phenyl)propan-2-ylcarbamoyl)piperidine-1-carboxylate (0.150 g) in dioxane (1 mL) was added to a stirred solution of 5-bromopicolinonitrile (0.055 g) and bis[bis(1,2-diphenylphosphino)ethane]palladium (0) (0.003 g) in dioxane (1 mL) under nitrogen. The resulting mixture was stirred for 10 min. A solution of potassium carbonate (0.124 g) in water (0.75 mL) was added and the resulting solution was stirred at 75° C. for 16 h. The cooled mixture was evaporated to dryness. The residue was taken up in ethyl acetate and washed with saturated brine, dried over sodium sulfate and adsorbed onto silica. The crude product was purified by flash silica chromatography, eluting with 3:1 ethyl acetate/isohexane). Pure fractions were evaporated to dryness to afford the subtitle compound (0.113 g).

$^1$H NMR (399.824 MHz, CDCl$_3$) δ 7.56-7.52 (m, 2H), 7.48 (d, J=8.2 Hz, 1H), 7.37-7.31 (m, 3H), 7.18 (d, J=1.5 Hz, 1H), 5.40-5.30 (m, 1H), 4.70-4.63 (m, 1H), 3.51 (s, 3H), 3.26-3.11 (m, 2H), 2.51-2.30 (m, 1H), 2.26-2.18 (m, 1H), 1.56-1.46 (m, 2H), 1.43 (s, 9H), 1.41-1.28 (m, 4H).

m/z [M-BOC+H]$^+$=378.

c) (S)-tert-Butyl 2-((S)-1-cyano-2-(4-(6-cyanopyridin-3-yl)phenyl)ethylcarbamoyl)-piperidine-1-carboxylate

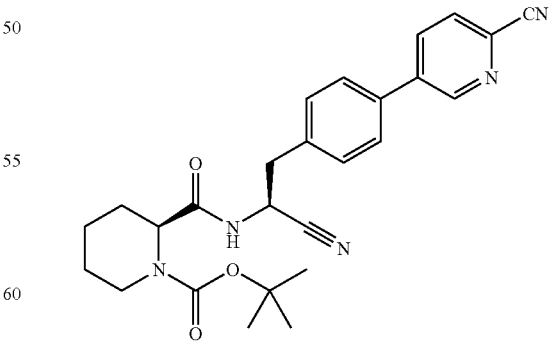

Triethylamine (0.209 mL) was stirred in DCM (5 mL), under nitrogen, in a cold water bath and methyl chlorosulfonylcarbamate (0.102 g) was added. The cold water bath was removed and the mixture was stirred at room temperature for 30 min. A solution of (S)-tert-butyl 2-((S)-1-amino-3-(4-(6-cyanopyridin-3-yl)phenyl)-1-oxopropan-2-ylcarbamoyl)piperidine-1-carboxylate (0.112 g) in DCM (5 mL) was added to the above mixture, and the resulting suspension was stirred at RT for 18 h. The mixture was washed with water and brine then dried and concentrated in vacuo. The residue was purified by flash silica chromatography eluting with 30% ethyl acetate in isohexane to give the subtitle compound as a foam (0.074 g).

m/z [M–H]⁻=458.

d) (S)-N-((S)-1-Cyano-2-(4-(6-cyanopyridin-3-yl)phenyl)ethyl)piperidine-2-carboxamide

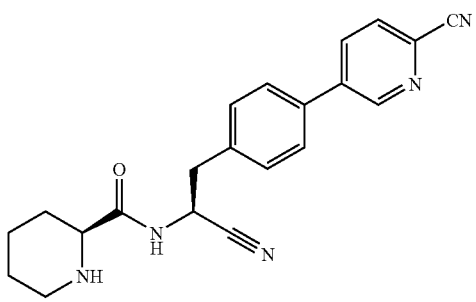

(S)-tert-Butyl 2-((S)-1-cyano-2-(4-(6-cyanopyridin-3-yl)phenyl)ethylcarbamoyl)-piperidine-1-carboxylate (0.074 g) in formic acid (3 mL) was heated at 50° C. for 10 min. The mixture was evaporated, dissolved in methanol and applied to a 10 g SCX column. The column was washed with methanol then eluted with 10% ammonia in methanol. The eluate was evaporated. The residue was triturated with isopropanol and the solid collected, washed with a little isopropanol and diethyl ether then dried to leave the title compound as a solid (0.048 g).

$^1$H NMR (499.914 MHz, d6-DMSO) δ 9.10 (d, J=1.3 Hz, 1H), 8.52 (d, J=7.4 Hz, 1H), 8.35 (dd, J=8.2, 2.2 Hz, 1H), 8.12 (d, J=8.0 Hz, 1H), 7.82 (d, J=8.0 Hz, 2H), 7.48 (d, J=8.0 Hz, 2H), 5.08-5.00 (m, 1H), 3.26-3.15 (m, 3H), 3.06 (d, J=8.4 Hz, 1H), 2.78 (d, J=12.4 Hz, 1H), 2.47-2.43 (m, 2H), 2.30-2.14 (m, 1H), 1.58 (d, J=9.0 Hz, 2H), 1.41 (d, J=14.4 Hz, 1H), 1.35-1.18 (m, 1H).

m/z [M+H]⁺=378.

EXAMPLE 54

(S)-N-((S)-1-Cyano-2-(4-(3-(2-hydroxyethyl)-2-oxo-2,3-dihydrobenzo[d]thiazol-5-yl)phenyl)ethyl)piperidine-2-carboxamide

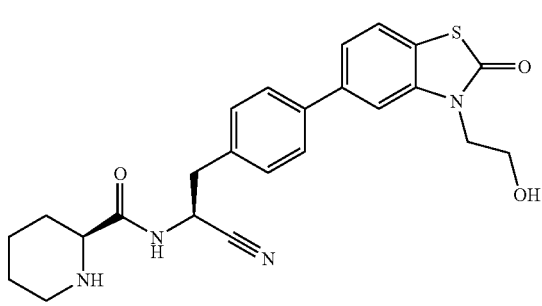

a) 5-Bromo-3-(2-hydroxyethyl)benzo[d]thiazol-2(3H)-one

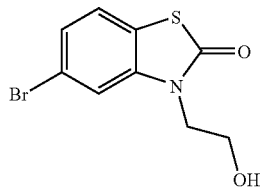

5-Bromobenzo[d]thiazol-2(3H)-one (1 g) and potassium carbonate (1.5 g) were stirred in DMF (7 mL) at room temperature and 2-bromoethanol (0.4 mL) added. The mixture was stirred for 48 h. The mixture was poured onto water and acidified with dilute hydrochloric acid and extracted with ethyl acetate. The extracts were washed with dilute hydrochloric acid, water and brine then dried over sodium sulfate and evaporated. Purification by flash silica chromatography eluting with 25% ethyl acetate in isohexane afforded the subtitle compound as a colourless solid (0.540 g).

$^1$H NMR (399.826 MHz, d6-DMSO) δ 7.64 (d, J=1.8 Hz, 1H), 7.61 (d, J=8.5 Hz, 1H), 7.36 (dd, J=8.5, 1.8 Hz, 1H), 4.91 (t, J=5.8 Hz, 1H), 4.01 (t, J=5.5 Hz, 2H), 3.64 (q, J=5.6 Hz, 2H).

b) (S)-N-((S)-1-Cyano-2-(4-(3-(2-hydroxyethyl)-2-oxo-2,3-dihydrobenzo[d]thiazol-5-yl)phenyl)ethyl)piperidine-2-carboxamide Prepared by method of Example 53 using 5-bromo-3-(2-hydroxyethyl)benzo[d]thiazol-2(3H)-one to give the title compound as a colourless solid.

$^1$H NMR (399.826 MHz, d6-DMSO) δ 10.65 (s, 1H), 9.30 (d, J=7.2 Hz, 1H), 9.03-8.67 (m, 1H), 7.64-7.60 (m, 3H), 7.49 (dd, J=8.5, 2.1 Hz, 1H), 7.38 (d, J=8.2 Hz, 2H), 7.05 (d, J=8.5 Hz, 1H), 5.03 (q, J=7.4 Hz, 1H), 3.81-3.72 (m, 1H), 3.50 (s, 2H), 3.25-3.13 (m, 4H), 2.98-2.86 (m, 1H), 2.09-2.01 (m, 1H), 1.81-1.74 (m, 1H), 1.73-1.65 (m, 1H), 1.64-1.53 (m, 1H), 1.52-1.43 (m, 1H).

m/z [M+H]⁺=421.

EXAMPLE 55

(S)-N-((S)-1-cyano-2-(4-(3-(2-methoxyethyl)-2-oxo-2,3-dihydrobenzo[d]thiazol-5-yl)phenyl)ethyl)piperidine-2-carboxamide

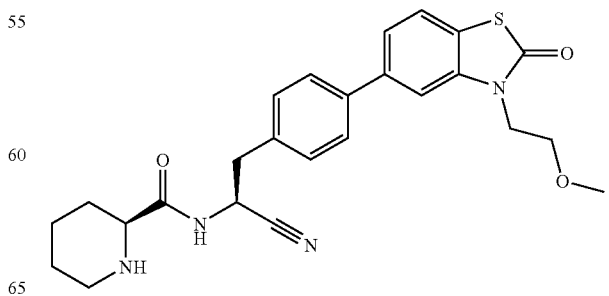

a) 5-Bromo-3-(2-methoxyethyl)benzo[d]thiazol-2(3H)-one

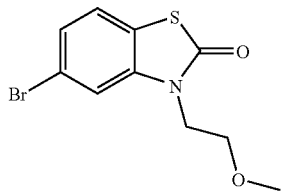

5-Bromobenzo[d]thiazol-2(3H)-one (1 g) and potassium carbonate (1.502 g) were stirred in DMF (7 mL) at room temperature and 1-bromo-2-methoxyethane (0.408 mL) was added. The mixture was stirred for 24 h. The mixture was poured onto water and extracted with ethyl acetate. The extracts were washed with dilute hydrochloric acid, water and brine then dried over sodium sulfate and evaporated. Purification by flash silica chromatography eluting with 10% ethyl acetate in isohexane afforded the subtitle compound as a colourless solid (0.73 g).

$^1$H NMR (399.824 MHz, CDCl$_3$) δ 7.36 (t, J=1.0 Hz, 1H), 7.28-7.26 (m, 2H), 4.09 (t, J=5.5 Hz, 2H), 3.68 (t, J=5.5 Hz, 2H), 3.34 (s, 3H).

b) (S)-N-((S)-1-cyano-2-(4-(3-(2-hydroxyethyl)-2-oxo-2,3-dihydrobenzo[d]thiazol-5-yl)phenyl)ethyl)piperidine-2-carboxamide Prepared by method of Example 53 using 5-bromo-3-(2-methoxyethyl)benzo[d]thiazol-2(3H)-one to give the title compound as a colourless solid.

$^1$H NMR (399.826 MHz, d6-DMSO) δ 9.29 (d, J=7.4 Hz, 1H), 8.96-8.88 (m, 1H), 8.81-8.70 (m, 1H), 7.75-7.68 (m, 3H), 7.63 (s, 1H), 7.50 (dd, J=8.2, 1.5 Hz, 1H), 7.44 (d, J=8.2 Hz, 1H), 5.06 (q, J=7.5 Hz, 1H), 4.24 (t, J=5.3 Hz, 2H), 3.81-3.73 (m, 1H), 3.65 (t, J=5.3 Hz, 2H), 3.24 (s, 3H), 3.22-3.17 (m, 3H), 2.99-2.87 (m, 1H), 2.10-2.03 (m, 1H), 1.81-1.74 (m, 1H), 1.73-1.66 (m, 1H), 1.65-1.44 (m, 3H).

m/z [M+H]$^+$=465.

EXAMPLE 56

(S)-N-((S)-1-Cyano-2-(4'-cyano-3'-fluorobiphenyl-4-yl)ethyl)piperidine-2-carboxamide

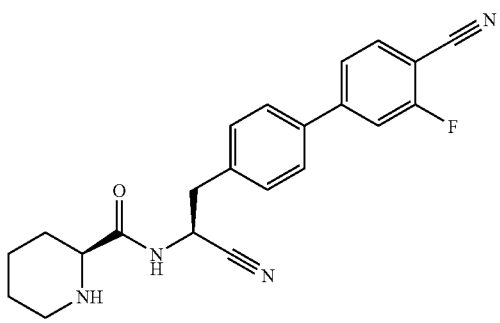

Prepared from Intermediate 4 by method analogous to Example 53(d).

$^1$H NMR (399.826 MHz, d6-DMSO) δ 8.51 (d, J=7.7 Hz, 1H), 8.00 (t, J=7.6 Hz, 1H), 7.89 (dd, J=11.1, 1.4 Hz, 1H), 7.81-7.73 (m, 3H), 7.45 (d, J=8.2 Hz, 2H), 5.07-4.99 (m, 1H), 3.26-3.14 (m, 2H), 3.09-3.03 (m, 1H), 2.81-2.75 (m, 1H), 2.49-2.42 (m, 1H), 1.63-1.54 (m, 2H), 1.46-1.36 (m, 1H), 1.36-1.18 (m, 3H).

m/z [M+H]$^+$=377.

EXAMPLE 57

(S)-N-((S)-1-Cyano-2-(4'-cyano-3'-(methylthio)biphenyl-4-yl)ethyl)-piperidine-2-carboxamide

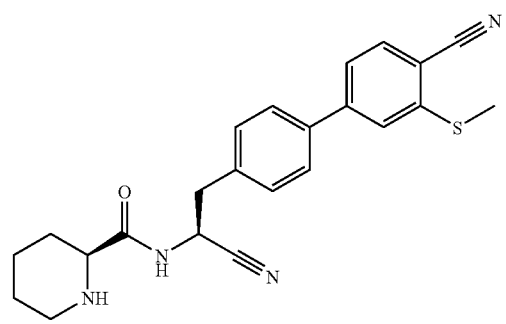

a) (S)-tert-Butyl 2-((S)-1-cyano-2-(4'-cyano-3'-(methylthio)biphenyl-4-yl)ethylcarbamoyl)-piperidine-1-carboxylate

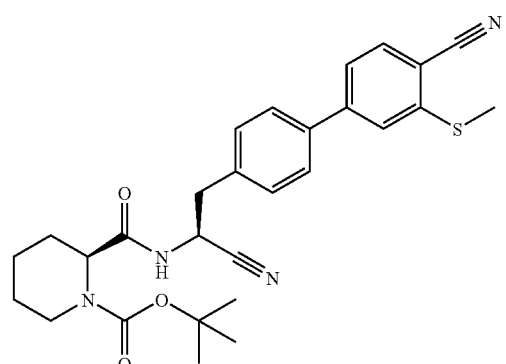

A solution of Intermediate 4 (0.250 g) and sodium methanethiolate (0.0368 g) in DMSO (1 mL) was heated in the microwave for 1 min at 100° C. The mixture was diluted with water and brine and extracted with ethyl acetate. The extracts were washed with brine then dried over sodium sulfate and evaporated to leave a foam. Purification by flash silica chromatography eluting with 30% ethyl acetate in isohexane afforded the sub-title compound as a solid (0.215 g).

m/z [M−H]$^−$=503.

b) (S)-N-((S)-1-Cyano-2-(4'-cyano-3'-(methylthio)biphenyl-4-yl)ethyl)piperidine-2-carboxamide (S)-tert-Butyl 2-((S)-1-cyano-2-(4'-cyano-3'-(methylthio)biphenyl-4-yl)ethylcarbamoyl)-piperidine-1-carboxylate was converted using a method analogous to Example 53(d) to the title compound as a colourless solid.

¹H NMR (399.826 MHz, d6-DMSO) δ 9.29 (d, J=7.2 Hz, 1H), 9.01-8.69 (m, 1H), 7.88 (d, J=7.9 Hz, 1H), 7.78 (t, J=7.8 Hz, 2H), 7.64-7.56 (m, 2H), 7.47 (d, J=8.2 Hz, 2H), 5.07 (q, J=7.4 Hz, 1H), 3.82-3.71 (m, 2H), 3.28-3.17 (m, 3H), 2.98-2.86 (m, 1H), 2.70 (s, 3H), 2.10-2.00 (m, 1H), 1.82-1.74 (m, 1H), 1.73-1.65 (m, 1H), 1.64-1.42 (m, 2H).

m/z [M+H]⁺=405.

EXAMPLE 58

(S)-N-((S)-1-Cyano-2-(4'-cyano-3'-(methylsulfonyl)biphenyl-4-yl)ethyl)piperidine-2-carboxamide

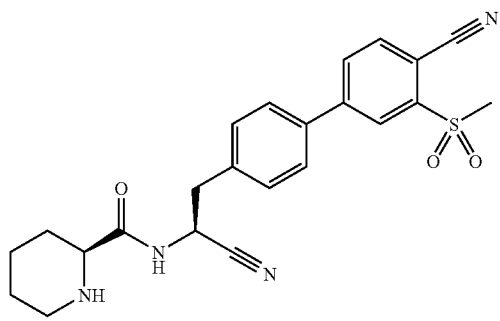

a) (S)-tert-Butyl 2-((S)-1-cyano-2-(4'-cyano-3'-(methylsulfonyl)biphenyl-4-yl)ethylcarbamoyl)piperidine-1-carboxylate

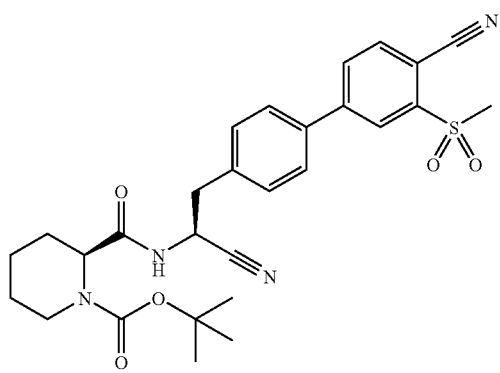

3-Chloroperoxybenzoic acid (0.151 g) was added to a solution of (S)-tert-butyl 2-((S)-1-cyano-2-(4'-cyano-3'-(methylthio)biphenyl-4-yl)ethylcarbamoyl)piperidine-1-carboxylate (0.103 g) in DCM (20 mL) at 0° C. and the mixture was stirred and allowed to warm to room temp overnight. The mixture was washed with saturated sodium bicarbonate solution, sodium metabisulfite solution, water and brine then dried over sodium sulfate, and evaporated. Purification by flash chromatography eluting with 30% ethyl acetate in isohexane afforded the subtitle compound as a colourless solid (58 mg).

¹H NMR (399.824 MHz, CDCl₃) δ 8.40 (dd, J=4.6, 1.5 Hz, 1H), 8.02-7.92 (m, 2H), 7.65 (d, J=8.5 Hz, 2H), 7.44 (d, J=8.2 Hz, 2H), 5.25-5.14 (m, 1H), 4.75-4.66 (m, 1H), 4.06-3.90 (m, 1H), 3.33 (s, 3H), 3.18 (d, J=7.2 Hz, 2H), 2.61-2.42 (m, 1H), 2.27-2.15 (m, 1H), 1.68-1.49 (m, 4H), 1.45 (s, 9H), 1.42-1.30 (m, 2H).

b) (S)-N-((S)-1-cyano-2-(4'-cyano-3'-(methylsulfonyl)biphenyl-4-yl)ethyl)piperidine-2-carboxamide Prepared using (S)-tert-butyl 2-((S)-1-cyano-2-(4'-cyano-3'-(methylsulfonyl)biphenyl-4-yl)ethylcarbamoyl)piperidine-1-carboxylate by a method analogous to Example 53(d)

¹H NMR (399.826 MHz, d6-DMSO) δ 8.52 (d, J=6.9 Hz, 1H), 8.30 (d, J=1.3 Hz, 1H), 8.27-8.20-8.20 (m, 2H), 7.82 (d, J=8.2 Hz, 2H), 7.49 (d, J=8.2 Hz, 2H), 5.09-5.01 (m, 1H), 3.46 (s, 3H), 3.27-3.16 (m, 2H), 3.10-3.03 (m, 1H), 2.82-2.75 (m, 1H), 2.48-2.42 (m, 1H), 1.61-1.54 (m, 2H), 1.45-1.37 (m, 1H), 1.37-1.17 (m, 3H).

m/z [M+H]⁺=437.

EXAMPLE 59

(S)-N-((S)-1-Cyano-2-(4'-cyano-3'-(ethylsulfonyl)biphenyl-4-yl)ethyl)piperidine-2-carboxamide

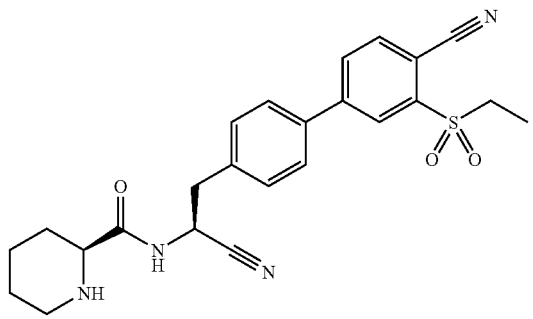

Prepared by a method analogous to Example 58.

¹H NMR (399.826 MHz, d6-DMSO) δ 8.56-8.47 (m, 1H), 8.29-8.22 (m, 3H), 7.81 (d, J=8.5 Hz, 2H), 7.49 (d, J=8.2 Hz, 2H), 5.09-5.01 (m, 1H), 3.55 (q, J=7.3 Hz, 2H), 3.28-3.16 (m, 3H), 3.09-3.04 (m, 1H), 2.81-2.74 (m, 1H), 2.31-2.18 (m, 1H), 1.57 (d, J=10.3 Hz, 2H), 1.44-1.37 (m, 1H), 1.37-1.23 (m, 2H), 1.21 (t, J=7.4 Hz, 3H).

m/z [M+H]⁺=451.

EXAMPLE 60

(S)-N-((S)-1-Cyano-2-(4'-cyano-3'-(propylsulfonyl)biphenyl-4-yl)ethyl)piperidine-2-carboxamide

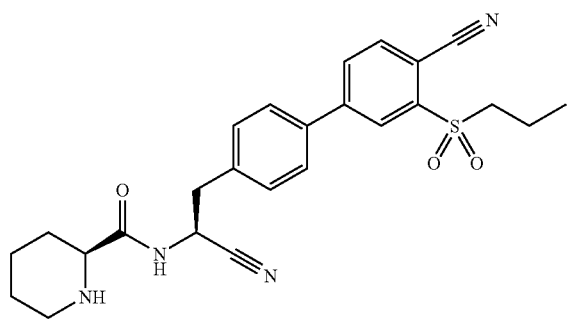

Prepared by a method analogous to Example 58.

$^1$H NMR (399.826 MHz, d6-DMSO) δ 8.63 (d, J=7.2 Hz, 1H), 8.28-8.20 (m, 4H), 7.82 (d, J=8.2 Hz, 2H), 7.50 (d, J=8.2 Hz, 2H), 5.09-5.02 (m, 1H), 3.55-3.50 (m, 2H), 3.28-3.19 (m, 3H), 3.19-3.12 (m, 1H), 2.86-2.79 (m, 1H), 1.72-1.56 (m, 4H), 1.48-1.40 (m, 1H), 1.38-1.21 (m, 3H), 0.97 (t, J=7.4 Hz, 3H).

m/z [M+H]$^+$=465.

EXAMPLE 61

(2S)-N-((1S)-2-(4'-Carbamoyl-3'-(methylsulfinyl)biphenyl-4-yl)-1-cyanoethyl)piperidine-2-carboxamide

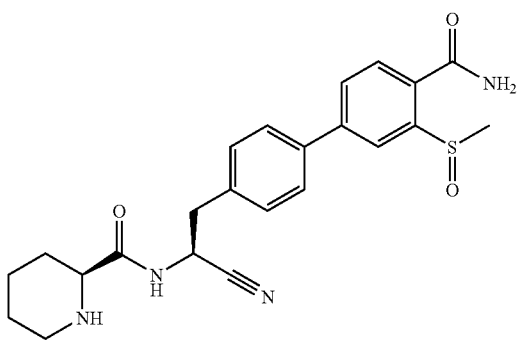

a) (2S)-tert-Butyl 2-((1S)-1-cyano-2-(4'-cyano-3'-(methylsulfinyl)biphenyl-4-yl)ethylcarbamoyl)piperidine-1-carboxylate

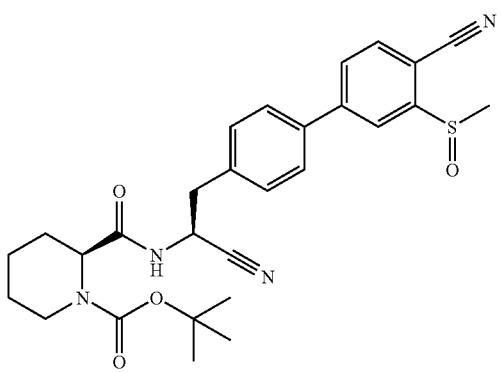

3-Chloroperoxybenzoic acid (0.137 g) was added to a solution of (S)-tert-butyl 2-((S)-1-cyano-2-(4'-cyano-3'-(methylthio)biphenyl-4-yl)ethylcarbamoyl)piperidine-1-carboxylate (0.140 g) in DCM (20 mL) at 0° C. and the mixture was stirred for 2 h then allowed to warm to RT. The mixture was washed with saturated sodium bicarbonate solution, sodium metabisulfite solution, water and brine then dried over sodium sulfate and evaporated. Purification by flash silica chromatography eluting with 30-50% ethyl acetate in isohexane afforded a colourless solid (0.08 g).

m/z [M-H]$^-$=519.

b) (2S)-N-((1S)-2-(4'-Carbamoyl-3'-(methylsulfinyl)biphenyl-4-yl)-1-cyanoethyl)piperidine-2-carboxamide A solution of (2S)-tert-butyl 2-((1S)-1-cyano-2-(4'-cyano-3'-(methylsulfinyl)biphenyl-4-yl)ethylcarbamoyl)piperidine-1-carboxylate (0.08 g) in formic acid (2 mL) was stirred and heated at 50° C. for 10 min. The mixture was evaporated and applied to a 10 g SCX column. The column was washed with methanol then eluted with 10% ammonia in methanol. The eluate was evaporated and the residue dissolved in isopropanol and precipitated with diethyl ether. The solid was collected, washed with diethyl ether and dried over magnesium sulfate. Purification by RPHPLC using aqueous 0.1% TFA afforded the major product as a colourless solid (0.027 g).

$^1$H NMR (399.826 MHz, d6-DMSO) δ 9.28 (d, J=7.2 Hz, 1H), 9.01-8.67 (m, 1H), 8.35 (t, J=1.9 Hz, 1H), 8.32 (s, 1H), 8.01 (d, J=7.9 Hz, 1H), 7.93 (d, J=7.9 Hz, 1H), 7.77 (d, J=7.7 Hz, 2H), 7.73 (s, 1H), 7.49 (d, J=8.2 Hz, 2H), 5.13-5.05 (m, 1H), 3.82-3.73 (m, 2H), 3.29-3.16 (m, 2H), 3.00-2.87 (m, 1H), 2.82 (s, 3H), 2.06 (d, J=11.5 Hz, 1H), 1.78 (d, J=11.8 Hz, 1H), 1.69 (d, J=12.6 Hz, 1H), 1.65-1.42 (m, 3H).

m/z [M+H]$^+$=439.

EXAMPLE 62

(2S)-N-((1S)-1-Cyano-2-(4'-cyano-3'-(2-methyl-1H-imidazol-1-yl)biphenyl-4-yl)ethyl)piperidine-2-carboxamide

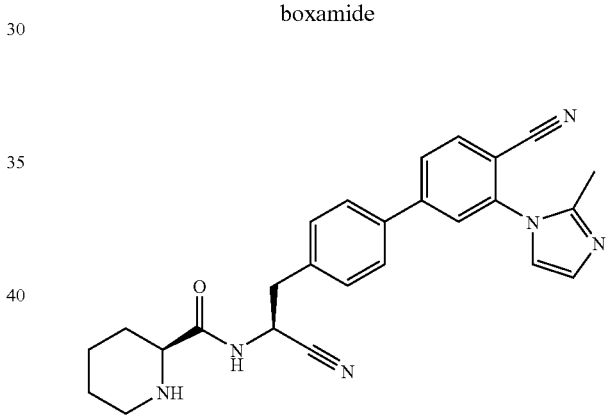

a) (2S)-tert-Butyl 2-((1S)-1-cyano-2-(4'-cyano-3'-(2-methyl-1H-imidazol-1-yl)biphenyl-4-yl)ethylcarbamoyl)piperidine-1-carboxylate

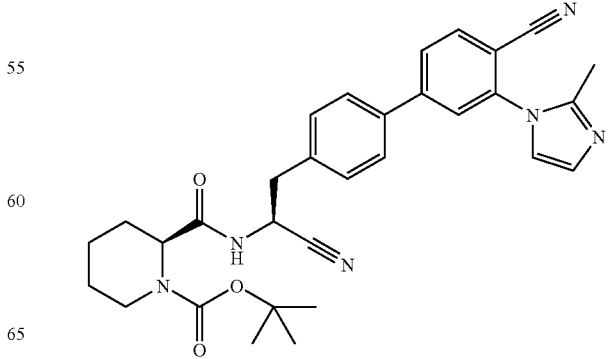

A solution of Intermediate 4 (0.1 g) and 2-methyl-1H-imidazole (0.086 g) in NMP (200 μL) was heated in the microwave for 5 min at 150° C. Heating was continued at 150° C. for 35 min. Further 2-methyl-1H-imidazole (0.02 g) was added and heating continued at 150° C. for 40 min. The mixture was concentrated in vacuo. Purification by flash silica chromatography, eluting with 80% ethyl acetate in isohexane, afforded the subtitle compound as a solid (0.116 g).
m/z [M+H]$^+$=539.

b) (2S)-N-((1S)-1-Cyano-2-(4'-cyano-3'-(2-methyl-1H-imidazol-1-yl)biphenyl-4-yl)ethyl)piperidine-2-carboxamide Prepared using (2S)-tert-butyl 2-((1S)-1-cyano-2-(4'-cyano-3'-(2-methyl-1H-imidazol-1-yl)biphenyl-4-yl)ethylcarbamoyl)piperidine-1-carboxylate by a method analogous to Example 53(d).
$^1$H NMR (399.826 MHz, d6-DMSO) δ 9.47-9.32 (m, 1H), 9.07-8.64 (m, 1H), 8.31-8.24 (m, 2H), 8.22-8.16 (m, 1H), 8.01 (s, 1H), 7.89-7.81 (m, 2H), 7.78 (s, 1H), 7.55-7.47 (m, 2H), 5.18-5.03 (m, 1H), 3.86-3.73 (m, 1H), 3.31-3.10 (m, 3H), 2.98-2.84 (m, 1H), 2.54 (s, 3H), 2.09-1.89 (m, 1H), 1.81-1.37 (m, 5H).
m/z [M+H]$^+$=439.

EXAMPLE 63

(S)-N-((S)-1-cyano-2-(3'-cyano-4'-(methylthio)biphenyl-4-yl)ethyl)piperidine-2-carboxamide

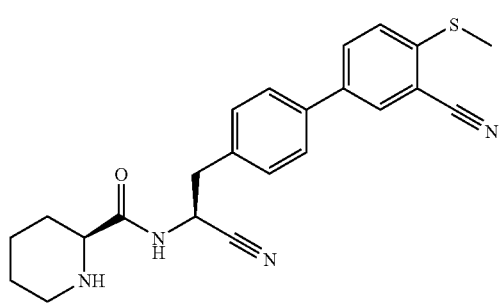

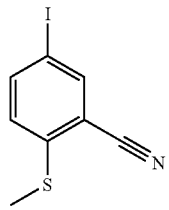

Sodium thiomethoxide (0.142 g) was added to a solution of 2-fluoro-5-iodobenzonitrile (0.5 g) in DMSO (1 mL) and the mixture stirred. An exotherm was noted. After stirring for 90 min, water was added and the solid that precipitated was collected, washed with water and dried at 50° C. under vacuum to leave the subtitle compound as an off-white solid (0.52 g).

$^1$H NMR (399.826 MHz, d6-DMSO) δ 8.16 (d, J=2.1 Hz, 1H), 7.99 (dd, J=8.6, 1.9 Hz, 1H), 7.25 (d, J=8.5 Hz, 1H), 2.57 (s, 3H).

b) (S)-N-((S)-1-Cyano-2-(3'-cyano-4'-(methylthio)biphenyl-4-yl)ethyl)piperidine-2-carboxamide Prepared using 5-iodo-2-(methylthio)benzonitrile by a method analogous to Example 53. $^1$H NMR (399.826 MHz, d6-DMSO) δ 8.51 (d, J=7.9 Hz, 1H), 8.12 (d, J=2.1 Hz, 1H), 7.98 (dd, J=8.5, 2.1 Hz, 1H), 7.71 (d, J=8.2 Hz, 2H), 7.55 (d, J=8.5 Hz, 1H), 7.40 (d, J=8.2 Hz, 2H), 5.06-4.97 (m, 1H), 3.24-3.12 (m, 2H), 3.10-3.02 (m, 1H), 2.79 (d, J=12.6 Hz, 1H), 2.63 (s, 3H), 2.47-2.42 (m, 1H), 1.59 (d, J=10.3 Hz, 2H), 1.42 (d, J=10.8 Hz, 1H), 1.36-1.17 (m, 3H).
m/z [M+H]$^+$=405.

EXAMPLE 64

(S)-N-((S)-1-Cyano-2-(3'-cyano-4'-(methylsulfonyl)biphenyl-4-yl)ethyl)piperidine-2-carboxamide

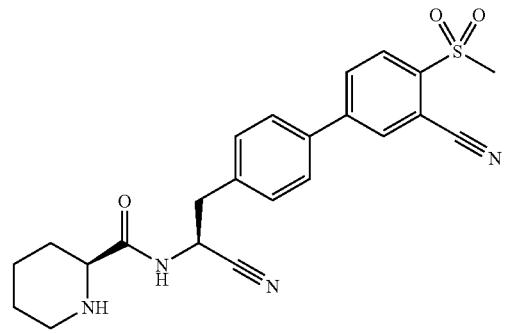

a) 5-Iodo-2-(methylsulfonyl)benzonitrile

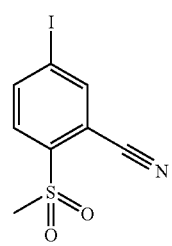

A solution of 5-iodo-2-(methylthio)benzonitrile (0.3 g) in DCM (10 mL) at 0° C. was treated with 3-chloroperoxybenzoic acid (0.733 g) and the mixture stirred overnight at RT. The mixture was diluted with DCM and washed with saturated sodium bicarbonate solution, sodium metabisulphite solution, water and brine then dried over sodium sulfate and evaporated to leave the subtitle compound as a colourless solid (0.27 g).

$^1$H NMR (399.824 MHz, CDCl$_3$) δ 8.23 (d, J=1.5 Hz, 1H), 8.18 (dd, J=8.3, 1.7 Hz, 1H), 7.89 (d, J=8.2 Hz, 1H), 3.27 (s, 3H).

b) (S)-N-((S)-1-Cyano-2-(3'-cyano-4'-(methylsulfonyl)biphenyl-4-yl)ethyl)piperidine-2-carboxamide Prepared using 5-iodo-2-(methylsulfonyl)benzonitrile by a method analogous to Example 53.

$^1$H NMR (399.826 MHz, d6-DMSO) δ 8.57-8.52 (m, 1H), 8.51 (d, J=1.8 Hz, 1H), 8.28 (dd, J=8.3, 1.9 Hz, 1H), 8.17 (d, J=8.2 Hz, 1H), 7.84 (d, J=8.2 Hz, 2H), 7.48 (d, J=8.2 Hz, 2H), 5.09-5.01 (m, 1H), 3.42 (s, 3H), 3.25-3.18 (m, 2H), 3.11-3.05 (m, 1H), 2.82-2.75 (m, 1H), 2.48-2.43 (m, 1H), 1.63-1.55 (m, 2H), 1.46-1.37 (m, 1H), 1.37-1.18 (m, 3H).

m/z [M+H]$^+$=437,

EXAMPLE 65

(S)-tert-Butyl 2-((S)-1-cyano-2-(3'-cyano-4'-(propylsulfonyl)biphenyl-4-yl)ethylcarbamoyl)piperidine-1-carboxylate a) 5-Iodo-2-(propylthio)benzonitrile

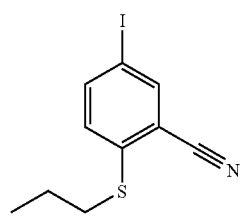

Prepared by the method of Example 63(a).

$^1$H NMR (399.824 MHz, CDCl$_3$) δ 7.88 (d, J=2.1 Hz, 1H), 7.78 (dd, J=8.5, 1.8 Hz, 1H), 7.11 (d, J=8.5 Hz, 1H), 3.00-2.95 (m, 2H), 1.76-1.66 (m, 2H), 1.06 (t, J=7.4 Hz, 3H).

b) (S)-tert-Butyl 2-((S)-1-amino-3-(3'-cyano-4'-(propylthio)biphenyl-4-yl)-1-oxopropan-2-ylcarbamoyl)piperidine-1-carboxylate

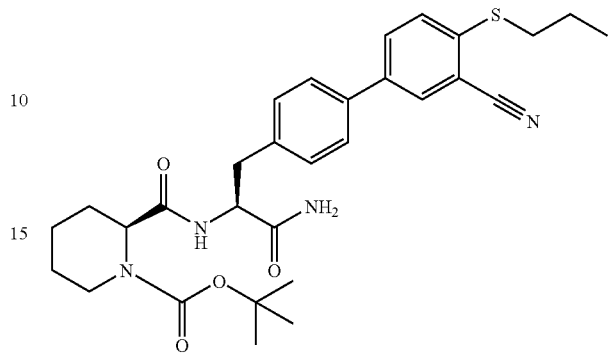

Prepared by the method of Example 53(b).
m/z [M−H]$^−$=549.

c) (S)-tert-Butyl 2-((S)-1-cyano-2-(3'-cyano-4'-(propylthio)biphenyl-4-yl)ethylcarbamoyl)piperidine-1-carboxylate

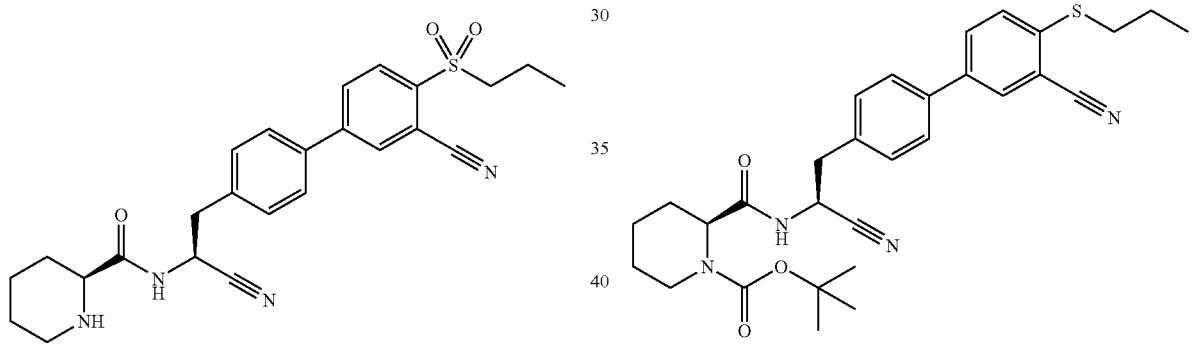

Prepared by the method of Example 53(c).
m/z[M−H]$^−$=531.

d) (S)-tert-Butyl 2-((S)-1-cyano-2-(3'-cyano-4'-(propylsulfonyl)biphenyl-4-yl)ethylcarbamoyl)piperidine-1-carboxylate

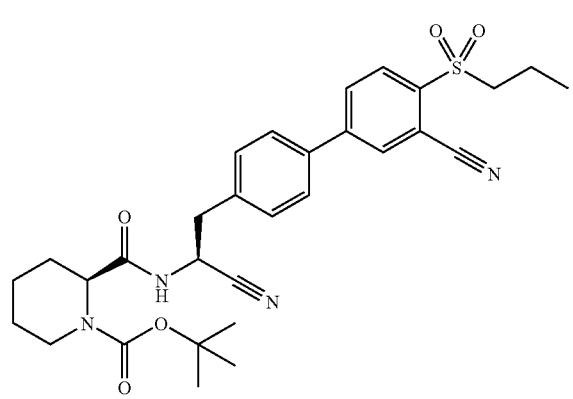

3-Chloroperoxybenzoic acid (0.171 g) was added to a solution of (S)-tert-butyl 2-((S)-1-cyano-2-(3'-cyano-4'-(propylthio)biphenyl-4-yl)ethylcarbamoyl)piperidine-1-carboxylate) (0.123 g) in DCM (5 mL) stirred in an ice bath. After 1 h the mixture was warmed to RT and stirred overnight. The solution was washed with saturated sodium bicarbonate solution, sodium metabisulphite solution and brine then dried over sodium sulfate and evaporated. Purification by flash silica chromatography, eluting with 30% ethyl acetate in isohexane afforded the subtitle compound as a colourless film (101 mg).

m/z [M−H]⁻=563.

e) (S)-tert-butyl 2-((S)-1-cyano-2-(3'-cyano-4'-(propylsulfonyl)biphenyl-4-yl)ethylcarbamoyl)piperidine-1-carboxylate Prepared by the method of Example 53(d).

$^1$H NMR (399.826 MHz, d6-DMSO) δ 8.60 (s, 1H), 8.51 (d, J=1.5 Hz, 1H), 8.28 (dd, J=8.2, 1.8 Hz, 1H), 8.14 (d, J=8.5 Hz, 1H), 7.85 (d, J=8.2 Hz, 2H), 7.48 (d, J=7.9 Hz, 2H), 5.09-5.00 (m, 1H), 3.48 (t, J=7.7 Hz, 2H), 3.25-3.18 (m, 3H), 3.13 (d, J=8.7 Hz, 1H), 2.83 (d, J=12.6 Hz, 1H), 1.72-1.56 (m, 4H), 1.49-1.39 (m, 1H), 1.36-1.21 (m, 3H), 0.97 (t, J=7.4 Hz, 3H).

m/z [M+H]⁺=465.

TABLE 2

Further examples prepared according to the method of Example 53.

| Ex. | Name | Structure | NMR | m/z [M + H]⁺ |
|---|---|---|---|---|
| 66 | (S)-N-((S)-1-Cyano-2-(4-(3-methyl-2-oxo-2,3-dihydrobenzo[d]thiazol-5-yl)phenyl)ethyl)piperidine-2-carboxamide | 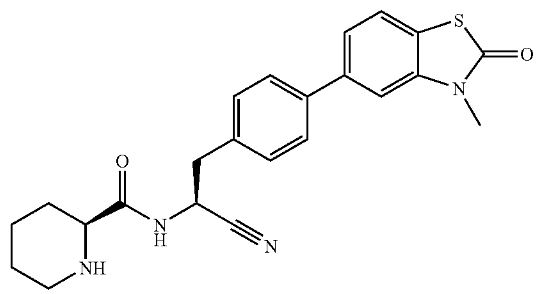 | $^1$H NMR (399.826 MHz, d6-DMSO) δ 8.60-8.49 (m, 1 H), 7.76-7.70(m, 3 H), 7.57(d, J = 1.5 Hz, 1 H), 7.51(dd, J = 8.2, 1.5 Hz, 1 H), 7.42(d, J = 8.2 Hz, 2 H), 5.06-4.97 (m, 1 H), 3.49(s, 3 H), 3.22-3.15(m, 2 H), 3.14-3.08(m, 1 H), 2.85-2.78(m, 1 H), 1.66-1.56 (m, 2 H), 1.47-1.39(m, 1 H), 1.36-1.20(m, 4 H) | 421 |
| 67 | (2S)-N-{(1S)-1-cyano-2-[4-(1,1-dioxido-2,3-dihydro-1,2-benzisothiazol-5-yl)phenyl]ethyl}piperidine-2-carboxamide | 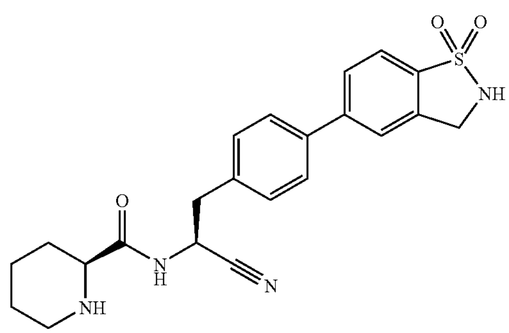 | $^1$H NMR (399.826 MHz, d6-DMSO) δ 8.52(d, J = 7.7 Hz, 1 H), 7.90-7.79 (m, 4 H), 7.70(d, J = 8.5 Hz, 2 H), 7.44(d, J = 8.2 Hz, 2 H), 5.07-4.99(m, 1 H), 4.45(s, 2 H), 3.29 (s, 1 H), 3.25-3.14(m, 2 H), 3.10-3.06(m, 1 H), 2.82-2.75(m, 1 H), 1.59 (d, J = 11.5 Hz, 2 H), 1.46-1.37(m, 1 ), 1.37-1.19(m, 3 H) | 425 |
| 68 | (S)-N-((S)-1-Cyano-2-(4-(3-oxo-3,4-dihydro-2H-benzo[b][1,4]thiazin-7-yl)phenyl)ethyl)piperidine-2-carboxamide | 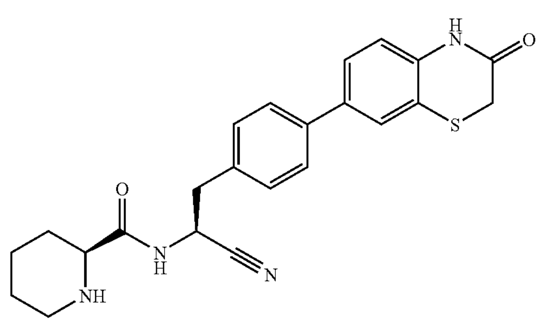 | $^1$H NMR (399.826 MHz, d6-DMSO) δ 10.65(s, 1 H), 9.30(d, J = 7.2 Hz, 1 H), 9.03-8.67(m, 1 H), 7.64-7.60(m, 3 H), 7.49 (dd, J = 8.5, 2.1 Hz, 1 H), 7.38(d, J = 8.2 Hz, 2 H), 7.05(d, J = 8.5 Hz, 1 H), 5.03(q, J = 7.4 Hz, 1 H), 3.81-3.72(m, 1 H), 3.50 (s, 2 H), 3.25-3.13(m, 4 H), 2.98-2.86(m, 1 H), 2.09-2.01(m, 1 H), 1.81-1.74(m, 1 H), 1.73-1.65(m, 1 H), 1.64-1.53 (m, 1 H), 1.52-1.43(m, 1 H) | 421 |

TABLE 2-continued

Further examples prepared according to the method of Example 53.

| Ex. | Name | Structure | NMR | m/z [M + H]+ |
|---|---|---|---|---|
| 69 | 2S)-N-{(1S)-1-Cyano-2-[4-(2-methyl-1,1-dioxido-2,3-dihydro-1,2-benzisothiazol-5-yl)phenyl]ethyl} piperidine-2-carboxamide | 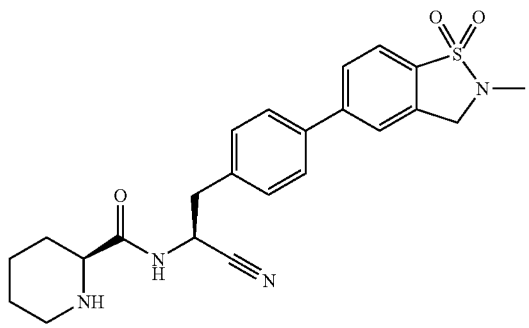 | $^1$H NMR (399.826 MHz, d6-DMSO) δ 8.52(d, J = 8.1 Hz, 1 H), 7.93(d, J = 7.9 Hz, 1 H), 7.89-7.84 (m, 2 H), 7.71(d, J = 8.2 Hz, 2 H), 7.44(d, J = 8.2 Hz, 2 H), 5.03(q, J = 6.9 Hz, 1 H), 4.45(s, 2 H), 3.25-3.15(m, 2 H), 3.11-3.05(m, 1 H), 2.84(s, 3 H), 2.82-2.75(m, 1 H), 2.48-2.43(m, 1 H), 1.63-1.54(m, 2 H), 1.45-1.38(m, 1 H), 1.37-1.18 (m, 3 H) | 439 |

EXAMPLE 70
(S)-N-((S)-1-Cyano-2-(4'-ethylbiphenyl-4-yl)ethyl) piperidine-2-carboxamide Trifluoroacetate

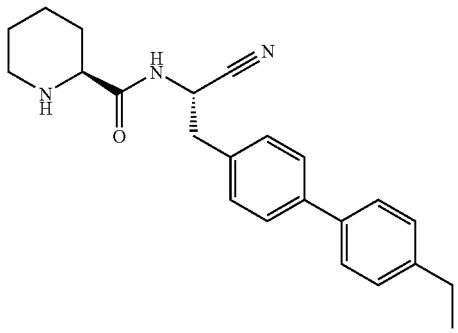

Prepared by a process analogous to that described in Method 2 Example 2 using (S)-tert-butyl 2-((S)-1-cyano-2-(4-iodophenyl)ethylcarbamoyl)piperidine-1-carboxylate and 4-ethylphenylboronic acid.

$^1$H NMR (399.826 MHz, d6-DMSO) δ 8.58-8.48 (m, 2H), 7.61-7.55 (m, 4H), 7.36 (d, J=8.2 Hz, 2H), 7.29 (d, J=8.2 Hz, 2H), 5.04-4.94 (m, 1H), 3.21-3.12 (m, 2H), 3.08 (dd, J=9.2, 2.6 Hz, 2H), 2.82-2.76 (m, 1H), 2.64 (q, J=7.6 Hz, 2H), 2.53-2.44 (m, 1H), 1.66-1.55 (m, 2H), 1.45-1.38 (m, 1H), 1.34-1.18 (m, 6H).

m/z 362 [M+H]+

EXAMPLE 71
(S)-N-((S)-1-Cyano-2-(4'-(N-methylsulfamoyl)biphenyl-4-yl)ethyl)piperidine-2-carboxamide Trifluoroacetate

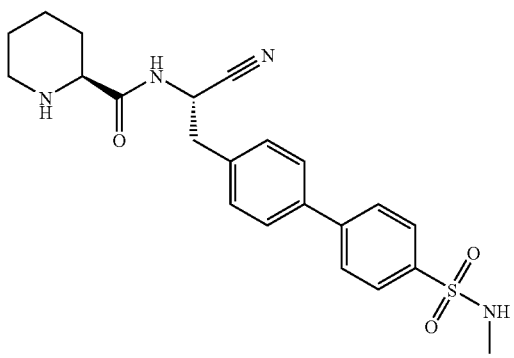

Prepared by a process analogous to that described in Method 2 Example 2 using (S)-tert-butyl 2-((S)-1-cyano-2-(4-iodophenyl)ethylcarbamoyl)piperidine-1-carboxylate and 4-(N-methylsulfamoyl)phenylboronic acid.

$^1$H NMR (399.826 MHz, d6-DMSO) δ 9.32 (d, J=7.2 Hz, 1H), 9.02-8.94 (m, 1H), 8.80-8.71 (m, 1H), 7.90 (dd, J=6.7, 2.1 Hz, 2H), 7.85 (dd, J=6.7, 2.1 Hz, 2H), 7.74 (d, J=8.5 Hz, 2H), 7.53-7.45 (m, 3H), 5.10-5.04 (m, 1H), 3.81-3.74 (m, 1H), 3.25-3.19 (m, 3H), 2.97-2.87 (m, 1H), 2.45 (d, J=4.9 Hz, 3H), 2.08-2.02 (m, 1H), 1.80-1.74 (m, 1H), 1.72-1.66 (m, 1H), 1.62-1.44 (m, 3H).

m/z 427 [M+H]+

EXAMPLE 72
(S)-N-((S)-2-(4'-(Azetidin-1-ylsulfonyl)biphenyl-4-yl)-1-cyanoethyl)piperidine-2-carboxamide Trifluoroacetate

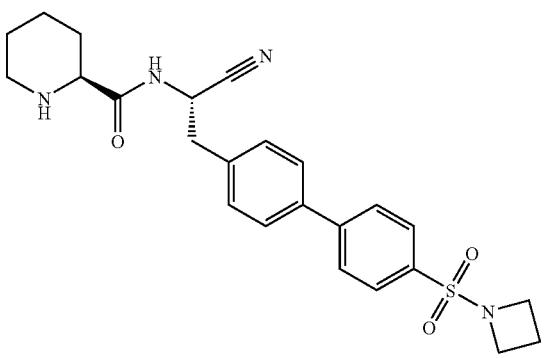

Prepared by a process analogous to that described in Method 2 Example 2 using (S)-tert-butyl 2-((S)-1-cyano-2-(4-iodophenyl)ethylcarbamoyl)piperidine-1-carboxylate and 4-(N-methylsulfamoyl)phenylboronic acid.

$^1$H NMR (399.826 MHz, d6-DMSO) δ 9.31 (d, J=7.2 Hz, 1H), 9.01-8.92 (m, 1H), 8.81-8.70 (m, 1H), 7.99 (dd, J=6.7, 1.8 Hz, 2H), 7.88 (d, J=8.5 Hz, 22H), 7.78 (d, J=8.2 Hz, 2H), 7.48 (d, J=8.2 Hz, 2H), 5.11-5.04 (m, 1H), 3.82-3.67 (m, 5H), 3.25-3.19 (m, 3H), 2.97-2.86 (m, 1H), 2.08-1.97 (m, 3H), 1.80-1.43 (m, 5H).

m/z 453 [M+H]+

EXAMPLE 73

(S)-N-((S)-1-Cyano-2-(4'-(N-(2-hydroxyethyl)sulfamoyl)biphenyl-4-yl)ethyl)piperidine-2-carboxamide

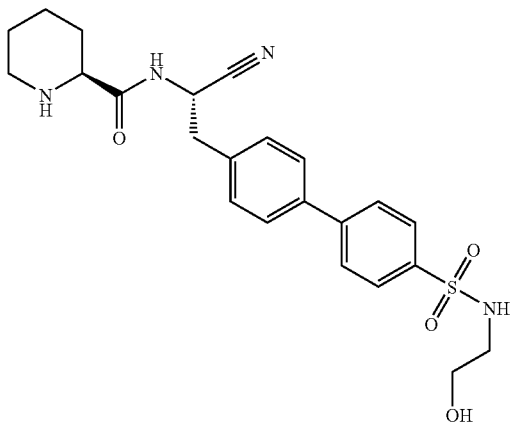

(S)-tert-Butyl 2-((S)-1-cyano-2-(4-iodophenyl)ethylcarbamoyl)piperidine-1-carboxylate (0.15 g) and bis[1,2-bis(diphenylphosphino)ethane]palladium (0) (2.80 mg, 3.10 μmol) were added to dioxane (3 mL) and 4-(N-(2-(tert-butyldimethylsilyloxy)ethyl)sulfamoyl)-phenylboronic acid (0.167 g) was added to the mixture which was then stirred, under nitrogen, for 10 min. Potassium carbonate (2M solution) (0.310 mL) was added and the reaction mixture was heated at 75° C. for 3 h. The reaction mixture was poured onto a Isolute HM-N cartridge and product was eluted with DCM. Solvent was removed in vacuo and the residue was dissolved in THF (5 mL). The resulting solution was cooled in an ice-bath and TBAF (1M solution in THF, 0.626 mL) was added and stirring was continued for 2 h. The reaction mixture was concentrated in vacuo and dissolved in formic acid (5 mL). The resulting solution was heated at 50° C. for 10 min. The reaction mixture was concentrated in vacuo, dissolved in methanol and loaded onto an SCX cartridge. Non-basic impurities were washed off with methanol then the desired compound was eluted with 10% ammonia in methanol. Solvent was removed in vacuo to give the title compound (0.025 g).

$^1$H NMR (399.826 MHz, d6-DMSO) δ 8.81-8.73 (m, 1H), 7.90-7.84 (m, 4H), 7.72 (d, J=208.5 Hz, 2H), 7.65 (t, J=5.9 Hz, 1H), 7.44 (d, J=8.2 Hz, 2H), 5.08-5.01 (m, 1H), 4.72-4.67 (m, 1H), 3.41-3.15 (m, 6H), 2.92 (d, J=11.8 Hz, 1H), 2.82 (q, J=6.2 Hz, 2H), 2.68-2.58 (m, 1H), 1.77-1.71 (m, 1H), 1.67-1.62 (m, 1H), 1.53-1.48 (m, 1H), 1.40-1.30 (m, 3H).

m/z 457 [M+H]$^+$

EXAMPLE 74

(S)-N-((S)-1-Cyano-2-(4'-(methylcarbamoyl)biphenyl-4-yl)ethyl)piperidine-2-carboxamide Trifluoroacetate

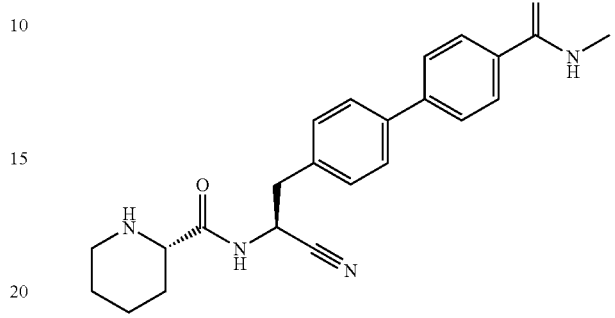

4'-((S)-2-((S)-1-(tert-Butoxycarbonyl)piperidine-2-carboxamido)-2-cyanoethyl)biphenyl-4-carboxylic acid (0.08 g), methylamine hydrochloride (0.011 g) and triethylamine (0.140 mL) in DMF (3 mL) were stirred under nitrogen at 0° C. 2,4,6-Tripropyl-1,3,5,2,4,6-trioxatriphosorinan-2,4,6-trioxide (0.128 g) was added and stirring at room temperature continued overnight. The mixture was diluted with ethyl acetate, washed with water then brine, dried over magnesium sulfate, filtered and concentrated in vacuo. The crude product was dissolved in formic acid (3 mL) and the solution was heated at 50° C. for 0.5 h. The reaction mixture was concentrated in vacuo and the crude product was purified by preparative HPLC on a Sunfire column using a 95-5% gradient of aqueous 0.1% TFA in acetonitrile as eluent. The fractions containing the desired compound were evaporated to dryness to afford the title compound (0.012 g) as a white solid.

$^1$H NMR (399.826 MHz, d6-DMSO) δ 9.28 (d, J=7.2 Hz, 1H), 9.00-8.90 (m, 1H), 8.81-8.69 (m, 1H), 8.50-8.45 (m, 1H), 7.93 (d, J=8.5 Hz, 2H), 7.79-7.69 (m, 4H), 7.44 (d, J=8.2 Hz, 2H), 5.10-5.03 (m, 1H), 3.81-3.73 (m, 1H), 3.25-3.17 (m, 3H), 2.98-2.87 (m, 1H), 2.80 (d, J=4.4 Hz, 3H), 2.09-2.03 (m, 1H), 1.81-1.74 (m, 1H), 1.72-1.66 (m, 1H), 1.64-1.42 (m, 3H).

m/z 391 [M+H]$^+$

EXAMPLE 75

(S)-N-((S)-1-Cyano-2-(4'-(pyrrolidine-1-carbonyl)biphenyl-4-yl)ethyl)piperidine-2-carboxamide Trifluoroacetate

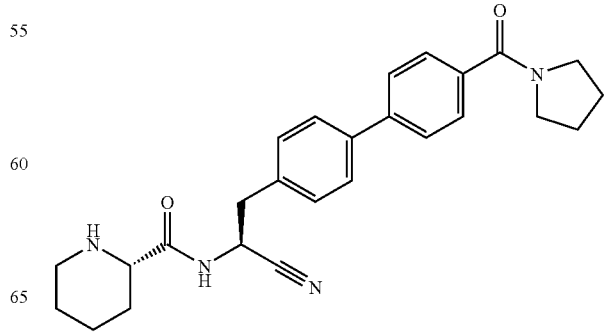

Prepared by a process analogous to that described in Example 74 using 4'-((S)-2-((S)-1-(tert-butoxycarbonyl)piperidine-2-carboxamido)-2-cyanoethyl)biphenyl-4-carboxylic acid, 2,4,6-tripropyl-1,3,5,2,4,6-trioxatriphosorinan-2,4,6-trioxide, triethylamine and pyrrolidine.

$^1$H NMR (399.826 MHz, d6-DMSO) δ 9.27 (d, J=7.2 Hz, 1H), 9.00-8.87 (m, 1H), 8.80-8.69 (m, 1H), 7.74-7.68 (m, 4H), 7.61 (d, J=8.5 Hz, 2H), 7.43 (d, J=8.2 Hz, 2H), 5.09-5.03 (m, 1H), 3.80-3.41 (m, 5H), 3.25-3.18 (m, 3H), 2.98-2.86 (m, 1H), 2.08-2.02 (m, 1H), 1.91-1.46 (m, 9H).

m/z 431 [M+H]$^+$

EXAMPLE 76

(S)-N-((S)-1-Cyano-2-(4'-(4-methylpiperazine-1-carbonyl)biphenyl-4-yl)ethyl)piperidine-2-carboxamide Trifluoroacetate

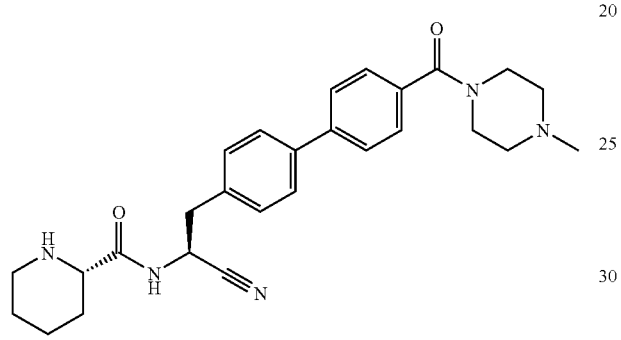

Prepared by a process analogous to that described in Example 74 using 4'-((S)-2-((S)-1-(tert-butoxycarbonyl)piperidine-2-carboxamido)-2-cyanoethyl)biphenyl-4-carboxylic acid, 2,4,6-tripropyl-1,3,5,2,4,6-trioxatriphosorinan-2,4,6-trioxide, triethylamine and 1-methylpiperazine.

$^1$H NMR (399.826 MHz, d6-DMSO) δ 9.32 (d, J=7.2 Hz, 1H), 9.04-8.95 (m, 1H), 8.83-8.70 (m, 1H), 7.78 (d, J=8.2 Hz, 2H), 7.71 (d, J=8.2 Hz, 2H), 7.56 (d, J=8.2 Hz, 2H), 7.45 (d, J=8.2 Hz, 2H), 5.09-5.02 (m, 1H), 3.82-3.74 (m, 1H), 3.26-3.06 (m, 8H), 2.99-2.87 (m, 1H), 2.83 (s, 3H), 2.09-2.03 (m, 1H), 1.81-1.43 (m, 8H).

m/z 460 [M+H]$^+$

EXAMPLE 77

(S)-N-((S)-1-Cyano-2-(6-(4-cyanophenyl)pyridin-3-yl)ethyl)piperidine-2-carboxamide Trifluoroacetate

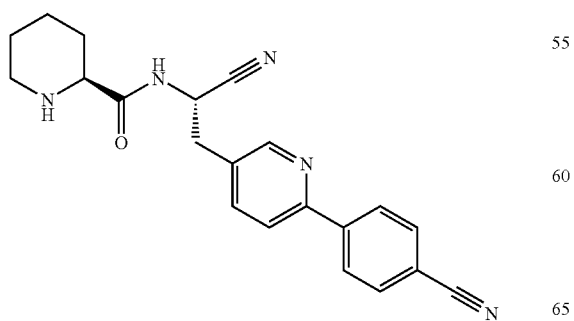

Prepared by a process analogous to that described in Method 2 Example 2 using (S)-tert-butyl 2-((S)-2-(6-bromopyridin-3-yl)-1-cyanoethylcarbamoyl)piperidine-1-carboxylate (Intermediate 5) and 4-cyanophenylboronic acid.

$^1$H NMR (399.826 MHz, d6-DMSO) δ 9.31 (d, J=7.4 Hz, 1H), 8.98-8.84 (m, 1H), 8.80-8.64 (m, 2H), 8.32-8.26 (m, 2H), 8.11 (d, J=8.5 Hz, 1H), 7.97 (d, J=8.5 Hz, 2H), 7.92 (dd, J=8.2, 2.1 Hz, 1H), 5.20-5.14 (m, 1H), 3.82-3.74 (m, 1H), 3.29-3.16 (m, 3H), 2.97-2.85 (m, 1H), 2.08-2.01 (m, 1H), 1.80-1.39 (m, 5H).

m/z 360 [M+H]$^+$

EXAMPLE 78

(S)-N-((S)-1-Cyano-2-(6-(3-cyanophenyl)pyridin-3-yl)ethyl)piperidine-2-carboxamide Trifluoroacetate

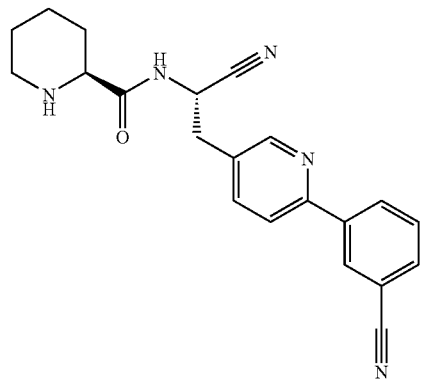

Prepared by a process analogous to that described in Method 2 Example 2 using (S)-tert-butyl 2-((S)-2-(6-bromopyridin-3-yl)-1-cyanoethylcarbamoyl)piperidine-1-carboxylate and 3-cyanophenylboronic acid.

$^1$H NMR (399.826 MHz, d6-DMSO) δ 9.32 (d, J=7.2 Hz, 1H), 8.99-8.84 (m, 1H), 8.81-8.67 (m, 1H), 8.63 (s, 1H), 8.52 (d, J=1.5 Hz, 1H), 8.45 (dt, J=8.1, 1.4 Hz, 1H), 8.11 (d, J=8.2 Hz, 1H), 7.92 (dd, J=8.3, 1.9 Hz, 2H), 7.72 (t, J=7.9 Hz, 1H), 5.20-5.13 (m, 1H), 3.83-3.74 (m, 1H), 3.28-3.16 (m, 3H), 2.97-2.85 (m, 1H), 2.08-2.01 (m, 1H), 1.80-1.40 (m, 5H).

m/z 360 [M+H]$^+$

EXAMPLE 79

(S)-N-((S)-1-Cyano-2-(6-(2-hydroxyphenyl)pyridin-3-yl)ethyl)piperidine-2-carboxamide

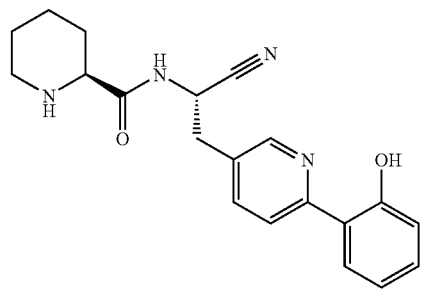

Prepared by a process analogous to that described in Method 2 Example 2 using (S)-tert-butyl 2-((S)-2-(6-bromopyridin-3-yl)-1-cyanoethylcarbamoyl)piperidine-1-carboxylate and 2-hydroxyphenylboronic acid.

¹H NMR (399.826 MHz, d6-DMSO) δ 8.62-8.54 (m, 1H), 8.52 (d, J=2.1 Hz, 1H), 8.18 (d, J=8.7 Hz, 1H), 8.02-7.93 (m, 2H), 7.30 (dd, J=15.4, 1.5 Hz, 1H), 6.94-6.89 (m, 2H), 5.17-5.09 (m, 1H), 3.25 (d, J=7.9 Hz, 1H), 3.05 (dd, J=9.5, 2.8 Hz, 1H), 2.79-2.74 (m, 1H), 2.54-2.43 (m, 5H), 1.57-1.49 (m, 1H), 1.43-1.37 (m, 1H), 1.32-1.14 (m, 3H).

m/z 351 [M+H]⁺

EXAMPLE 80

(S)-N-((S)-1-Cyano-2-(6-(4-(N,N-dimethylsulfamoyl)phenyl)pyridin-3-yl)ethyl)piperidine-2-carboxamide Trifluoroacetate

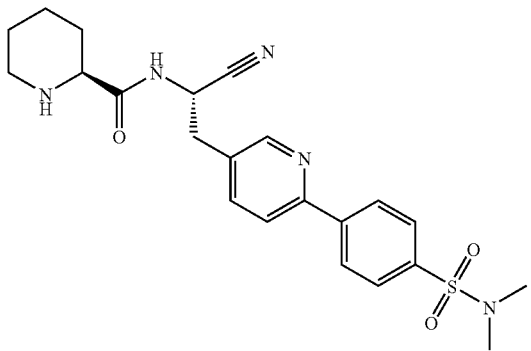

Prepared by a process analogous to that described in Method 2 Example 2 using (S)-tert-butyl 2-((S)-2-(6-bromopyridin-3-yl)-1-cyanoethylcarbamoyl)piperidine-1-carboxylate and N,N-dimethyl-4-(4,4,5,5-tetramethyl-1,3,2-dioxaborolan-2-yl)benzenesulfonamide.

¹H NMR (399.826 MHz, d6-DMSO) δ 9.31 (d, J=7.4 Hz, 1H), 8.95-8.82 (m, 1H), 8.78-8.62 (m, 2H), 8.37-8.30 (m, 2H), 8.12-8.06 (m, 1H), 7.92 (dd, J=14.9, 2.3 Hz, 1H), 7.86 (d, J=7.7 Hz, 2H), 5.26-5.14 (m, 1H), 3.33-3.15 (m, 3H), 2.97-2.84 (m, 1H), 2.68-2.63 (m, 6H), 2.07-2.01 (m, 1H), 1.80-1.74 (m, 1H), 1.73-1.40 (m, 5H).

m/z 442 [M+H]⁺

EXAMPLE 81

(S)-N-((S)-2-(6-(3-Chloro-5-(dimethylcarbamoyl)phenyl)pyridin-3-yl)-1-cyanoethyl)piperidine-2-carboxamide Trifluoroacetate

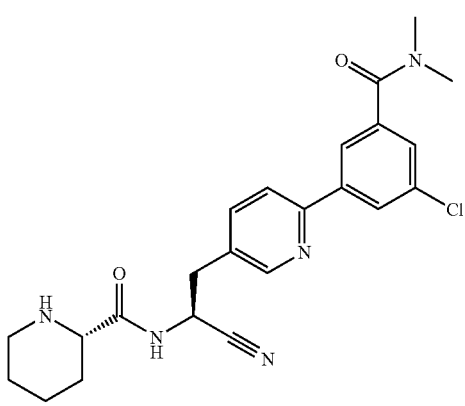

Prepared by a process analogous to that described in Method 2 Example 2 using (S)-tert-butyl 2-((S)-2-(6-bromopyridin-3-yl)-1-cyanoethylcarbamoyl)piperidine-1-carboxylate and 3-chloro-5-(dimethylcarbamoyl)phenylboronic acid. Product isolated as a 7:3 mixture of diastereomers at the aminonitrile methine.

¹H NMR (299.947 MHz, d6-DMSO) δ 9.37 (d, J=8.1 Hz, 0.3H), 9.28 (d, J=7.3 Hz, 0.7H), 8.95-8.66 (m, 2H), 8.62 (s, 1H), 8.23-8.18 (m, 1H), 8.15-8.04 (m, 2H), 7.93-7.85 (m, 1H), 7.54 (s, 1H), 5.27-5.11 (m, 1H), 3.86-3.70 (m, 2H), 3.31-3.12 (m, 3H), 3.02 (s, 3H), 2.93 (s, 3H), 2.09-1.86 (m, 1H), 1.82-1.38 (m, 4H), 1.31-1.20 (m, 1H).

m/z [M+H]+=440, 442; [M−H]−=438, 440.

EXAMPLE 82

(S)-N-((S)-1-Cyano-2-(4'-(trifluoromethyl)biphenyl-4-yl)ethyl)piperidine-2-carboxamide Trifluoroacetate

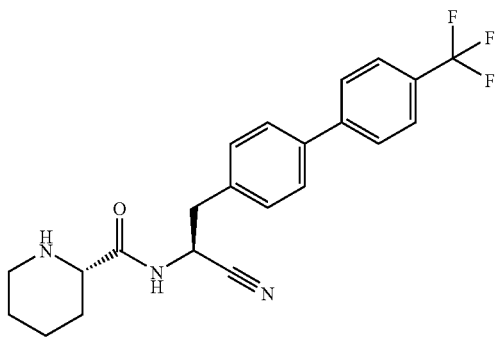

Prepared by a process analogous to that described in Method 2 Example 2 using (S)-tert-butyl 2-((S)-1-cyano-2-(4-iodophenyl)ethylcarbamoyl)piperidine-1-carboxylate and 4-(trifluoromethyl)phenylboronic acid.

¹H NMR (399.826 MHz, d6-DMSO) δ 9.29 (d, J=7.2 Hz, 1H), 8.98-8.89 (m, 1H), 8.80-8.70 (m, 1H), 7.90 (d, J=8.2 Hz, 2H), 7.82 (d, J=8.5 Hz, 2H), 7.74 (d, J=8.2 Hz, 2H), 7.47 (d, J=8.5 Hz, 2H), 5.07 (q, J=7.5 Hz, 1H), 3.82-3.72 (m, 2H), 3.25-3.15 (m, 2H), 2.99-2.86 (m, 1H), 2.09-2.01 (m, 1H), 1.81-1.38 (m, 5H).

m/z [M+H]+=402; [M−H]−=400.

EXAMPLE 83

(S)-N-((S)-1-Cyano-2-(3'-(piperidine-1-carbonyl)biphenyl-4-yl)ethyl)piperidine-2-carboxamide Trifluoroacetate

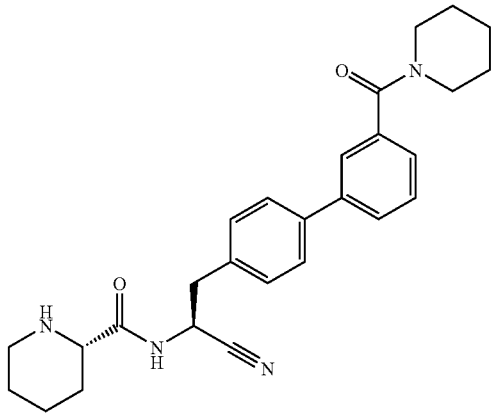

Prepared by a process analogous to that described in Method 2 Example 2 using (S)-tert-butyl 2-((S)-1-cyano-2-(4-iodophenyl)ethylcarbamoyl)piperidine-1-carboxylate and 3-(piperidine-1-carbonyl)phenylboronic acid.

¹H NMR (399.826 MHz, d6-DMSO) δ 9.29 (d, J=7.2 Hz, 1H), 9.00-8.91 (m, 1H), 8.81-8.69 (m, 1H), 7.74 (dd, J=7.8, 1.2 Hz, 1H), 7.69 (d, J=8.2 Hz, 2H), 7.63-7.61 (m, 1H), 7.53 (t, J=7.7 Hz, 1H), 7.43 (d, J=8.2 Hz, 2H), 7.35 (d, J=7.5 Hz, 1H), 5.06 (q, J=7.5 Hz, 1H), 3.77 (t, J=10.5 Hz, 1H), 3.64-3.55 (m, 2H), 3.34-3.17 (m, 5H), 2.97-2.87 (m, 1H), 2.08-2.02 (m, 1H), 1.81-1.40 (m, 1H).

m/z [M+H]+=445; [M−H]−=443.

EXAMPLE 84

(S)-N-((S)-1-Cyano-2-(3'-(thiazol-2-ylcarbamoyl)biphenyl-4-yl)ethyl)piperidine-2-carboxamide Trifluoroacetate

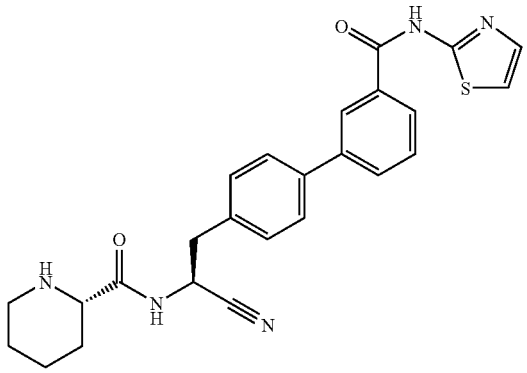

Prepared by a process analogous to that described in Method 2 Example 2 using (S)-tert-butyl 2-((S)-1-cyano-2-(4-iodophenyl)ethylcarbamoyl)piperidine-1-carboxylate and 3-(thiazol-2-ylcarbamoyl)phenylboronic acid.

¹H NMR (399.826 MHz, d6-DMSO) δ 9.31 (d, J=7.4 Hz, 1H), 9.01-8.91 (m, 1H), 8.82-8.69 (m, 1H), 8.46-8.41 (m, 1H), 8.06 (d, J=7.7 Hz, 1H), 7.95 (d, J=7.9 Hz, 1H), 7.82 (d, J=8.5 Hz, 2H), 7.65 (t, J=7.8 Hz, 1H), 7.59 (d, J=3.6 Hz, 1H), 7.47 (d, J=8.2 Hz, 2H), 7.31 (d, J=3.6 Hz, 1H), 5.08 (q, J=7.4 Hz, 1H), 3.83-3.71 (m, 2H), 3.27-3.18 (m, 3H), 2.99-2.86 (m, 1H), 2.11-2.01 (m, 1H), 1.82-1.42 (m, 5H).

m/z [M+H]+=460; [M−H]−=458.

EXAMPLE 85

(S)-N-((S)-1-Cyano-2-(3'-(2-cyanoethylcarbamoyl)biphenyl-4-yl)ethyl)piperidine-2-carboxamide

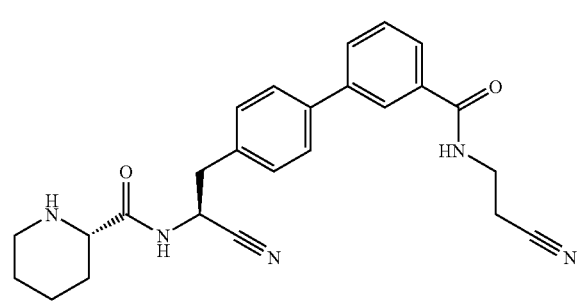

Prepared by a process analogous to that described in Method 2 Example 2 using (S)-tert-butyl 2-((S)-1-cyano-2-(4-iodophenyl)ethylcarbamoyl)piperidine-1-carboxylate and 3-(2-cyanoethylcarbamoyl)phenylboronic acid. NMR appeared to show the product was a free base.

¹H NMR (500.303 MHz, d6-DMSO) δ 9.00-8.94 (m, 1H), 8.56-8.48 (m, 1H), 8.12 (s, 1H), 7.84 (dd, J=8.0, 2.1 Hz, 2H), 7.69 (d, J=8.3 Hz, 2H), 7.57 (t, J=7.5 Hz, 1H), 7.43 (d, J=7.9 Hz, 2H), 5.06-4.98 (m, 1H), 3.53 (q, J=6.4 Hz, 2H), 3.21-3.16 (m, 2H), 3.09-3.05 (m, 1H), 2.80-2.77 (m, 1H), 2.80 (t, J=6.7 Hz, 2H), 1.62-1.56 (m, 2H), 1.44-1.20 (m, 6H).

m/z [M+H]+=430; [M−H]−=428.

EXAMPLE 86

(S)-N-((S)-2-(3'-(2-amino-2-oxoethyl)biphenyl-4-yl)-1-cyanoethyl)piperidine-2-carboxamide Trifluoroacetate

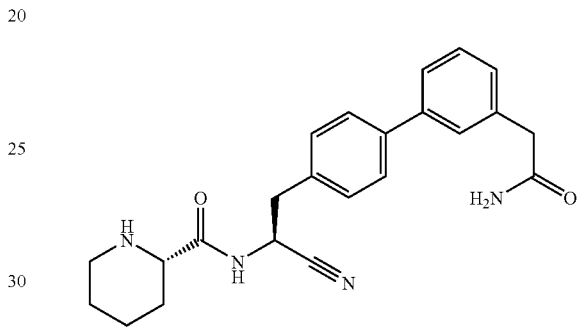

Prepared by a process analogous to that described in Method 2 Example 2 using (S)-tert-butyl 2-((S)-1-cyano-2-(4-iodophenyl)ethylcarbamoyl)piperidine-1-carboxylate and 2-(3-(4,4,5,5-tetramethyl-1,3,2-dioxaborolan-2-yl)phenyl)acetamide.

¹H NMR (399.826 MHz, d6-DMSO) δ 9.32 (d, J=7.4 Hz, 1H), 9.05-8.98 (m, 1H), 8.82-8.70 (m, 1H), 7.62 (d, J=8.6 Hz, 2H), 7.55 (s, 1H), 7.53-7.50 (m, 2H), 7.42 (d, J=8.6 Hz, 2H), 7.38 (d, J=7.3 Hz, 1H), 7.25 (d, J=7.3 Hz, 1H), 6.89 (s, 1H), 5.05 (q, J=7.5 Hz, 1H), 3.83-3.74 (m, 1H), 3.45 (s, 2H), 3.25-3.16 (m, 3H), 2.98-2.86 (m, 1H), 2.08-2.02 (m, 1H), 1.81-1.40 (m, 5H).

m/z [M+H]+=391; [M−H]−=389.

EXAMPLE 87

(S)-N-((S)-1-Cyano-2-(3'-(N,N-dimethylsulfamoyl)biphenyl-4-yl)ethyl)piperidine-2-carboxamide Trifluoroacetate

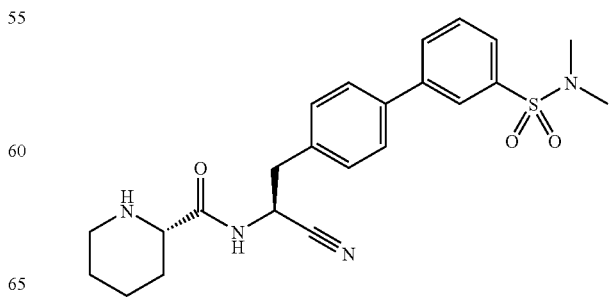

Prepared by a process analogous to that described in Method 2 Example 2 using (S)-tert-butyl 2-((S)-1-cyano-2-(4-iodophenyl)ethylcarbamoyl)piperidine-1-carboxylate and 3-(N,N-dimethylsulfamoyl)phenylboronic acid.

¹H NMR (399.826 MHz, d6-DMSO) δ 9.33 (d, J=7.2 Hz, 1H), 9.05-8.97 (m, 1H), 8.81-8.71 (m, 1H), 8.05-8.00 (m, 1H), 7.90 (s, 1H), 7.80-7.69 (m, 4H), 7.47 (d, J=8.2 Hz, 2H), 5.07 (q, J=7.4 Hz, 1H), 3.83-3.73 (m, 1H), 3.26-3.15 (m, 3H), 2.99-2.87 (m, 1H), 2.66 (s, 6H), 2.09-2.02 (m, 1H), 1.81-1.42 (m, 5H).

m/z [M+H]+=441; [M–H]–=439.

EXAMPLE 88

(S)-N-((S)-1-Cyano-2-(3'-(pyrrolidin-1-ylsulfonyl)biphenyl-4-yl)ethyl)piperidine-2-carboxamide Trifluoroacetate

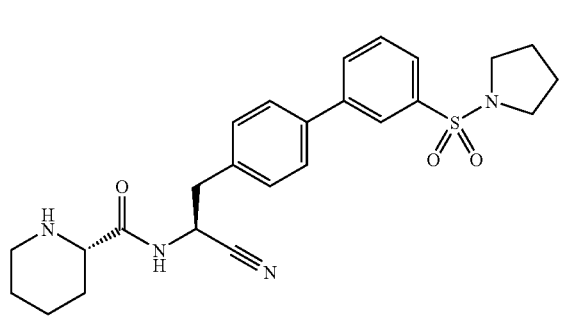

Prepared by a process analogous to that described in Method 2 Example 2 using (S)-tert-butyl 2-((S)-1-cyano-2-(4-iodophenyl)ethylcarbamoyl)piperidine-1-carboxylate and 3-(pyrrolidin-1-ylsulfonyl)phenylboronic acid.

¹H NMR (399.826 MHz, d6-DMSO) δ 9.31 (d, J=7.2 Hz, 1H), 9.00-8.93 (m, 1H), 8.79-8.71 (m, 1H), 8.01 (dm, J=7.7 Hz, 1H), 7.96-7.94 (m, 1H), 7.81 (dm, J=8.1 Hz, 1H), 7.76-7.71 (m, 3H), 7.47 (d, J=8.2 Hz, 2H), 5.07 (q, J=7.4 Hz, 1H), 3.83-3.73 (m, 1H), 3.27-3.14 (m, 7H), 2.97-2.87 (m, 1H), 2.08-2.02 (m, 1H), 1.80-1.44 (m, 9H).

m/z [M+H]+=467; [M–H]–=465.

EXAMPLE 89

(S)-N-((S)-1-Cyano-2-(3'-(methylsulfonamidomethyl)biphenyl-4-yl)ethyl)piperidine-2-carboxamide Trifluoroacetate

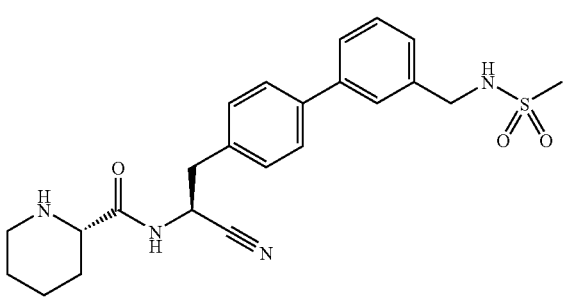

Prepared by a process analogous to that described in Method 2 Example 2 using (S)-tert-butyl 2-((S)-1-cyano-2-(4-iodophenyl)ethylcarbamoyl)piperidine-1-carboxylate and 3-(methylsulfonamidomethyl)phenylboronic acid.

¹H NMR (399.826 MHz, d6-DMSO) δ 9.29 (d, J=7.4 Hz, 1H), 9.00-8.91 (m, 1H), 8.81-8.68 (m, 1H), 7.67-7.54 (m, 5H), 7.47-7.39 (m, 3H), 7.34 (d, J=7.7 Hz, 1H), 5.06 (q, J=7.4 Hz, 1H), 4.23 (d, J=6.2 Hz, 2H), 3.82-3.73 (m, 1H), 3.26-3.17 (m, 3H), 2.98-2.89 (m, 1H), 2.89 (s, 3H), 2.08-2.02 (m, 1H), 1.80-1.43 (m, 5H).

m/z [M+H]+=441; [M–H]–=439.

EXAMPLE 90

(S)-N-((S)-2-(3'-(Acetamidomethyl)biphenyl-4-yl)-1-cyanoethyl)-piperidine-2-carboxamide Trifluoroacetate

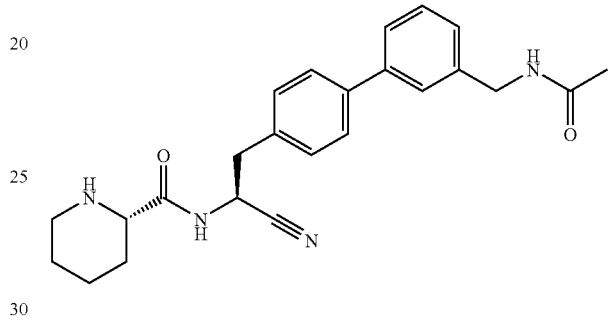

Prepared by a process analogous to that described in Method 2 Example 2 using (S)-tert-butyl 2-((S)-1-cyano-2-(4-iodophenyl)ethylcarbamoyl)piperidine-1-carboxylate and 3-(acetamidomethyl)phenylboronic acid.

¹H NMR (399.826 MHz, d6-DMSO) δ 9.28 (d, J=7.2 Hz, 1H), 8.99-8.91 (m, 1H), 8.80-8.69 (m, 1H), 8.38 (t, J=5.8 Hz, 1H), 7.62 (d, J=8.5 Hz, 2H), 7.55-7.50 (m, 2H), 7.44-7.38 (m, 3H), 7.25 (d, J=7.7 Hz, 1H), 5.05 (q, J=7.5 Hz, 1H), 4.31 (d, J=5.9 Hz, 2H), 3.81-3.72 (m, 1H), 3.25-3.16 (m, 3H), 2.98-2.87 (m, 1H), 2.08-2.01 (m, 1H), 1.88 (s, 3H), 1.80-1.43 (m, 5H).

m/z [M+H]+=405; [M–H]–=403.

EXAMPLE 91

(S)-N-((S)-1-Cyano-2-(4'-(4-cyanopiperidin-1-ylsulfonyl)biphenyl-4-yl)ethyl)piperidine-2-carboxamide Trifluoroacetate

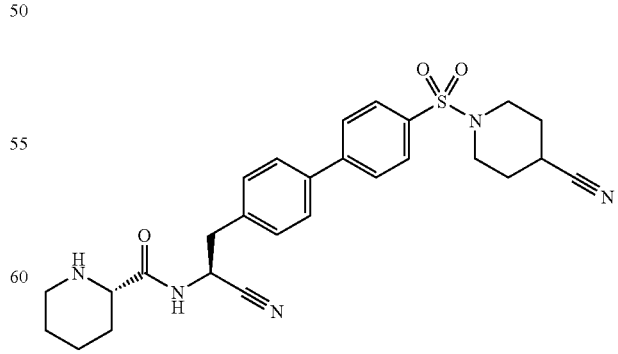

Prepared by a process analogous to that described in Method 2 Example 2 using (S)-tert-butyl 2-((S)-1-cyano-2-(4-iodophenyl)ethylcarbamoyl)piperidine-1-carboxylate and 4-(4-cyanopiperidin-1-ylsulfonyl)phenylboronic acid (in turn prepared from 2-(4-bromophenyl)-6-methyl-1,3,6,2-dioxazaborocane according to the method in Patent WO2004/041833).

$^1$H NMR (399.826 MHz, d6-DMSO) δ 9.27 (d, J=7.2 Hz, 1H), 8.97-8.87 (m, 1H), 8.80-8.68 (m, 1H), 7.95 (d, J=8.8 Hz, 2H), 7.82 (d, J=8.8 Hz, 2H), 7.76 (d, J=8.8 Hz, 2H), 7.47 (d, J=8.8 Hz, 2H), 5.07 (q, J=7.8 Hz, 1H), 3.81-3.71 (m, 1H), 3.26-3.12 (m, 5H), 3.00-2.89 (m, 2H), 2.87-2.78 (m, 2H), 2.09-1.39 (m, 10H).

m/z [M+H]+=506; [M-H]-=504.

EXAMPLE 94

(S)-N-((S)-1-Cyano-2-(4'-(morpholinosulfonyl)biphenyl-4-yl)ethyl)piperidine-2-carboxamide Trifluoroacetate

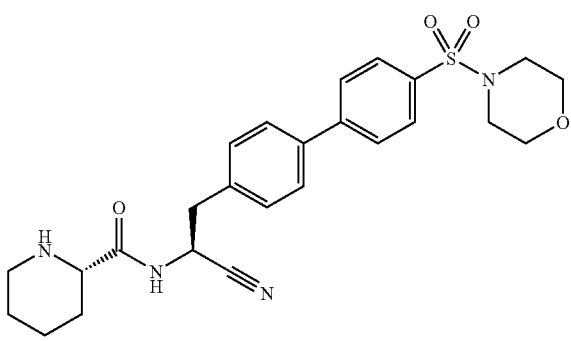

Prepared as a 7:3 (S)/(R) mixture of diastereomers at the aminonitrile methine by a process analogous to that described in Method 2 Example 2 using (S)-tert-butyl 2-((S)-1-cyano-2-(4-iodophenyl)ethylcarbamoyl)piperidine-1-carboxylate and 4-(morpholinosulfonyl)phenylboronic acid.

$^1$H NMR (399.826 MHz, d6-DMSO) δ 9.29 (d, J=7.4 Hz, 1H), 8.97-8.84 (m, 1H), 8.79-8.64 (m, 1H), 7.97-7.94 (m, 2H), 7.83-7.73 (m, 4H), 7.49-7.45 (m, 2H), 5.08 (q, J=7.5 Hz, 1H), 3.82-3.72 (m, 1H), 3.67-3.62 (m, 4H), 3.26-3.16 (m, 4H), 2.94-2.88 (m, 4H), 2.08-2.02 (m, 1H), 1.81-1.41 (m, 5H).

m/z [M+H]+=483.

EXAMPLE 95

(S)-N-((S)-1-Cyano-2-(4'-(4-methylpiperazin-1-ylsulfonyl)biphenyl-4-yl)ethyl)piperidine-2-carboxamide Trifluoroacetate

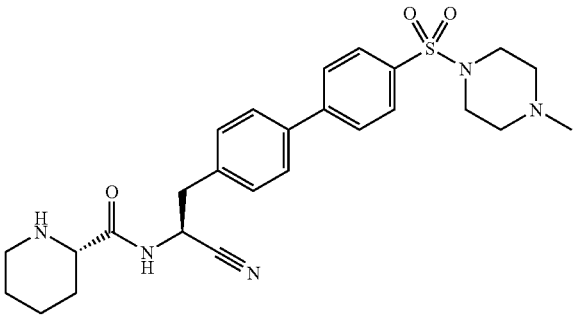

Prepared by a process analogous to that described in Method 2 Example 2 using (S)-tert-butyl 2-((S)-1-cyano-2-(4-iodophenyl)ethylcarbamoyl)piperidine-1-carboxylate and 1-methyl-4-(4-(4,4,5,5-tetramethyl-1,3,2-dioxaborolan-2-yl)phenylsulfonyl)piperazine.

$^1$H NMR (399.826 MHz, d6-DMSO) δ 9.37 (d, J=7.2 Hz, 1H), 9.04 (d, J=9.7 Hz, 1H), 8.77 (d, J=10.3 Hz, 1H), 7.98 (d, J=8.4 Hz, 2H), 7.85 (d, J=8.4 Hz, 2H), 7.75 (d, J=8.4 Hz, 2H), 7.49 (d, J=8.4 Hz, 2H), 5.07 (q, J=7.4 Hz, 1H), 3.93-3.54 (m, 8H), 3.23 (t, J=7.2 Hz, 4H), 2.93 (d, J=10.8 Hz, 1H), 2.79 (s, 3H), 2.06 (d, J=11.3 Hz, 1H), 1.81-1.40 (m, 5H).

m/z [M+H]+=496.

EXAMPLE 96

(S)-N-((S)-1-Cyano-2-(4-(3-methyl-2-oxo-2,3-dihydrobenzo[d]oxazol-5-yl)phenyl)ethyl)piperidine-2-carboxamide

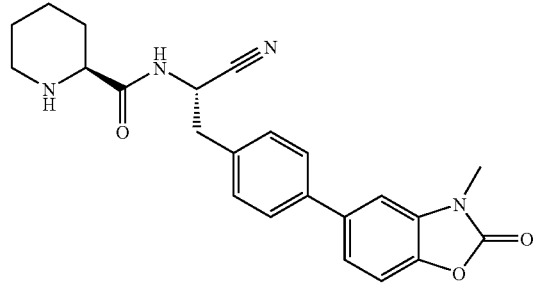

a) (S)-tert-Butyl 2-((S)-1-amino-3-(4-(3-methyl-2-oxo-2,3-dihydrobenzo[d]oxazol-5-yl)phenyl)-1-oxopropan-2-ylcarbamoyl)piperidine-1-carboxylate

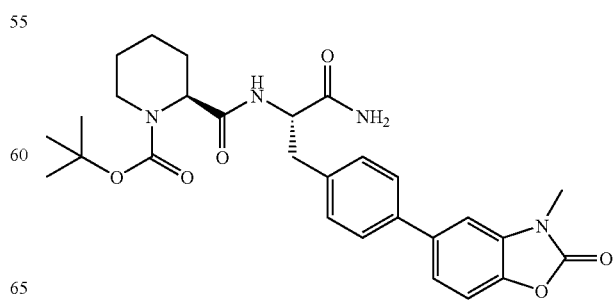

A mixture of (S)-tert-butyl 2-((S)-1-amino-1-oxo-3-(4-(4,4,5,5-tetramethyl-1,3,2-dioxaborolan-2-yl)phenyl)propan-2-ylcarbamoyl)piperidine-1-carboxylate (113 mg), 5-bromo-3-methylbenzo[d]oxazol-2(3H)-one (51.4 mg), [1,1'-bis[bis(1,1-dimethylethyl)phosphino-κP]ferrocene]dichloro palladium (7.34 mg) and potassium carbonate (93 mg) in acetonitrile (0.7 mL) and water (0.35 mL) was stirred at 75° C. for 2 h. The solvent was removed in vacuo and the residue was purified by flash silica chromatography eluting with 1:1 isohexane/acetone to give the subtitle compound (112 mg).

¹H NMR (300 MHz, CDCl₃) δ 7.51 (d, J=8.1 Hz, 2H), 7.32 (d, J=8.1 Hz, 2H), 7.28-7.22 (m, 2H), 7.11 (s, 1H), 6.56 (d, J=8.1 Hz, 1H), 6.16-6.04 (m, 1H), 5.45 (s, 1H), 4.78 (t, J=7.3 Hz, 1H), 4.70-4.63 (m, 1H), 3.91-3.75 (m, 1H), 3.45 (s, 3H), 3.28-3.08 (m, 2H), 2.48-2.30 (m, 1H), 2.17 (s, 6H), 1.61-1.20 (m, 9H).

b) (S)-tert-Butyl 2-((S)-1-cyano-2-(4-(3-methyl-2-oxo-2,3-dihydrobenzo[d]oxazol-5-yl)phenyl)ethyl-carbamoyl)piperidine-1-carboxylate

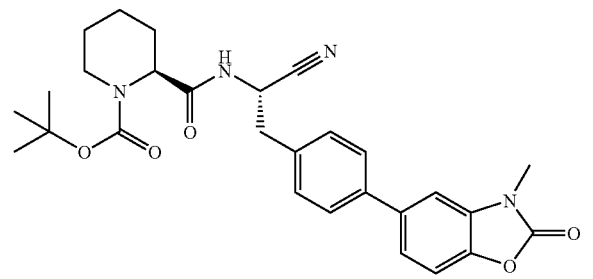

(Methoxycarbonylsulfamoyl)triethylammonium hydroxide, inner salt (137 mg) was added to a solution of (S)-tert-butyl 2-((S)-1-amino-3-(4-(3-methyl-2-oxo-2,3-dihydrobenzo[d]oxazol-5-yl)phenyl)-1-oxopropan-2-ylcarbamoyl)piperidine-1-carboxylate (120 mg) and triethylamine (0.128 ml) in dichloromethane (1 mL) and stirred for 3 h. Water was added and the mixture was extracted with DCM (3 times). The organic layers were dried over (magnesium sulfate), evaporated and purified by flash silica chromatography eluting with acetone 1:2 isohexane/acetone to give the subtitle compound (87 mg).

¹H NMR (300 MHz, CDCl₃) δ 7.55 (d, J=8.1 Hz, 2H), 7.38-7.20 (m, 4H), 7.12 (s, 1H), 5.26-5.13 (m, 1H), 4.70 (s, 1H), 4.07-3.85 (m, 1H), 3.47 (s, 3H), 3.20-3.13 (m, 2H), 2.58-2.38 (m, 1H), 2.28-2.14 (m, 2H), 1.70-1.15 (m, 14H).

c) (S)-N-((S)-1-Cyano-2-(4-(3-methyl-2-oxo-2,3-dihydrobenzo[d]oxazol-5-yl)phenyl)ethyl)piperidine-2-carboxamide

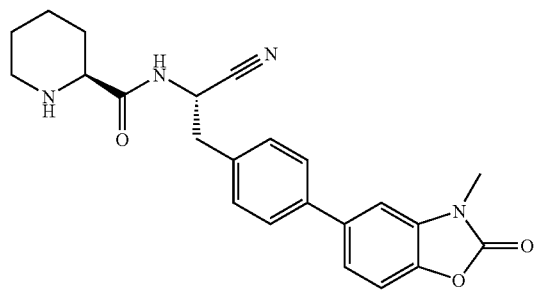

A solution of (S)-tert-butyl 2-((S)-1-cyano-2-(4-(3-methyl-2-oxo-2,3-dihydrobenzo[d]oxazol-5-yl)phenyl)ethyl-carbamoyl)piperidine-1-carboxylate (87 mg) in formic acid (1 mL) was stirred at 50° C. for 15 min. The solvent was removed in vacuo and the residue was purified by flash silica chromatography eluting with 1:29 ammonia in methanol/DCM to give a white solid, which was triturated with diethyl ether to give the title compound (46 mg) as a white solid.

¹H NMR (400 MHz, d6-DMSO) δ 8.51 (d, J=7.9 Hz, 1H), 7.66 (d, J=8.2 Hz, 2H), 7.57 (d, J=1.0 Hz, 1H), 7.43-7.37 (m, 5H), 5.05-4.97 (m, 1H), 3.40 (s, 3H), 3.20-3.14 (m, 3H), 3.10-3.05 (m, 1H), 2.83-2.76 (m, 1H), 1.64-1.56 (m, 2H), 1.45-1.19 (m, 4H).

m/z [M+H]⁺=405.

EXAMPLE 97
(S)-N-((S)-1-Cyano-2-(4-(3-(2-methoxyethyl)-2-oxo-2,3-dihydrobenzo[d]-oxazol-5-yl)phenyl)ethyl)piperidine-2-carboxamide

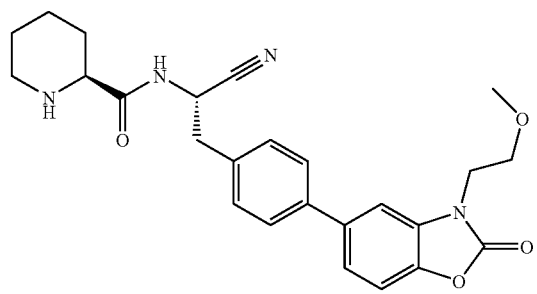

a) 5-Bromo-3-(2-methoxyethyl)benzo[d]oxazol-2(3H)-one

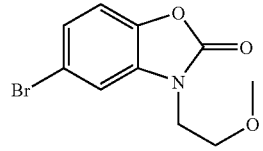

A mixture of 5-bromobenzo[d]oxazol-2(3H)-one (2.06 g), 1-bromo-2-methoxyethane (1.085 mL) and potassium carbonate (3.99 g) in acetonitrile (15 mL) was heated at 60° C. for 16 h. Water was added and the mixture was extracted with ethyl acetate (3 times). The organic layers were dried over magnesium sulfate, evaporated and purified by flash silica chromatography eluting with 5:1 isohexane/acetone to give the subtitle compound (1.359 g).

¹H NMR (300 MHz, CDCl₃) δ 7.28-7.18 (m, 2H), 7.06 (d, J=16.1 Hz, 1H), 3.97 (t, J=5.1 Hz, 2H), 3.69 (t, J=5.1 Hz, 2H), 3.36 (s, 3H).

b) (S)-tert-Butyl 2-((S)-1-amino-3-(4-(3-(2-methoxyethyl)-2-oxo-2,3-dihydrobenzo[d]oxazol-5-yl)phenyl)-1-oxopropan-2-ylcarbamoyl)piperidine-1-carboxylate

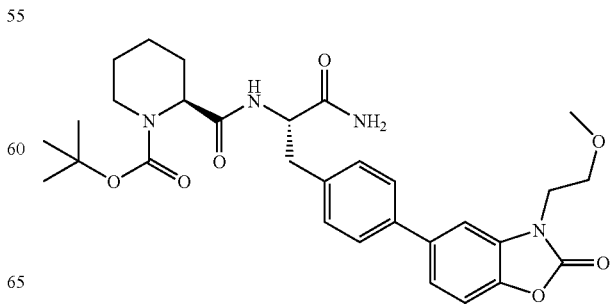

The sub-title compound was prepared by the method of Example 96 step (a) using 5-bromo-3-(2-methoxyethyl)benzo[d]oxazol-2(3H)-one and (S)-tert-butyl 2-((S)-1-amino-1-oxo-3-(4-(4,4,5,5-tetramethyl-1,3,2-dioxaborolan-2-yl)phenyl)propan-2-ylcarbamoyl)piperidine-1-carboxylate.

¹H NMR (400 MHz, CDCl₃) δ 7.52-7.48 (m, 2H), 7.35-7.21 (m, 5H), 6.52 (d, J=18.0 Hz, 1H), 5.42-5.33 (m, 2H), 4.82-4.62 (m, 4H), 4.04 (t, J=5.3 Hz, 2H), 3.91-3.77 (m, 3H), 3.75-3.62 (m, 3H), 3.35 (s, 3H), 3.27-3.02 (m, 4H), 1.63-1.39 (m, 9H).

c) (S)-tert-Butyl 2-((S)-1-cyano-2-(4-(3-(2-methoxyethyl)-2-oxo-2,3-dihydrobenzo[d]oxazol-5-yl)phenyl)ethylcarbamoyl)piperidine-1-carboxylate

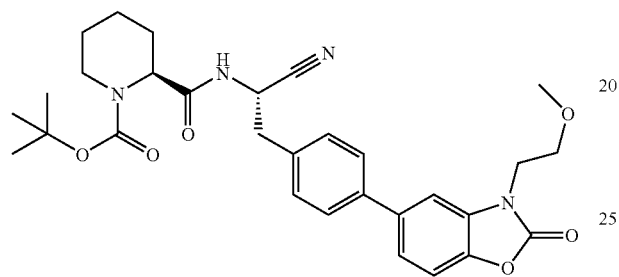

The sub-title compound was prepared by the method of Example 96, step (b) using (S)-tert-butyl 2-((S)-1-amino-3-(4-(3-(2-methoxyethyl)-2-oxo-2,3-dihydrobenzo[d]oxazol-5-yl)phenyl)-1-oxopropan-2-ylcarbamoyl)piperidine-1-carboxylate.
m/z [M−H]⁻=547.

d) (S)-N-((S)-1-Cyano-2-(4-(3-(2-methoxyethyl)-2-oxo-2,3-dihydrobenzo[d]oxazol-5-yl)phenyl)ethyl)piperidine-2-carboxamide

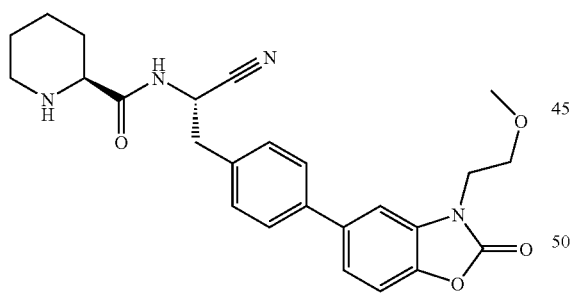

A solution of (S)-tert-butyl 2-((S)-1-cyano-2-(4-(3-(2-methoxyethyl)-2-oxo-2,3-dihydrobenzo[d]oxazol-5-yl)phenyl)ethylcarbamoyl)piperidine-1-carboxylate (38 mg) in formic acid (1 mL) was stirred at 50° C. for 10 min. The solvent was removed in vacuo and the residue was purified by flash silica chromatography eluting with 1:24 2M ammonia in methanol/DCM to give, after trituration with diethyl ether, the title compound (27 mg) as a pale yellow solid.

¹H NMR (400 MHz, d6-DMSO) δ 8.57-8.45 (m, 1H), 7.64 (t, J=8.2 Hz, 3H), 7.39 (d, J=4.6 Hz, 4H), 5.06-4.97 (m, 1H), 4.07 (t, J=5.0 Hz, 2H), 3.67 (t, J=5.3 Hz, 2H), 3.25 (s, 3H), 3.20-3.15 (m, 3H), 3.11-3.05 (m, 2H), 2.79 (d, J=12.3 Hz, 1H), 1.63-1.54 (m, 2H), 1.46-1.19 (m, 4H).
m/z [M+H]⁺=449.

EXAMPLE 98

(S)-N-((S)-1-Cyano-2-(4-(3-methyl-2-oxo-2,3-dihydrobenzo[d]thiazol-6-yl)phenyl)ethyl)piperidine-2-carboxamide

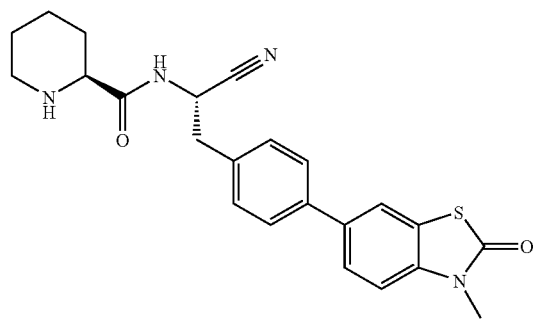

a) (S)-tert-Butyl 2-((S)-1-amino-3-(4-(3-methyl-2-oxo-2,3-dihydrobenzo[d]thiazol-6-yl)phenyl)-1-oxopropan-2-ylcarbamoyl)piperidine-1-carboxylate

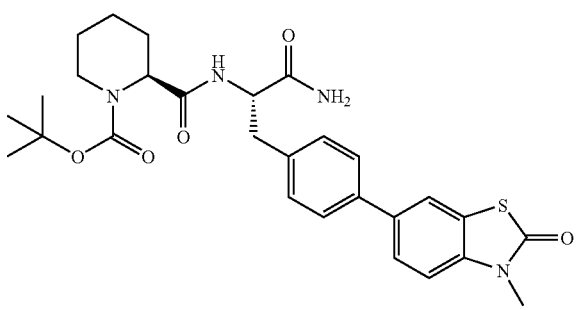

The subtitle compound was prepared by the method of Example 96 step (a) using (S)-tert-butyl 2-((S)-1-amino-1-oxo-3-(4-(4,4,5,5-tetramethyl-1,3,2-dioxaborolan-2-yl)phenyl)propan-2-ylcarbamoyl)piperidine-1-carboxylate and 6-bromo-3-methylbenzo[d]thiazol-2(3H)-one.

¹H NMR (300 MHz, CDCl₃) δ 7.64 (s, 1H), 7.55-7.47 (m, 3H), 7.35-7.25 (m, 3H), 7.10 (d, J=7.5 Hz, 1H), 6.56 (d, J=7.5 Hz, 1H), 6.15 (s, 1H), 5.50 (s, 1H), 4.80 (q, J=6.9 Hz, 1H), 4.70-4.64 (m, 1H), 3.91-3.75 (m, 1H), 3.51-3.46 (m, 3H), 3.28-3.08 (m, 2H), 2.48-2.30 (m, 1H), 2.01 (t, J=1.4 Hz, 1H), 1.60-1.46 (m, 3H), 1.43 (s, 9H), 1.34-1.18 (m, 1H).

b) (S)-tert-Butyl 2-((S)-1-cyano-2-(4-(3-methyl-2-oxo-2,3-dihydrobenzo[d]thiazol-6-yl)phenyl)ethylcarbamoyl)piperidine-1-carboxylate

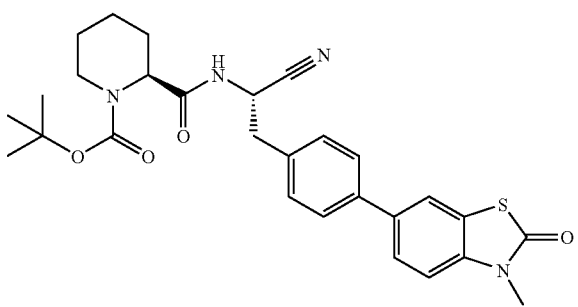

The sub-title compound was prepared by the method of Example 96, step (b) using (S)-tert-butyl 2-((S)-1-amino-3-(4-(3-methyl-2-oxo-2,3-dihydrobenzo[d]thiazol-6-yl)phenyl)-1-oxopropan-2-ylcarbamoyl)piperidine-1-carboxylate.

¹H NMR (300 MHz, CDCl₃) δ 7.65-7.46 (m, 4H), 7.39-7.22 (m, 2H), 7.11 (d, J=20.5 Hz, 1H), 5.25-5.13 (m, 1H), 4.73-4.65 (m, 1H), 4.02-3.82 (m, 1H), 3.52-3.41 (m, 3H), 3.23-3.08 (m, 2H), 2.54-2.37 (m, 1H), 2.27-2.12 (m, 1H), 1.79-1.16 (m, 15H).

c) (S)-N-((S)-1-Cyano-2-(4-(3-methyl-2-oxo-2,3-dihydrobenzo[d]thiazol-6-yl)phenyl)ethyl)piperidine-2-carboxamide

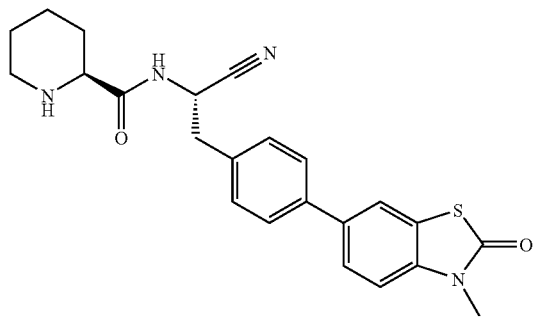

The title compound was prepared by the method of Example 96, step (c) using (S)-tert-butyl 2-((S)-1-cyano-2-(4-(3-methyl-2-oxo-2,3-dihydrobenzo[d]thiazol-6-yl)phenyl)ethylcarbamoyl)piperidine-1-carboxylate.

¹H NMR (400 MHz, d6-DMSO) δ 8.54 (d, J=7.4 Hz, 1H), 8.00 (d, J=1.8 Hz, 1H), 7.69 (dd, J=8.5, 2.1 Hz, 1H), 7.64 (d, J=8.2 Hz, 2H), 7.38 (d, J=32.5 Hz, 3H), 5.00 (q, J=12.3 Hz, 1H), 3.48 (s, 3H), 3.21-3.07 (m, 5H), 2.85-2.77 (m, 1H), 1.65-1.56 (m, 2H), 1.46-1.39 (m, 1H), 1.36-1.20 (m, 3H).

m/z [M+H]⁺=421.

EXAMPLE 99

(S)-N-((S)-1-Cyano-2-(4-(3-(2-hydroxyethyl)-2-oxo-2,3-dihydrobenzo[d]thiazol-6-yl)phenyl)ethyl)piperidine-2-carboxamide

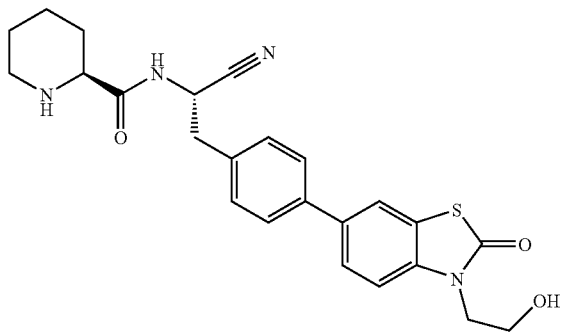

a) (S)-tert-Butyl 2-((S)-1-amino-3-(4-(3-(2-hydroxyethyl)-2-oxo-2,3-dihydrobenzo[d]thiazol-6-yl)phenyl)-1-oxopropan-2-ylcarbamoyl)piperidine-1-carboxylate

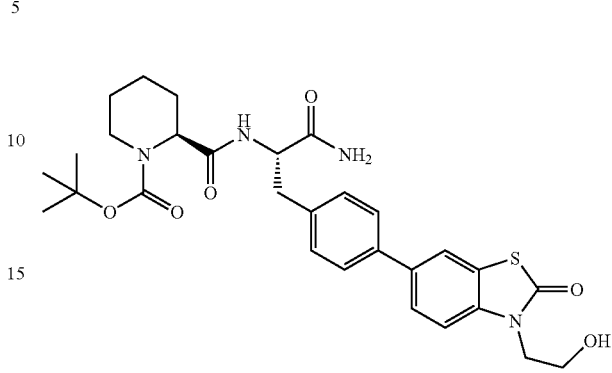

The subtitle compound was prepared by the method of Example 96 step (a) using (S)-tert-butyl 2-((S)-1-amino-1-oxo-3-(4-(4,4,5,5-tetramethyl-1,3,2-dioxaborolan-2-yl)phenyl)propan-2-ylcarbamoyl)piperidine-1-carboxylate and 6-bromo-3-(2-hydroxyethyl)benzo[d]thiazol-2(3H)-one.
m/z [M-BOC+H]⁺=469.

b) (S)-tert-Butyl 2-((S)-1-amino-3-(4-(3-(2-(tert-butyldimethylsilyloxy)ethyl)-2-oxo-2,3-dihydrobenzo[d]thiazol-6-yl)phenyl)-1-oxopropan-2-ylcarbamoyl)piperidine-1-carboxylate

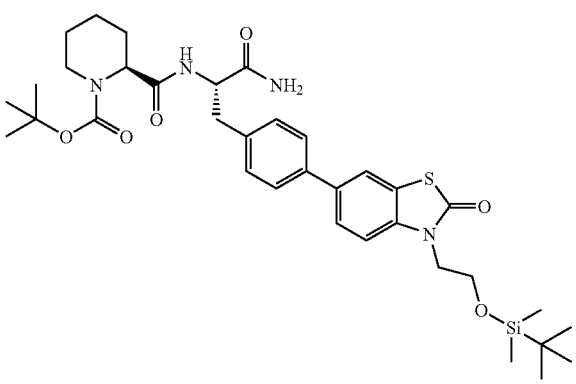

A solution of (S)-tert-butyl 2-((S)-1-amino-3-(4-(3-(2-hydroxyethyl)-2-oxo-2,3-dihydrobenzo[d]thiazol-6-yl)phenyl)-1-oxopropan-2-ylcarbamoyl)piperidine-1-carboxylate (138 mg), tert-butyldimethylsilyl chloride (40.2 mg) and imidazole (41.3 mg) in DMF (1 mL) was stirred for 16 h. Further tert-butyldimethylsilyl chloride (40.2 mg) and imidazole (41.3 mg) were added and stirred for 4 h. Water was added and the mixture was extracted thrice with ethyl acetate. The organic layers were washed twice with water, combined, dried over magnesium sulfate, evaporated and purified by flash silica chromatography eluting with 1:2 acetone/isohexane to give the subtitle compound (130 mg) as a colourless gum.

¹H NMR (300 MHz, CDCl₃) δ 7.69-7.52 (m, 5H), 7.41-7.20 (m, 6H), 6.58 (d, J=18.6 Hz, 1H), 5.45 (s, 1H), 4.86 (q, J=7.3 Hz, 1H), 4.77-4.71 (m, 1H), 4.22-4.15 (m, 2H), 4.02 (t, J=5.4 Hz, 2H), 3.34-3.16 (m, 2H), 3.04 (s, 1H), 2.96 (s, 1H), 1.74-1.58 (m, 12H), 0.86 (s, 9H), 0.02 (s, 6H).

c) (S)-tert-Butyl 2-((S)-2-(4-(3-(2-(tert-butyldimethylsilyloxy)ethyl)-2-oxo-2,3-dihydrobenzo[d]thiazol-6-yl)phenyl)-1-cyanoethylcarbamoyl)piperidine-1-carboxylate

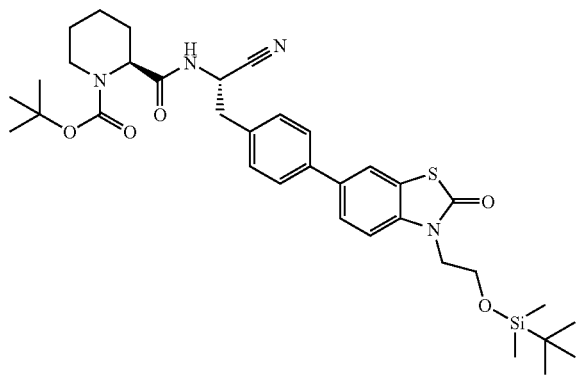

The subtitle compound was prepared by the method of Example 96 step (c) using (S)-tert-butyl 2-((S)-1-amino-3-(4-(3-(2-(tert-butyldimethylsilyloxy)ethyl)-2-oxo-2,3-dihydrobenzo[d]thiazol-6-yl)phenyl)-1-oxopropan-2-ylcarbamoyl)piperidine-1-carboxylate.

$^1$H NMR (300 MHz, CDCl$_3$) δ 7.68-7.52 (m, 3H), 7.43-7.34 (m, 4H), 5.33-5.23 (m, 1H), 4.79-4.73 (m, 1H), 4.19 (t, J=5.4 Hz, 2H), 4.02 (t, J=5.3 Hz, 3H), 3.31-3.15 (m, 2H), 2.60-2.41 (m, 1H), 2.34-2.22 (m, 1H), 1.74-1.37 (m, 15H), 0.89 (s, 9H), 0.02 (s, 6H).

d) (S)-N-((S)-1-Cyano-2-(4-(3-(2-hydroxyethyl)-2-oxo-2,3-dihydrobenzo[d]thiazol-6-yl)phenyl)ethyl)piperidine-2-carboxamide

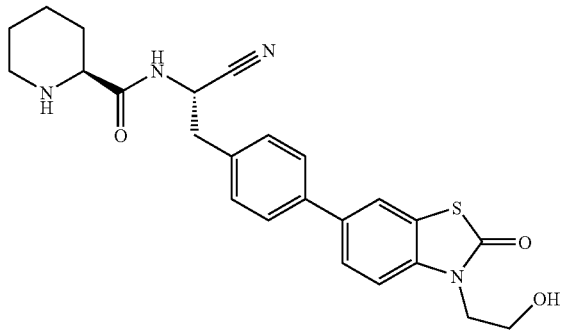

A solution of (S)-tert-butyl 2-((S)-2-(4-(3-(2-(tert-butyldimethylsilyloxy)ethyl)-2-oxo-2,3-dihydrobenzo[d]thiazol-6-yl)phenyl)-1-cyanoethylcarbamoyl)piperidine-1-carboxylate (103 mg) in formic acid (1 ml) was stirred at 50° C. for 10 min. The solvent was removed in vacuo and the residue was purified by flash silica chromatography eluting with 1:14 2M ammonia in methanol/DCM to give, after trituration with diethyl ether, the title compound (60 mg) as a white solid.

$^1$H NMR (400 MHz, d6-DMSO) δ 8.51 (d, J=33.1 Hz, 1H), 8.00-7.95 (m, 1H), 7.67-7.61 (m, 3H), 7.44 (t, J=8.8 Hz, 1H), 7.38 (d, J=8.2 Hz, 2H), 5.04-4.97 (m, 1H), 4.94 (t, J=5.6 Hz, 1H), 4.03 (t, J=5.5 Hz, 2H), 3.68 (q, J=5.7 Hz, 2H), 3.17 (q, J=3.9 Hz, 2H), 3.08 (d, J=8.5 Hz, 1H), 2.79 (d, J=13.1 Hz, 1H), 1.63-1.55 (m, 2H), 1.45-1.19 (m, 5H).

m/z [M+H]$^+$=451.

EXAMPLE 100

(S)-N-((S)-1-Cyano-2-(4'-cyanobiphenyl-3-yl)ethyl)piperidine-2-carboxamide Trifluoroacetate

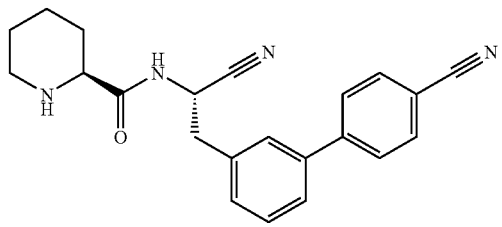

Prepared by a process analogous to that described in Method 2 Example 2 using (S)-tert-butyl 2-((S)-1-cyano-2-(3-iodophenyl)ethylcarbamoyl)piperidine-1-carboxylate and 4-cyanophenylboronic acid.

$^1$H NMR (399.826 MHz, d6-DMSO) δ 9.30 (d, J=7.2 Hz, 1H), 9.01-8.93 (m, 1H), 8.79-8.70 (m, 1H), 7.97-7.94 (m, 2H), 7.92-7.88 (m, 2H), 7.75 (s, 1H), 7.68 (d, J=7.9 Hz, 1H), 7.49 (t, J=7.7 Hz, 1H), 7.39 (d, J=7.4 Hz, 1H), 5.13 (q, J=7.5 Hz, 1H), 3.79-3.71 (m, 1H), 3.27-3.18 (m, 3H), 2.97-2.85 (m, 1H), 2.04-1.98 (m, 1H), 1.77-1.41 (m, 5H).

m/z [M+H]+=359.

EXAMPLE 101

(S)-N-((S)-1-Cyano-2-(4'-(cyanomethyl)-3'-(methylsulfonyl)biphenyl-4-yl)ethyl)-piperidine-2-carboxamide Trifluoroacetate

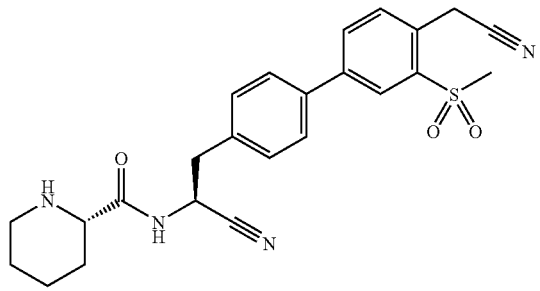

a) (S)-tert-Butyl 2-((S)-1-amino-3-(4'-(cyanomethyl)-3'-(methylsulfonyl)biphenyl-4-yl)-1-oxopropan-2-ylcarbamoyl)piperidine-1-carboxylate

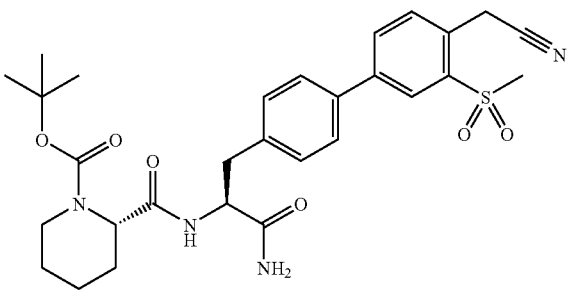

A mixture of (S)-tert-butyl 2-((S)-1-amino-1-oxo-3-(4-(4,4,5,5-tetramethyl-1,3,2-dioxaborolan-2-yl)phenyl)propan-2-ylcarbamoyl)piperidine-1-carboxylate (92 mg), 2-(4-bromo-2-(methylsulfonyl)phenyl)acetonitrile (75 mg), bis(1,2-bis(diphenylphosphino)ethane)-palladium(0) (8.29 mg, 9.17 μmol) and 2 N aqueous potassium carbonate (0.229 mL) in dioxane (3 mL) was heated at 75° C. for 14 h. The mixture was poured onto an Isolute HM-N cartridge, eluting with DCM, collecting about 100 mL of eluent. The eluent was concentrated in vacuo to leave a brown oil. The residue was purified by flash silica chromatography, eluting with ethyl acetate to give the subtitle compound as a white solid (80 mg).

m/z [M-BOC+H]+=469; [M-H]-=567.

b) (S)-N-((S)-1-Cyano-2-(4'-(cyanomethyl)-3'-(methylsulfonyl)biphenyl-4-yl)ethyl)piperidine-2-carboxamide Trifluoroacetate

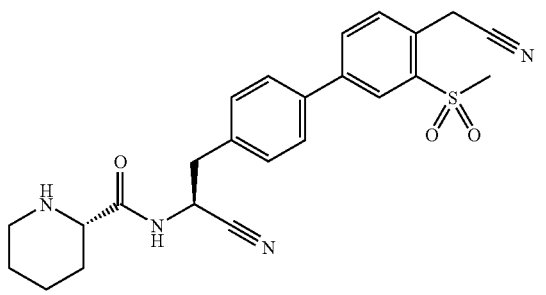

Triethylamine (0.125 mL) in DCM (2 mL) was stirred, under nitrogen, in a cold water bath and methyl chlorosulfonylcarbamate (61 mg) was added portionwise. Once addition was complete, the cold water bath was removed and the mixture was stirred at RT for 30 min. (S)-tert-Butyl 2-((S)-1-amino-3-(4'-(cyanomethyl)-3'-(methylsulfonyl)biphenyl-4-yl)-1-oxopropan-2-ylcarbamoyl)piperidine-1-carboxylate (80 mg) in DCM (3 mL) was added dropwise and the mixture was stirred at RT for 18 h. The mixture was washed with water and brine then dried over magnesium sulfate, filtered and concentrated in vacuo. The brown oil was dissolved in formic acid (5 mL) and heated at 50° C. for 15 min, then concentrated in vacuo. The residue was purified by RPHPLC (95 to 50% 0.1% TFA(aq)/MeCN on a SunFire® 30×100 mm column to give a translucent gum that was triturated with diethyl ether to leave the title compound as a white solid (27 mg).

¹H NMR (399.826 MHz, d6-DMSO) δ 9.27 (d, J=7.4 Hz, 1H), 8.98-8.88 (m, 1H), 8.80-8.69 (m, 1H), 8.18 (d, J=2.1 Hz, 1H), 8.10 (dd, J=7.9, 2.1 Hz, 1H), 7.81 (d, J=8.2 Hz, 1H), 7.75 (d, J=8.2 Hz, 2H), 7.48 (d, J=8.2 Hz, 2H), 5.08 (q, J=7.4 Hz, 1H), 4.47 (s, 2H), 3.80-3.72 (m, 1H), 3.38 (s, 3H), 3.25-3.18 (m, 3H), 2.99-2.88 (m, 1H), 2.08-2.02 (m, 1H), 1.81-1.42 (m, 5H).

m/z [M+H]+=451; [M-H]-=449.

EXAMPLE 102

(S)-N-((S)-1-Cyano-2-(4-(phenylsulfonyl)phenyl)ethyl)piperidine-2-carboxamide

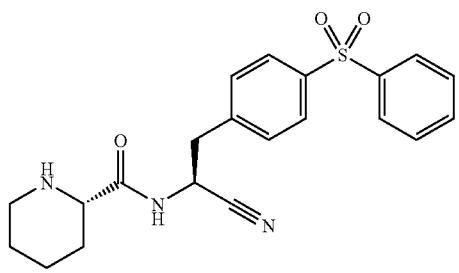

a) (S)-Methyl 2-(tert-butoxycarbonylamino)-3-(4-(phenylsulfonyl)phenyl)propanoate

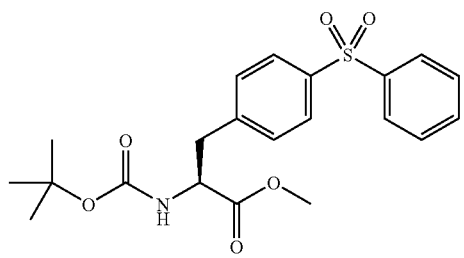

Zinc dust (<10 micron particle size) (0.271 g) and iodine (0.016 g) were weighed into a 3-neck 100 mL round bottomed flask with a magnetic stirrer. The flask was heated with a heat gun for 10 min, then evacuated and flushed with nitrogen three times and allowed to cool to RT. Dry DMF (0.5 mL) followed by a solution of (R)-methyl 2-(tert-butoxycarbonylamino)-3-iodopropanoate (1.05 g) in DMF (7 mL) were added via syringe to the well-stirred suspension of zinc dust, and the mixture was cooled to 0° C. and stirred for 30 min. The ice bath was removed before 1-bromo-4-(phenylsulfonyl)benzene (0.948 g) and dichlorobis(triphenylphosphine)-palladium(II) (0.090 g) were added, and then the mixture was heated at 65° C. for 15 h. The cooled mixture was poured into a 2% w/v citric acid solution and this was extracted thrice with ethyl acetate. The combined organic phases were dried over magnesium sulphate, filtered and concentrated in vacuo to leave an orange oil. This was purified by flash silica chromatography, eluting with 1:4 to 1:3 ethyl acetate/isohexane, to give the subtitle compound (0.72 g) as a pale brown gum.

¹H NMR (299.946 MHz, CDCl₃) δ 7.94 (d, J=8.3 Hz, 2H), 7.87 (d, J=8.7 Hz, 2H), 7.60-7.47 (m, 4H), 7.31-7.25 (m, 1H), 5.03-4.93 (m, 1H), 4.63-4.53 (m, 1H), 3.69 (s, 3H), 3.19 (dd, J=13.6, 5.7 Hz, 1H), 3.10-2.98 (m, 1H), 1.36 (s, 9H).

b) (S)-2-(tert-Butoxycarbonylamino)-3-(4-(phenyl-sulfonyl)phenyl)propanoic Acid

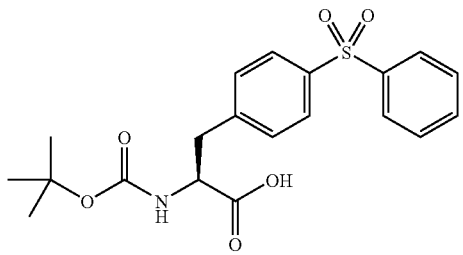

To a stirred solution of (S)-methyl 2-(tert-butoxycarbonylamino)-3-(4-(phenylsulfonyl)phenyl)propanoate (700 mg) in THF (15 mL) and water (10 mL) was added lithium hydroxide monohydrate (140 mg). The mixture was stirred at RT for 2 h. The mixture was partitioned between 0.1 N HCl (aq) and ethyl acetate, and the aqueous phase was extracted twice more with ethyl acetate. The combined organic phases were dried over sodium sulphate, filtered and concentrated in vacuo to leave the subtitle compound (675 mg) as a white solid.

m/z [M−tBu+H]+=349; [M−BOC+H]+=306; [M−H]−=404.

c) (S)-tert-Butyl 1-amino-1-oxo-3-(4-(phenylsulfonyl)phenyl)propan-2-ylcarbamate

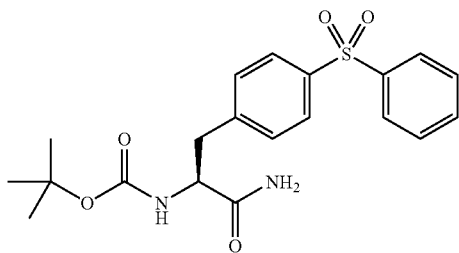

(S)-2-(tert-Butoxycarbonylamino)-3-(4-(phenylsulfonyl)phenyl)propanoic acid (675 mg) was dissolved in DMF (8 mL) and to the solution was added N-ethylmorpholine (0.316 mL) followed by TBTU (802 mg). The reaction mixture was stirred at room temperature for 20 min then it was cooled to 0° C. Aqueous ammonia (0.379 mL) was added and the mixture was allowed to reach room temperature over 1 h. The reaction mixture was left to stir for a further 2 h. LCMS showed little change so further TBTU (400 mg) and ammonia (0.3 mL) were added, and the mixture stirred for a further 2 h. The reaction mixture was partitioned between ethyl acetate and diluted brine, and the aqueous phase was extracted into ethyl acetate twice more. The combined organic phases were dried over sodium sulphate, filtered and concentrated in vacuo to yield a pale gum. This was purified by flash silica chromatography, eluting with ethyl acetate to give the subtitle compound (450 mg) as a colourless gum.

$^1$H NMR (399.826 MHz, d6-DMSO) δ 7.93 (d, J=7.4 Hz, 2H), 7.86 (d, J=8.2 Hz, 2H), 7.68 (tm, J=7.2 Hz, 1H), 7.60 (t, J=7.7 Hz, 2H), 7.48 (d, J=8.3 Hz, 2H), 7.37 (s, 1H), 7.04 (s, 1H), 6.84 (d, J=9.3 Hz, 1H), 4.15-4.06 (m, 1H), 3.04 (dd, J=13.7, 4.2 Hz, 1H), 2.80-2.71 (m, 1H), 1.19 (s, 9H).

m/z [M−BOC+H]+=305.

d) (S)-2-Amino-3-(4-(phenylsulfonyl)phenyl)propanamide

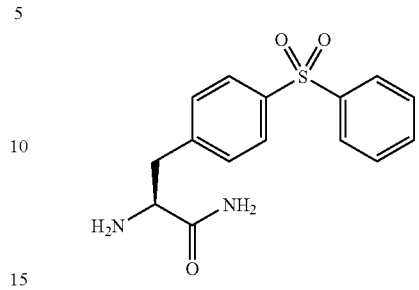

To a stirred solution of (S)-tert-butyl 1-amino-1-oxo-3-(4-(phenylsulfonyl)phenyl)propan-2-ylcarbamate (440 mg) in DCM (10 mL) at 0° C. was added TFA (2.51 mL). The mixture was allowed to warm to RT and stirred for 1 h. The mixture was concentrated in vacuo and partitioned between saturated aqueous sodium bicarbonate and ethyl acetate, dried over sodium sulfate, filtered and concentrated in vacuo to leave the subtitle compound (175 mg) as a white solid.

m/z [M+H]+=305; [M−H]−=303.

e) (S)-tert-Butyl 2-((S)-1-amino-1-oxo-3-(4-(phenyl-sulfonyl)phenyl)propan-2-ylcarbamoyl)piperidine-1-carboxylate

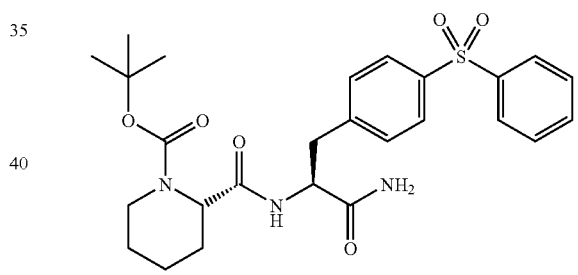

A 50% solution of 1-propylphosphonic acid cyclic anhydride in DMF (226 mg) was added to a stirred solution of (S)-(−)-1-(tert-butoxycarbonyl)-2-piperidinecarboxylic acid (81 mg), (S)-2-amino-3-(4-(phenylsulfonyl)phenyl)propanamide (90 mg) and triethylamine (0.206 mL) in DMF (2 mL) at 0° C. The resulting solution was stirred at 0° C. for 30 min then warmed to room temperature and stirred for a further 30 min. Water (50 mL) and saturated brine (30 mL) were added and the mixture was extracted with ethyl acetate (2×50 mL). The combined organic phases were washed with 1:1 water/saturated brine (2×50 mL), dried over magnesium sulfate and the filtrate was concentrated in vacuo to afford a dark oil contaminated with DMF. This was purified by flash silica chromatography, eluting with 1:2 then 2:1 ethyl acetate/isohexane, then ethyl acetate to give the subtitle compound (125 mg) as a brown oil.

m/z [M−BOC+H]+=416; [M−H]−=514.

f) (S)-N-((S)-1-Cyano-2-(4-(phenylsulfonyl)phenyl)ethyl)piperidine-2-carboxamide Trifluoroacetate

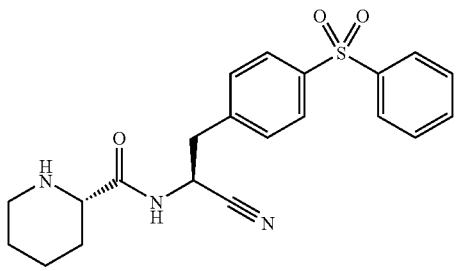

To a solution of (S)-tert-butyl 2-((S)-1-amino-1-oxo-3-(4-(phenylsulfonyl)phenyl)propan-2-ylcarbamoyl)piperidine-1-carboxylate (120 mg) and triethylamine (0.130 mL) in DCM (4 mL) was added Burgess reagent (139 mg) in small portions, and the mixture was stirred at RT for 18 h. The mixture was diluted with diethyl ether, washed with 1:1 water/brine then dried over sodium sulfate, filtered and concentrated in vacuo. This was dissolved in formic acid (5 mL) and heated at 50° C. for 15 min, then concentrated in vacuo. The residue was purified by RPHPLC (95 to 50% 0.1% TFA (aq)/MeCN) using a SunFire® 30×100 mm column to give a translucent gum that was triturated with diethyl ether to leave the title compound (72 mg) as a white solid.

$^1$H NMR (399.826 MHz, d6-DMSO) δ 9.21 (d, J=7.2 Hz, 1H), 8.96-8.84 (m, 1H), 8.78-8.65 (m, 1H), 7.99-7.91 (m, 4H), 7.70 (t, J=7.8 Hz, 1H), 7.63 (t, J=7.8 Hz, 2H), 7.55 (d, J=8.7 Hz, 2H), 5.08 (q, J=8.0 Hz, 1H), 3.76-3.68 (m, 1H), 3.28-3.16 (m, 3H), 2.94-2.84 (m, 1H), 1.96-1.89 (m, 1H), 1.74-1.39 (m, 5H).

m/z [M+H]+=398; [M−H]−=396.

EXAMPLE 103

(S)-N-((1R,2R)-1-Cyano-2-(4'-cyanobiphenyl-4-yl)cyclopropyl)piperidine-2-carboxamide Trifluoroacetate

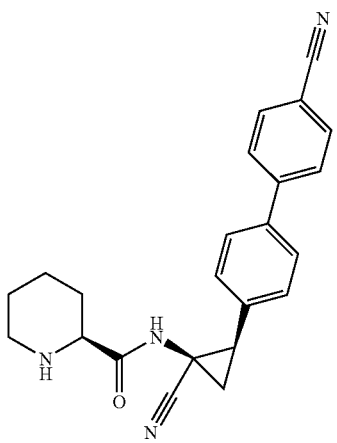

Prepared by a process analogous to that described in Method 2 Example 2 using (S)-tert-butyl 2-((1R,2R)-2-(4-bromophenyl)-1-cyanocyclopropylcarbamoyl)piperidine-1-carboxylate (Intermediate 10) and 4-cyanophenylboronic acid.

$^1$H NMR (399.826 MHz, d6-DMSO) δ 9.02 (s, 1H), 8.92-8.83 (m, 1H), 8.74-8.65 (m, 1H), 7.95-7.89 (m, 4H), 7.74 (dm, J=8.3 Hz, 2H), 7.37 (dm, J=8.7 Hz, 2H), 3.65-3.57 (m, 1H), 3.23-3.11 (m, 2H), 2.90-2.80 (m, 1H), 2.19 (dd, J=10.0, 6.9 Hz, 1H), 1.92-1.82 (m, 2H), 1.76-1.34 (m, 5H).

m/z [M+H]+=371; [M−H]−=369.

EXAMPLE 104

(S)-N-((1R,2R)-2-(4'-(Azetidin-1-ylsulfonyl)biphenyl-4-yl)-1-cyanocyclopropyl)piperidine-2-carboxamide Trifluoroacetate

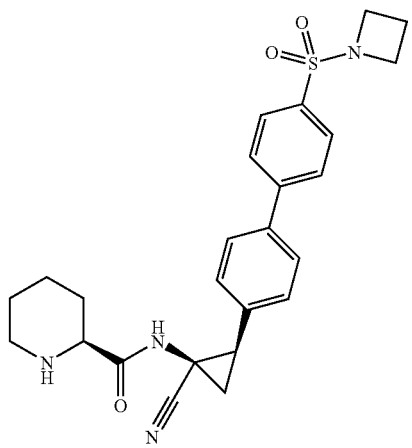

Prepared by a process analogous to that described in Method 2 Example 2 using (S)-tert-butyl 2-((1R,2R)-2-(4-bromophenyl)-1-cyanocyclopropylcarbamoyl)piperidine-1-carboxylate (Intermediate 10) and 4-(azetidin-1-ylsulfonyl)phenylboronic acid.

$^1$H NMR (399.826 MHz, d6-DMSO) δ 9.02 (s, 1H), 8.90-8.82 (m, 1H), 8.74-8.63 (m, 1H), 7.99 (d, J=8.7 Hz, 2H), 7.88 (d, J=8.7 Hz, 2H), 7.77 (d, J=8.7 Hz, 2H), 7.39 (d, J=9.4 Hz, 2H), 3.74-3.66 (m, 4H), 3.65-3.56 (m, 1H), 3.24-3.12 (m, 2H), 2.91-2.80 (m, 1H), 2.19 (dd, J=10.0, 6.9 Hz, 1H), 2.06-1.97 (m, 2H), 1.92-1.82 (m, 2H), 1.76-1.33 (m, 5H).

m/z [M+H]+=465; [M−H]−=463.

EXAMPLE 105

(S)-N-((S)-1-Cyano-2-(4'-(trifluoromethoxy)biphenyl-4-yl)ethyl)piperidine-2-carboxamide

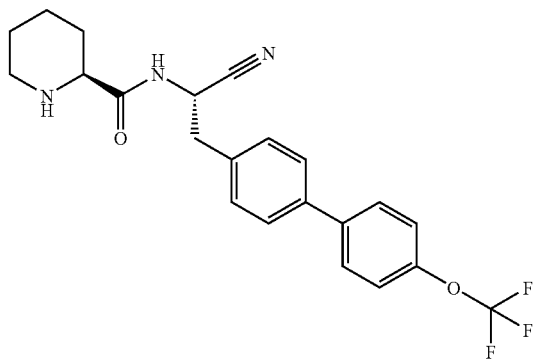

(S)-tert-Butyl 2-((S)-1-cyano-2-(4-iodophenyl)ethylcarbamoyl)piperidine-1-carboxylate (0.2 g), dichloro[1,1'-bis(di-tert-butylphosphino)ferrocene]palladium(II) (8.09 mg), 4-(trifluoromethoxy)phenylboronic acid (0.128 g) and potassium carbonate (0.114 g) were stirred and heated for 20 h at 75° C. in dioxane (15 mL), under a nitrogen atmosphere. The reaction mixture was cooled to room temperature and the mixture purified by flash silica chromatography eluting with 30% diethyl ether in isohexane to afford an oil (200 mg). The oil was dissolved in formic acid (1 mL) and the solution heated to 60° C. with stirring for approximately 10 min. The cooled solution was diluted with water (20 mL) and made basic with 0.880 aqueous ammonia. The mixture was extracted with diethyl ether (2×50 mL) and the combined extracts concentrated to give a solid. The crude material was purified by flash silica chromatography eluting with acetone to give the title compound (88 mg) as a cream coloured solid.

$^1$H NMR (399.825 MHz, CDCl$_3$+D$_2$O) δ 7.61-7.53 (m, 4H), 7.37 (d, 2H), 7.29 (d, 2H), 5.19 (t, 1H), 3.26 (dd, 1H), 3.15 (d, 2H), 2.93-2.86 (m, 1H), 2.69-2.61 (m, 1H), 1.91-1.82 (m, 1H), 1.75-1.67 (m, 1H), 1.57-1.51 (m, 1H), 1.47-1.29 (m, 3H).

m/z=418 [M+H]$^+$

EXAMPLE 106

(S)-N-((S)-1-Cyano-2-(4'-(methylsulfonyl)biphenyl-4-yl)ethyl)piperidine-2-carboxamide

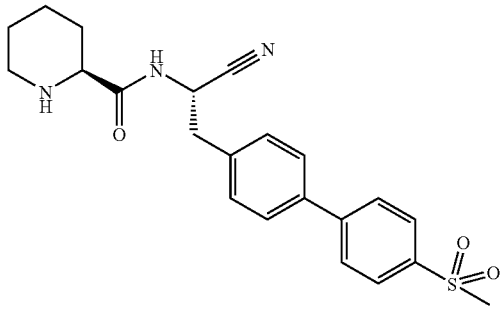

(S)-tert-Butyl 2-((S)-1-amino-1-oxo-3-(4-(4,4,5,5-tetramethyl-1,3,2-dioxaborolan-2-yl)phenyl)propan-2-ylcarbamoyl)piperidine-1-carboxylate (250 mg), potassium carbonate (207 mg), dichloro[1,1'-bis(di-tert-butylphosphino)ferrocene]palladium(II) (6.50 mg) and 1-bromo-4-(methylsulfonyl)benzene (117 mg) in dioxane (10 mL) and water (0.75 mL) were heated under a nitrogen atmosphere at 75° C. for 20 h. The cooled reaction mixture was purified by flash silica chromatography eluting with ethyl acetate to afford a foam (100 mg). The foam was stirred for 20 h in a mixture of dichloromethane (10 mL) and Burgess' reagent (135 mg). The reaction mixture was then purified by flash silica chromatography eluting with ethyl acetate to afford the product as a colourless gum (100 mg). The gum was dissolved in formic acid (0.5 mL) and stirred and heated at 50° C. for 10 minutes. The cooled reaction mixture was diluted with water (20 mL) and the solution made basic with 0.880 aqueous ammonia. The liberated base was extracted into ethyl acetate (2×25 mL), and the extracts dried over magnesium sulphate and concentrated. The residue was recrystallised from ethyl acetate (1 mL) to afford the title compound (26 mg) as a colourless solid.

$^1$H NMR (399.825 MHz, CDCl$_3$+D$_2$O) δ 8.02 (d, 2H), 7.76 (d, 2H), 7.62 (d, 2H), 7.41 (d, 2H), 5.20 (t, 1H), 3.26 (dd, 1H), 3.17 (d, 2H), 3.10 (s, 3H), 2.94-2.87 (m, 1H), 2.69-2.62 (m, 1H), 1.91-1.84 (m, 1H), 1.75-1.68 (m, 1H), 1.59-1.52 (m, 1H), 1.46-1.29 (m, 3H).

m/z=412 [M+H]$^+$

EXAMPLE 107

((2S)-N-(1-Cyano-2-(4'-(4-ethylpiperazin-1-ylsulfonyl)biphenyl-4-yl)ethyl)piperidine-2-carboxamide Ditrifluoroacetate

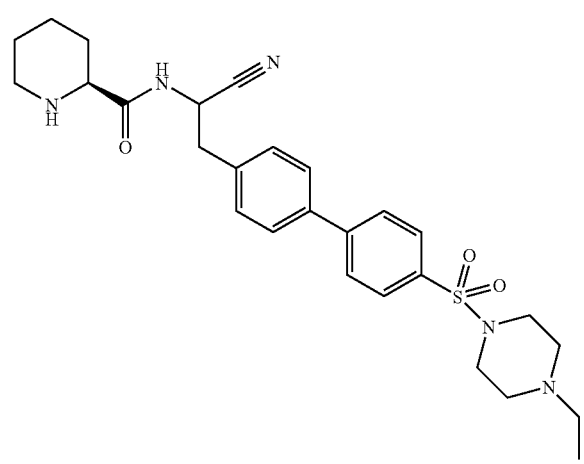

(S)-tert-Butyl 2-((S)-1-cyano-2-(4-iodophenyl)ethylcarbamoyl)piperidine-1-carboxylate (0.2 g), dichloro[1,1'-bis(di-tert-butylphosphino)ferrocene]palladium(II) (8.45 mg), 4-(4-ethylpiperazin-1-ylsulfonyl)phenylboronic acid (0.190 g) and potassium carbonate (0.114 g) were stirred and heated for 20 h at 80° C. in dioxane (15 mL) and water (0.2 mL) under a nitrogen atmosphere. The reaction mixture was cooled to room temperature and purified by flash silica chromatography, eluting with ethyl acetate to afford an oil (100 mg). The oil was dissolved in formic acid (1 mL) and the solution heated to 50° C. for ~5 minutes. The cooled solution was diluted with water (15 mL) and carefully basified with '880' aqueous ammonia. The products were extracted into ethyl acetate (30 mL) and the combined extracts were dried over magnesium sulphate, and concentrated to dryness. The crude product was purified by flash silica chromatography, eluting with acetone to afford a gum (40 mg). The crude product was purified by preparative HPLC on a Sunfire column using aqueous 0.1% TFA in acetonitrile as eluent. The fractions containing the desired compound were evaporated to dryness to yield the title compound as a solid (30 mg).

$^1$H NMR (399.825 MHz, D$_2$O) δ 7.88 (s, 4H), 7.72-7.65 (m, 2H), 7.46-7.39 (m, 2H), 5.23-5.16 (m, 0.5H), 5.08-5.01 (m, 0.5H), 4.01-3.90 (m, 2H), 3.87-3.77 (m, 1H), 3.67-3.56 (m, 2H), 3.46-3.11 (m, 8H), 3.05-2.91 (m, 1H), 2.86-2.75 (m, 2H), 2.10-2.00 (m, 0.5H), 1.93-1.33 (m, 6.5H), 1.24 (t, 3H).

m/z=510 [M+H]$^+$

EXAMPLE 108

(2S)-N-(1-Cyano-2-(4'-(4-methyl-1,4-diazepan-1-ylsulfonyl)biphenyl-4-yl)ethyl)piperidine-2-carboxamide Ditrifluoroacetate

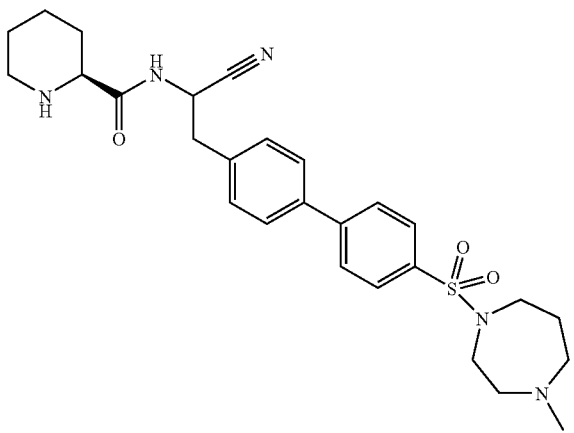

Prepared by a process analogous to that described in Example 107 using (S)-tert-butyl 2-((S)-1-cyano-2-(4-iodophenyl)ethylcarbamoyl)piperidine-1-carboxylate and 4-(4-methyl-1,4-diazepan-1-ylsulfonyl)phenylboronic acid.

$^1$H NMR (399.825 MHz, D$_2$O) δ 7.97-7.84 (m, 4H), 7.77-7.69 (m, 2H), 7.51-7.43 (m, 2H), 5.28-5.05 (m, 1H), 3.91-3.74 (m, 2H), 3.74-3.16 (m, 10H), 3.08-2.96 (m, 1H), 2.95 (s, 3H), 2.32-2.19 (m, 1H), 2.17-2.01 (m, 2H), 1.98-1.37 (m, 5H).

m/z=510 [M+H]$^+$

EXAMPLE 109

(S)-N-((S)-1-Cyano-2-(3'-(morpholinomethyl)biphenyl-4-yl)ethyl)piperidine-2-carboxamide Ditrifluoroacetate

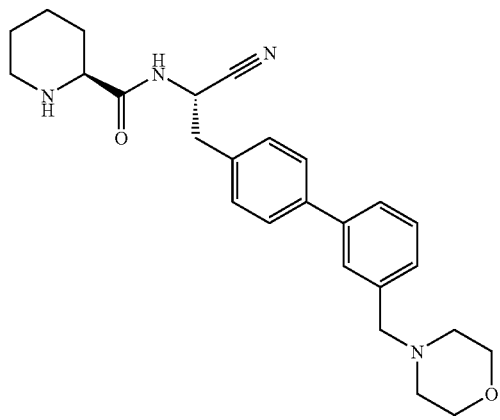

(S)-tert-Butyl 2-((S)-1-cyano-2-(4-iodophenyl)ethylcarbamoyl)piperidine-1-carboxylate (200 mg) and 1,1 bis(di-tert-butylphosphino)ferrocene palladium dichloride (2.70 mg) in dioxane (5 mL) were treated with 4-(3-(4,4,5,5-tetramethyl-1,3,2-dioxaborolan-2-yl)benzyl)morpholine (188 mg) and the mixture was stirred at room temperature for 15 min under nitrogen. An aqueous solution of potassium carbonate (2M, 0.414 mL) was added and the mixture was stirred for 18 h at 75° C. After 4 further additions of 1,1 bis(di-tert-butylphosphino)ferrocene palladium dichloride the mixture was heated for a total of 48 h. The mixture was evaporated and ethyl acetate was added. The resulting dark brown mixture was purified by flash silica chromatography, eluting with 20% ethyl acetate in isohexane and then with 40% ethyl acetate in isohexane containing 0.5% triethylamine to give a colourless oil. Formic acid (2 mL) was added and the mixture was heated at 50° C. for 12 min. The cooled mixture was basified with 0.880 aqueous ammonia and extracted with ethyl acetate. The organic layer was washed with water, dried over sodium sulphate, filtered and the solvent was evaporated. The resulting oil was purified by preparative HPLC on a Waters X-Bridge column using a 95-5% gradient of aqueous 0.1% TFA in acetonitrile as eluent. The fractions containing the desired compound were evaporated to dryness to afford the title compound (0.054 g) as a yellow oil.

$^1$H NMR (399.825 MHz, D$_2$O) δ 7.82 (d, J=7.9 Hz, 1H), 7.77 (s, 1H), 7.73-7.68 (m, 2H), 7.62 (t, J=7.8 Hz, 1H), 7.52 (d, J=7.7 Hz, 1H), 7.49-7.43 (m, 2H), 5.08 (t, J=7.8 Hz, 1H), 4.45 (s, 2H), 4.11 (d, J=12.3 Hz, 2H), 3.90-3.83 (m, 1H), 3.79 (t, J=12.3 Hz, 2H), 3.48 (d, J=12.3 Hz, 3H), 3.43-3.18 (m, 4H), 3.02 (t, J=21.7 Hz, 1H), 2.16-2.04 (m, 1H), 1.99-1.82 (m, 2H), 1.80-1.44 (m, 3H)

m/z 433 [M+H]$^+$

EXAMPLE 110

(S)-N-((S)-1-Cyano-2-(4-(1,2,3,4-tetrahydroisoquinolin-6-yl)phenyl)ethyl)piperidine-2-carboxamide Ditrifluoroacetate

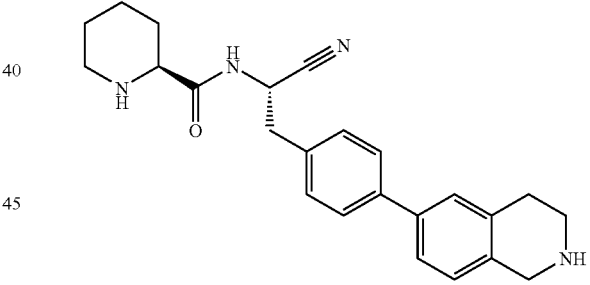

Prepared by a process analogous to that described in Example 109 using tert-butyl 6-(4,4,5,5-tetramethyl-1,3,2-dioxaborolan-2-yl)-3,4-dihydroisoquinoline-2(1H)-carboxylate to afford the title compound (0.01 g) as a colourless solid.

$^1$H NMR (399.826 MHz, d6-DMSO) δ 9.30 (d, J=7.2 Hz, 1H), 9.06 (s, 1H), 9.00-8.66 (m, 1H), 7.68-7.62 (m, 2H), 7.58-7.53 (m, 2H), 7.44-7.39 (m, 2H), 7.31 (d, J=7.9 Hz, 1H), 5.04 (q, J=7.5 Hz, 1H), 4.34-4.29 (m, 2H), 3.83-3.72 (m, 2H), 3.46-3.38 (m, 2H), 3.27-3.14 (m, 3H), 3.06 (t, J=6.2 Hz, 2H), 2.99-2.86 (m, 1H), 2.10-2.02 (m, 1H), 1.81-1.22 (m, 4H)

m/z 389 [M+H]$^+$

Biological Assay

Fluorescence Assay for Recombinant Human (rh) DPP1

The activity of DPP1 was determined by measuring the enzymatic release of aminomethyl coumarin (AMC) from the peptide substrate (H-Gly-Arg-AMC), which leads to an increase in fluorescence intensity at λex=350 nm and λem=450 nm. The assay was carried out in black 384 well plates in a final volume of 50 μl at 22° C. The assay conditions contained the following: 25 mM piperazine buffer pH5.0; 50 mM NaCl, 5 mM DTT; 0.01% (v/v) Triton X-100; 100 μM H-Gly-Arg-AMC and rhDPP1 (~50 μM). Potential inhibitors were made up in DMSO and then diluted in the assay to give a final concentration of 1% (v/v) DMSO. A 12-point half-log dilution of the inhibitors (highest concentration 10 μM) was tested and the pIC50 determined using a 4-parameter logistic equation in a non-linear curve fitting routine. A standard DPP1 inhibitor (vinyl sulfone, see below) was used as a positive control in the assay. Routinely, inhibitors were pre-incubated with rhDPP1 for 30 min prior to the addition of the peptide substrate to start the reaction for a further 60 min at 22° C. After that the plates were immediately read in a fluorescence plate reader using the above emission and excitation wavelengths [modified from Kam, C M, Gotz, M G, Koot, G, McGuire, M J, Thiele, D L, Hudig, D & Powers, J C (2004). Arch Biochem Biophys, 427, 123-134 & McGuire, M J, Lipsky, P E & Thiele, D L (1992). Arch Biochem Biophys, 295, 280-288]. The results obtained are shown in Table 1 below.

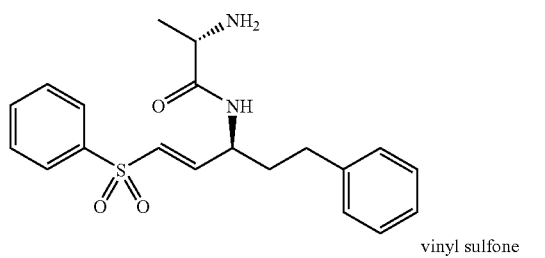

vinyl sulfone

TABLE 1

| Compound of Example | DPP1 activity, $pIC_{50}$ |
|---|---|
| 1 | 7.2 |
| 2 | 7.1 |
| 3 | 6.5 |
| 4 | 7.5 |
| 5 | 7.2 |
| 6 | 7.2 |
| 7 | 7.0 |
| 8 | 6.9 |
| 9 | 6.8 |
| 10 | 6.6 |
| 11 | 6.5 |
| 12 | 6.4 |
| 13 | 6.1 |
| 14 | 8.1 |
| 15 | 7.0 |
| 16 | 6.9 |
| 17 | 6.7 |
| 19 | 6.7 |
| 20 | 7.6 |
| 21 | 7.3 |
| 22 | 7.2 |
| 23 | 7.2 |
| 24 | 7.8 |
| 25 | 7.2 |
| 26 | 7.2 |
| 27 | 7.2 |
| 28 | 7.0 |
| 29 | 7.0 |
| 30 | 7.0 |
| 31 | 6.8 |
| 32 | 6.8 |
| 33 | 6.7 |

TABLE 1-continued

| Compound of Example | DPP1 activity, $pIC_{50}$ |
|---|---|
| 34 | 6.7 |
| 35 | 6.6 |
| 36 | 6.6 |
| 37 | 6.5 |
| 38 | 6.5 |
| 39 | 6.5 |
| 40 | 6.5 |
| 41 | 6.4 |
| 42 | 6.3 |
| 43 | 6.2 |
| 44 | 6.2 |
| 45 | 6.1 |
| 46 | 5.9 |
| 47 | 5.9 |
| 48 | 5.8 |
| 49 | 5.7 |
| 50 | 5.7 |
| 51 | 5.7 |
| 52 | 5.5 |
| 53 | 7.5 |
| 54 | 8.3 |
| 55 | 8.3 |
| 56 | 8.0 |
| 57 | 8.5 |
| 58 | 7.8 |
| 59 | 7.8 |
| 60 | 7.7 |
| 61 | 7.4 |
| 62 | 7.8 |
| 63 | 8.1 |
| 64 | 8.0 |
| 65 | 8.0 |
| 66 | 8.7 |
| 67 | 8.0 |
| 68 | 7.8 |
| 69 | 7.9 |
| 70 | 7.7 |
| 71 | 8.2 |
| 72 | 8.4 |
| 73 | 8.0 |
| 74 | 7.0 |
| 75 | 6.7 |
| 76 | 6.8 |
| 77 | 7.5 |
| 78 | 7.0 |
| 79 | 6.5 |
| 80 | 7.5 |
| 81 | 6.1 |
| 82 | 8.3 |
| 83 | 6.7 |
| 84 | 7.6 |
| 85 | 6.9 |
| 86 | 7.1 |
| 87 | 7.3 |
| 88 | 7.2 |
| 89 | 7.2 |
| 90 | 6.9 |
| 91 | 7.9 |
| 94 | 7.8 |
| 95 | 8.5 |
| 96 | 8.1 |
| 97 | 7.8 |
| 98 | 7.3 |
| 99 | 7.2 |
| 100 | 6.0 |
| 101 | 7.4 |
| 102 | 5.5 |
| 103 | 6.8 |
| 104 | 7.1 |
| 105 | 7.7 |
| 106 | 7.9 |
| 107 | 8.3 |
| 108 | 7.5 |
| 109 | 6.8 |
| 110 | 6.8 |

The invention claimed is:
1. A compound of formula (I)

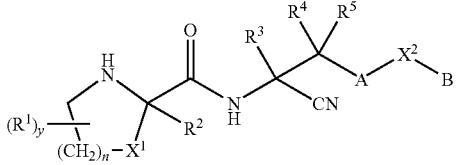

wherein
n independently represents 0, 1, 2, 3 or 4;
X$^1$ represents a methylene group;
y represents 0, 1 or 2;
each R$^1$ independently represents halogen, hydroxyl, carboxyl, cyano, C$_1$-C$_6$ alkyl, C$_1$-C$_6$ alkoxy, trifluoromethyl, NR$^6$R$^7$, C(O)NR$^6$R$^7$, NR$^{6a}$C(O)R$^{7a}$, SO$_2$NR$^6$R$^7$, NR$^{6a}$SO$_2$R$^{7a}$ or S(O)$_m$R$^8$ and R$^1$ is optionally substituted with hydroxy, halogen or C$_1$-C$_6$ alkoxy;
R$^2$ represents a hydrogen atom or a C$_1$-C$_6$ alkyl group optionally substituted by at least one substituent selected from halogen, hydroxyl, carboxyl, cyano, trifluoromethyl, C$_1$-C$_6$ alkyl, C$_3$-C$_6$ cycloalkyl, NR$^9$R$^{10}$, C(O)NR$^{11}$R$^{12}$, NR$^{13}$C(O)R$^{14}$, SO$_2$NR$^{15}$R$^{16}$, NR$^{17}$SO$_2$R$^{18}$ and S(O)$_p$R$^{19}$;
R$^3$ represents a hydrogen atom or a C$_1$-C$_6$ alkyl group optionally substituted by at least one substituent selected from halogen, hydroxyl, carboxyl, cyano, trifluoromethyl, C$_1$-C$_6$ alkyl, C$_3$-C$_6$ cycloalkyl, NR$^{20}$R$^{21}$, C(O)NR$^{22}$R$^{23}$, NR$^{24}$C(O)R$^{25}$, SO$_2$NR$^{26}$R$^{27}$, NR$^{28}$SO$_2$R$^{29}$ and S(O)$_q$R$^{30}$,
R$^4$ represents a hydrogen atom or a C$_1$-C$_6$ alkyl group optionally substituted by at least one substituent selected from halogen, hydroxyl, carboxyl, cyano, trifluoromethyl, C$_1$-C$_6$ alkyl, C$_3$-C$_6$ cycloalkyl, NR$^{31}$R$^{32}$, C(O)NR$^{33}$R$^{34}$, NR$^{35}$C(O)R$^{36}$, SO$_2$NR$^{37}$R$^{38}$, NR$^{39}$SO$_2$R$^{40}$ and S(O)$_r$R$^{41}$,
R$^5$ represents a hydrogen atom or a C$_1$-C$_6$ alkyl group optionally substituted by at least one substituent selected from halogen, hydroxyl, carboxyl, cyano, trifluoromethyl, C$_1$-C$_6$ alkyl, C$_3$-C$_6$ cycloalkyl, NR$^{42}$R$^{43}$, C(O)NR$^{44}$R$^{45}$, NR$^{46}$C(O)R$^{47}$, SO$_2$NR$^{48}$R$^{49}$, NR$^{50}$SO$_2$R$^{51}$ and S(O)$_t$R$^{52}$, or
R$^3$ and R$^4$ together with the carbon atoms to which they are attached represent a cyclopropyl ring, or
R$^4$ and R$^5$ together with the carbon atom to which they are attached form a saturated or unsaturated, 3- to 6-membered carbocyclic or heterocyclic ring which ring may be optionally substituted with at least one substituent selected from halogen, hydroxyl, carboxyl and C$_1$-C$_6$ alkyl;
A and B each independently represent a 5- to 10-membered aromatic ring system optionally comprising at least one ring heteroatom selected from nitrogen, oxygen and sulphur, the ring system being optionally substituted by at least one substituent selected from halogen, carboxyl, hydroxyl, oxo, nitro, cyano, mercapto, C$_3$-C$_6$ cycloalkyl, C$_2$-C$_6$ alkenyl, trifluoromethyl, C$_1$-C$_6$ alkoxy, C$_1$-C$_6$ alkylcarbonyl, C$_1$-C$_6$ alkylcarbonyloxy, C$_1$-C$_6$ alkoxycarbonyl, —NR$^{53}$R$^{54}$, —C(O)NR$^{55}$R$^{56}$, NR$^{57}$C(O)R$^{58}$, SO$_2$NR$^{59}$R$^{60}$, NR$^{61}$SO$_2$R$^{62}$, S(O)$_v$R$^{63}$, saturated 4- to 7-membered heterocyclyloxy, benzyloxy, C$_1$-C$_6$ alkylpiperazinyl and a C$_1$-C$_6$ alkyl group (itself optionally substituted by hydroxyl, C$_1$-C$_6$ alkoxy, NR$^{64}$R$^{65}$, phenyl or morpholinyl);
m, p, q, r, t and v each independently represent 0, 1 or 2;
X$^2$ represents a bond, an oxygen or sulphur atom, SO, SO$_2$, NR$^{66}$, C(O)NR$^{66}$, NR$^{66}$C(O), SO$_2$NR$^{66}$, NR$^{66}$SO$_2$, C$_1$-C$_3$ alkyl, ethenyl or ethynyl;
R$^6$ and R$^7$ each independently represent hydrogen, C$_1$-C$_6$ alkyl or C$_3$-C$_6$ cycloalkyl, or R$^6$ and R$^7$ together with the nitrogen atom to which they are attached form a 4- to 7-membered saturated heterocyclic ring;
R$^9$ and R$^{10}$ each independently represent hydrogen, C$_1$-C$_6$ alkyl or C$_3$-C$_6$ cycloalkyl, or R$^9$ and R$^{10}$ together with the nitrogen atom to which they are attached form a 4- to 7-membered saturated heterocyclic ring;
R$^{11}$ and R$^{12}$ each independently represent hydrogen, C$_1$-C$_6$ alkyl or C$_3$-C$_6$ cycloalkyl, or R$^{11}$ and R$^{12}$ together with the nitrogen atom to which they are attached form a 4- to 7-membered saturated heterocyclic ring;
R$^{15}$ and R$^{16}$ each independently represent hydrogen, C$_1$-C$_6$ alkyl or C$_3$-C$_6$ cycloalkyl, or R$^{15}$ and R$^{16}$ together with the nitrogen atom to which they are attached form a 4- to 7-membered saturated heterocyclic ring;
R$^{20}$ and R$^{21}$ each independently represent hydrogen, C$_1$-C$_6$ alkyl or C$_3$-C$_6$ cycloalkyl, or R$^{20}$ and R$^{21}$ together with the nitrogen atom to which they are attached form a 4- to 7-membered saturated heterocyclic ring;
R$^{22}$ and R$^{23}$ each independently represent hydrogen, C$_1$-C$_6$ alkyl or C$_3$-C$_6$ cycloalkyl, or R$^{22}$ and R$^{23}$ together with the nitrogen atom to which they are attached form a 4- to 7-membered saturated heterocyclic ring;
R$^{26}$ and R$^{27}$ each independently represent hydrogen, C$_1$-C$_6$ alkyl or C$_3$-C$_6$ cycloalkyl, or R$^{26}$ and R$^{27}$ together with the nitrogen atom to which they are attached form a 4- to 7-membered saturated heterocyclic ring;
R$^{31}$ and R$^{32}$ each independently represent hydrogen, C$_1$-C$_6$ alkyl or C$_3$-C$_6$ cycloalkyl, or R$^{31}$ and R$^{32}$ together with the nitrogen atom to which they are attached form a 4- to 7-membered saturated heterocyclic ring;
R$^{33}$ and R$^{34}$ each independently represent hydrogen, C$_1$-C$_6$ alkyl or C$_3$-C$_6$ cycloalkyl, or R$^{33}$ and R$^{34}$ together with the nitrogen atom to which they are attached form a 4- to 7-membered saturated heterocyclic ring;
R$^{37}$ and R$^{38}$ each independently represent hydrogen, C$_1$-C$_6$ alkyl or C$_3$-C$_6$ cycloalkyl, or R$^{37}$ and R$^{38}$ together with the nitrogen atom to which they are attached form a 4- to 7-membered saturated heterocyclic ring;
R$^{42}$ and R$^{43}$ each independently represent hydrogen, C$_1$-C$_6$ alkyl or C$_3$-C$_6$ cycloalkyl, or R$^{42}$ and R$^{43}$ together with the nitrogen atom to which they are attached form a 4- to 7-membered saturated heterocyclic ring;
R$^{44}$ and R$^{45}$ each independently represent hydrogen, C$_1$-C$_6$ alkyl or C$_3$-C$_6$ cycloalkyl, or R$^{44}$ and R$^{45}$ together with the nitrogen atom to which they are attached form a 4- to 7-membered saturated heterocyclic ring;
R$^{48}$ and R$^{49}$ each independently represent hydrogen, C$_1$-C$_6$ alkyl or C$_3$-C$_6$ cycloalkyl, or R$^{48}$ and R$^{49}$ together with the nitrogen atom to which they are attached form a 4- to 7-membered saturated heterocyclic ring;
R$^{53}$ and R$^{54}$ each independently represent hydrogen, C$_1$-C$_6$ alkyl or C$_3$-C$_6$ cycloalkyl, or R$^{53}$ and R$^{54}$ together with the nitrogen atom to which they are attached form a 4- to 7-membered saturated heterocyclic ring;
R$^{55}$ and R$^{56}$ each independently represent hydrogen, C$_1$-C$_6$ alkyl or C$_3$-C$_6$ cycloalkyl, or R$^{55}$ and R$^{56}$ together with the nitrogen atom to which they are attached form a 4- to 7-membered saturated heterocyclic ring;

129

R$^{59}$ and R$^{60}$ each independently represent hydrogen, C$_1$-C$_6$ alkyl or C$_3$-C$_6$ cycloalkyl, or R$^{59}$ and R$^{60}$ together with the nitrogen atom to which they are attached form a 4- to 7-membered saturated heterocyclic ring;

R$^{64}$ and R$^{65}$ each independently represent hydrogen, C$_1$-C$_6$ alkyl or C$_3$-C$_6$ cycloalkyl, or R$^{64}$ and R$^{65}$ together with the nitrogen atom to which they are attached form a 4- to 7-membered saturated heterocyclic ring;

each group R$^{6a}$, R$^{7a}$, R$^8$, R$^{13}$, R$^{14}$, R$^{17}$, R$^{18}$, R$^{19}$, R$^{24}$, R$^{25}$, R$^{28}$, R$^{29}$, R$^{30}$, R$^{35}$, R$^{36}$, R$^{39}$, R$^{40}$, R$^{41}$, R$^{46}$, R$^{47}$, R$^{50}$, R$^{51}$, R$^{52}$, R$^{57}$, R$^{58}$, R$^{61}$, R$^{62}$, and R$^{63}$ independently represents a hydrogen atom or a C$_1$-C$_6$ alkyl or C$_3$-C$_6$ cycloalkyl group; and R$^{66}$ represents a hydrogen atom or a C$_1$-C$_6$ alkyl group; or a pharmaceutically acceptable salt thereof.

2. A compound according to claim 1 wherein n is 2.

3. A compound according to claim 1 or claim 2, wherein X$^1$ is methylene.

4. A compound according to any one of claims 1 to 3, wherein R$^2$ represents a hydrogen atom.

5. A compound according to claim 1, wherein R$^3$, R$^4$ and R$^5$ each represent a hydrogen atom.

6. A compound according to claim 1, wherein A represents phenyl.

7. A compound according to claim 1, wherein B represents a 5- to 10-membered aromatic ring system optionally comprising one or two ring heteroatoms independently selected from nitrogen, oxygen and sulphur, the ring system being optionally substituted by at least one substituent selected from halogen, carboxyl, hydroxyl, cyano, C$_1$-C$_6$ alkoxy, —NR$^{53}$R$^{54}$, —C(O)NR$^{55}$R$^{56}$, NR$^{57}$C(O)R$^{58}$, SO$_2$NR$^{59}$R$^{60}$, S(O)$_r$R$^{63}$, pyrrolidinyloxy, benzyloxy, methylpiperazinyl and C$_1$-C$_6$alkyl (itself optionally substituted by hydroxyl, C$_1$-C$_6$ alkoxy, NR$^{64}$R$^{65}$, phenyl or morpholinyl).

8. A compound according to claim 7, wherein the aromatic ring system in B is selected from phenyl, pyrazolyl, pyridinyl, indolyl, oxazolyl, quinolinyl, pyrimidinyl and thienyl.

9. A compound according to claim 1, wherein X$^2$ represents a bond.

10. A compound according to claim 1 being:
(S)-N-((S)-2-(3'-Chlorobiphenyl-4-yl)-1-cyanoethyl)piperidine-2-carboxamide,
(S)-N-((S)-1-Cyano-2-(3'-(piperidin-1-ylmethyl)biphenyl-4-yl)ethyl)piperidine-2-carboxamide,
(S)-N-((S)-2-(biphenyl-4-yl)-1-cyanoethyl)pyrrolidine-2-carboxamide,
(S)-N-((S)-2-(4-(1-Benzyl-1H-pyrazol-4-yl)phenyl)-1-cyanoethyl)-piperidine-2-carboxamide,
(S)-N-((S)-2-(4'-Carbamoylbiphenyl-4-yl)-1-cyanoethyl)piperidine-2-carboxamide,
(S)-N-((S)-1-Cyano-2-(3'-cyanobiphenyl-4-yl)ethyl)piperidine-2-carboxamide,
(S)-N-((S)-2-(3'-(Aminomethyl)biphenyl-4-yl)-1-cyanoethyl)piperidine-2-carboxamide,
(S)-N-((S)-2-(3'-Acetamidobiphenyl-4-yl)-1-cyanoethyl) piperidine-2-carboxamide,
(S)-N-((S)-1-Cyano-2-(4'-(morpholinomethyl)biphenyl-4-yl)ethyl)piperidine-2-carboxamide,
(S)-N-((S)-1-Cyano-2-(4-(pyridin-3-yl)phenyl)ethyl)piperidine-2-carboxamide,
(S)-N-((S)-1-Cyano-2-(4'-hydroxy-2'-methylbiphenyl-4-yl)ethyl)piperidine-2-carboxamide,
4'-((S)-2-Cyano-2-((S)-piperidine-2-carboxamido)ethyl) biphenyl-3-carboxylic acid,
(S)-N-((S)-1-Cyano-2-(2'-((R)-pyrrolidin-3-yloxy)biphenyl-4-yl)ethyl)piperidine-2-carboxamide,

130

(S)-N-((S)-2-(4-(1H-Indol-2-yl)phenyl)-1-cyanoethyl)piperidine-2-carboxamide,
(2S)-N-[(1S)-1-cyano-2-(3'-methoxybiphenyl-4-yl)ethyl] piperidine-2-carboxamide,
Piperidine-2-carboxylic acid (2-biphenyl-4-yl-1-cyanoethyl)-amide,
(2S,4R)-N-((S)-2-(biphenyl-4-yl)-1-cyanoethyl)-4-hydroxypyrrolidine-2-carboxamide,
(S)-N-((S)-1-cyano-2-(3'-cyanobiphenyl-4-yl)ethyl)azetidine-2-carboxamide,
(2S)-N-[(1S)-1-Cyano-2-[4-[4-(dimethylsulfamoyl)phenyl]phenyl]ethyl]piperidine-2-carboxamide,
(2S)-N-[(1S)-1-Cyano-2-(4-1,2-oxazol-4-ylphenyl)ethyl] piperidine-2-carboxamide,
(2S)-N-[(1S)-1-Cyano-2-[4-(3-methylsulfanylphenyl) phenyl]ethyl]piperidine-2-carboxamide,
(2S)-N-[(1S)-1-Cyano-2-[4-(4-hydroxyphenyl)phenyl] ethyl]piperidine-2-carboxamide,
(2S)-N-[(1S)-1-Cyano-2-[4-(4-cyanophenyl)phenyl] ethyl]piperidine-2-carboxamide,
(2S)-N-[(1S)-1-Cyano-2-[4-(4-methoxyphenyl)phenyl] ethyl]piperidine-2-carboxamide,
(2S)-N-[(1S)-1-Cyano-2-[4-(2-methylpyrazol-4-yl)phenyl]ethyl]piperidine-2-carboxamide,
(2S)-N-[(1S)-1-Cyano-2-[4-[3-hydroxypropyl)phenyl] phenyl]ethyl]piperidine-2-carboxamide,
(2S)-N-[(1S)-2-(4-Benzo[1,3]dioxol-5-ylphenyl)-1-cyano-ethyl]piperidine-2-carboxamide,
(2S)-N-[(1S)-1-Cyano-2-[4-(3,4-difluorophenyl)phenyl] ethyl]piperidine-2-carboxamide,
(2S)-N-[(1S)-1-Cyano-2-[4-(4-fluoro-2-phenylmethoxyphenyl)phenyl]ethyl]piperidine-2-carboxamide,
(2S)-N-[(1S)-1-Cyano-2-[4-(3-fluoro-4-methoxy-phenyl) phenyl]ethyl]piperidine-2-carboxamide,
(2S)-N-[(1S)-1-Cyano-2-[4-(3,4-dimethoxyphenyl)phenyl]ethyl]piperidine-2-carboxamide,
(2S)-N-[(1S)-1-Cyano-2-[4-(2,4-dimethoxyphenyl)phenyl]ethyl]piperidine-2-carboxamide,
(2S)-N-[(1S)-2-[4-(3-Carbamoylphenyl)phenyl]-1-cyano-ethyl]piperidine-2-carboxamide,
(2S)-N-[(1S)-1-Cyano-2-[4-(2,5-dioxabicyclo[4.4.0] deca-7,9,11-trien-8-yl)phenyl]ethyl]piperidine-2-carboxamide,
(2S)-N-[(1S)-2-[4-[4-(Aminomethyl)phenyl]phenyl]-1-cyano-ethyl]piperidine-2-carboxamide,
(2S)-N-[(1S)-1-Cyano-2-[4-(2-dimethylaminopyrimidin-5-yl)phenyl]ethyl]piperidine-2-carboxamide,
(2S)-N-[(1S)-1-Cyano-2-[4-(4-methylthiophen-3-yl)phenyl]ethyl]piperidine-2-carboxamide,
(2S)-N-[(1S)-1-Cyano-2-[4-(3-fluoro-4-propoxy-phenyl) phenyl]ethyl]piperidine-2-carboxamide,
(2S)-N-[(1S)-1-Cyano-2-[4-(2-methoxypyridin-3-yl)phenyl]ethyl]piperidine-2-carboxamide,
(2S)-N-[(1S)-1-Cyano-2-[4-(2-methylpyrazol-3-yl)phenyl]ethyl]piperidine-2-carboxamide,
(2S)-N-[(1S)-1-Cyano-2-[4-[3-(dimethylcarbamoyl)phenyl]phenyl]ethyl]piperidine-2-carboxamide,
(2S)-N-[(1S)-1-Cyano-2-[4-(4-ethylsulfonyl-2-methylphenyl)phenyl]ethyl]piperidine-2-carboxamide,
(2S)-N-[(1S)-1-Cyano-2-[4-(3,5-difluoro-2-methoxy-phenyl)phenyl]ethyl]piperidine-2-carboxamide,
(2S)-N-[(1S)-1-Cyano-2-[4-[3-(hydroxymethyl)phenyl] phenyl]ethyl]piperidine-2-carboxamide,
(2S)-N-[(1S)-1-Cyano-2-[4-(2-methoxypyrimidin-5-yl) phenyl]ethyl]piperidine-2-carboxamide,
(2S)-N-[(1S)-1-Cyano-2-[4-[6-(4-methylpiperazin-1-yl) pyridin-3-yl]phenyl]ethyl]piperidine-2-carboxamide, (2S)-N-[(1S)-1-Cyano-2-[4-(2-hydroxyphenyl)phenyl]ethyl]piperidine-2-carboxamide,
(2S)-N-[(1S)-1-Cyano-2-(4-quinolin-8-ylphenyl)ethyl]piperidine-2-carboxamide,
(2S)-N-[(1S)-1-Cyano-2-[4-(2-methylphenyl)phenyl]ethyl]piperidine-2-carboxamide,
(2S)-N-[(1S)-1-Cyano-2-[4-(2-phenylmethoxyphenyl)phenyl]ethyl]piperidine-2-carboxamide,
(2S)-N-[(1S)-1-Cyano-2-[4-(2-methylpyridin-3-yl)phenyl]ethyl]piperidine-2-carboxamide,
(S)-N-((S)-1-Cyano-2-(4-(6-cyanopyridin-3-yl)phenyl)ethyl)piperidine-2-carboxamide,
(S)-N-((S)-1-Cyano-2-(4-(3-(2-hydroxyethyl)-2-oxo-2,3-dihydrobenzo[d]thiazol-5-yl)phenyl)ethyl)piperidine-2-carboxamide,
(S)-N-((S)-1-cyano-2-(4-(3-(2-methoxyethyl)-2-oxo-2,3-dihydrobenzo[d]thiazol-5-yl)phenyl)ethyl)piperidine-2-carboxamide,
(S)-N-((S)-1-Cyano-2-(4'-cyano-3'-fluorobiphenyl-4-yl)ethyl)piperidine-2-carboxamide,
(S)-N-((S)-1-Cyano-2-(4'-cyano-3'-(methylthio)biphenyl-4-yl)ethyl)-piperidine-2-carboxamide,
(S)-N-((S)-1-Cyano-2-(4'-cyano-3'-(methylsulfonyl)biphenyl-4-yl)ethyl)piperidine-2-carboxamide,
(S)-N-((S)-1-Cyano-2-(4'-cyano-3'-(ethylsulfonyl)biphenyl-4-yl)ethyl)piperidine-2-carboxamide,
(S)-N-((S)-1-Cyano-2-(4'-cyano-3'-(propylsulfonyl)biphenyl-4-yl)ethyl)piperidine-2-carboxamide,
(2S)-N-((1S)-2-(4'-Carbamoyl-3'-(methylsulfinyl)biphenyl-4-yl)-1-cyanoethyl)piperidine-2-carboxamide,
(2S)-N-((1S)-1-Cyano-2-(4'-cyano-3'-(2-methyl-1H-imidazol-1-yl)biphenyl-4-yl)ethyl)piperidine-2-carboxamide,
(S)-N-((S)-1-cyano-2-(3'-cyano-4'-(methylthio)biphenyl-4-yl)ethyl)piperidine-2-carboxamide,
(S)-N-((S)-1-Cyano-2-(3'-cyano-4'-(methylsulfonyl)biphenyl-4-yl)ethyl)piperidine-2-carboxamide,
(S)-tert-Butyl 2-((S)-1-cyano-2-(3'-cyano-4'-(propylsulfonyl)biphenyl-4-yl)ethylcarbamoyl)piperidine-1-carboxylate,
(S)-N-((S)-1-Cyano-2-(4-(3-methyl-2-oxo-2,3-dihydrobenzo[d]thiazol-5-yl)phenyl)ethyl)piperidine-2-carboxamide,
(2S)-N-{(1S)-1-Cyano-2-[4-(1,1-dioxido-2,3-dihydro-1,2-benzisothiazol-5-yl)phenyl]ethyl}piperidine-2-carboxamide,
(S)-N-((S)-1-Cyano-2-(4-(3-oxo-3,4-dihydro-2H-benzo[b][1,4]thiazin-7-yl)phenyl)ethyl)piperidine-2-carboxamide,
2S)-N-{(1S)-1-Cyano-2-[4-(2-methyl-1,1-dioxido-2,3-dihydro-1,2-benzisothiazol-5-yl)phenyl]ethyl}piperidine-2-carboxamide,
(S)-N-((S)-1-Cyano-2-(4'-ethylbiphenyl-4-yl)ethyl)piperidine-2-carboxamide trifluoroacetate,
(S)-N-((S)-1-Cyano-2-(4'-(N-methylsulfamoyl)biphenyl-4-yl)ethyl)piperidine-2-carboxamide trifluoroacetate,
(S)-N-((S)-2-(4'-(Azetidin-1-ylsulfonyl)biphenyl-4-yl)-1-cyanoethyl)piperidine-2-carboxamide trifluoroacetate,
(S)-N-((S)-1-Cyano-2-(4'-(N-(2-hydroxyethyl)sulfamoyl)biphenyl-4-yl)ethyl)piperidine-2-carboxamide,
(S)-N-((S)-1-Cyano-2-(4'-(methylcarbamoyl)biphenyl-4-yl)ethyl)piperidine-2-carboxamide trifluoroacetate,
(S)-N-((S)-1-Cyano-2-(4'-(pyrrolidine-1-carbonyl)biphenyl-4-yl)ethyl)piperidine-2-carboxamide trifluoroacetate,
(S)-N-((S)-1-Cyano-2-(4'-(4-methylpiperazine-1-carbonyl)biphenyl-4-yl)ethyl)piperidine-2-carboxamide trifluoroacetate,
(S)-N-((S)-1-Cyano-2-(6-(4-cyanophenyl)pyridin-3-yl)ethyl)piperidine-2-carboxamide trifluoroacetate,
(S)-N-((S)-1-Cyano-2-(6-(3-cyanophenyl)pyridin-3-yl)ethyl)piperidine-2-carboxamide trifluoroacetate,
(S)-N-((S)-1-Cyano-2-(6-(2-hydroxyphenyl)pyridin-3-yl)ethyl)piperidine-2-carboxamide,
(S)-N-((S)-1-Cyano-2-(6-(4-(N,N-dimethylsulfamoyl)phenyl)pyridin-3-yl)ethyl)piperidine-2-carboxamide trifluoroacetate,
(S)-N-((S)-2-(6-(3-Chloro-5-(dimethylcarbamoyl)phenyl)pyridin-3-yl)-1-cyanoethyl)piperidine-2-carboxamide trifluoroacetate,
(S)-N-((S)-1-Cyano-2-(4'-(trifluoromethyl)biphenyl-4-yl)ethyl)piperidine-2-carboxamide trifluoroacetate,
(S)-N-((S)-1-Cyano-2-(3'-(piperidine-1-carbonyl)biphenyl-4-yl)ethyl)piperidine-2-carboxamide trifluoroacetate,
(S)-N-((S)-1-Cyano-2-(3'-(thiazol-2-ylcarbamoyl)biphenyl-4-yl)ethyl)piperidine-2-carboxamide trifluoroacetate,
(S)-N-((S)-1-Cyano-2-(3'-(2-cyanoethylcarbamoyl)biphenyl-4-yl)ethyl)piperidine-2-carboxamide,
(S)-N-((S)-2-(3'-(2-amino-2-oxoethyl)biphenyl-4-yl)-1-cyanoethyl)piperidine-2-carboxamide trifluoroacetate,
(S)-N-((S)-1-Cyano-2-(3'-(N,N-dimethylsulfamoyl)biphenyl-4-yl)ethyl)piperidine-2-carboxamide trifluoroacetate,
(S)-N-((S)-1-Cyano-2-(3'-(pyrrolidin-1-ylsulfonyl)biphenyl-4-yl)ethyl)piperidine-2-carboxamide trifluoroacetate,
(S)-N-((S)-1-Cyano-2-(3'-(methylsulfonamidomethyl)biphenyl-4-yl)ethyl)piperidine-2-carboxamide trifluoroacetate,
(S)-N-((S)-2-(3'-(Acetamidomethyl)biphenyl-4-yl)-1-cyanoethyl)-piperidine-2-carboxamide trifluoroacetate,
(S)-N-((S)-1-Cyano-2-(4'-(4-cyanopiperidin-1-ylsulfonyl)biphenyl-4-yl)ethyl)piperidine-2-carboxamide trifluoroacetate,
(S)-N-((S)-1-Cyano-2-(4'-(morpholinosulfonyl)biphenyl-4-yl)ethyl)piperidine-2-carboxamide trifluoroacetate,
(S)-N-((S)-1-Cyano-2-(4'-(4-methylpiperazin-1-ylsulfonyl)biphenyl-4-yl)ethyl)piperidine-2-carboxamide trifluoroacetate,
(S)-N-((S)-1-Cyano-2-(4-(3-methyl-2-oxo-2,3-dihydrobenzo[d]oxazol-5-yl)phenyl)ethyl)piperidine-2-carboxamide,
(S)-N-((S)-1-Cyano-2-(4-(3-(2-methoxyethyl)-2-oxo-2,3-dihydrobenzo[d]-oxazol-5-yl)phenyl)ethyl)piperidine-2-carboxamide,
(S)-N-((S)-1-Cyano-2-(4-(3-methyl-2-oxo-2,3-dihydrobenzo[d]thiazol-6-yl)phenyl)ethyl)piperidine-2-carboxamide,
(S)-N-((S)-1-Cyano-2-(4-(3-(2-hydroxyethyl)-2-oxo-2,3-dihydrobenzo[d]thiazol-6-yl)phenyl)ethyl)piperidine-2-carboxamide,
(S)-N-((S)-1-Cyano-2-(4'-cyanobiphenyl-3-yl)ethyl)piperidine-2-carboxamide trifluoroacetate,
(S)-N-((S)-1-Cyano-2-(4'-(cyanomethyl)-3'-(methylsulfonyl)biphenyl-4-yl)ethyl)-piperidine-2-carboxamide trifluoroacetate, (S)-N-((S)-1-Cyano-2-(4-(phenylsulfonyl)phenyl)ethyl)piperidine-2-carboxamide, (S)-N-((1R,2R)-1-Cyano-2-(4'-cyanobiphenyl-4-yl)cyclopropyl)piperidine-2-carboxamide trifluoroacetate, (S)-N-((1R,2R)-2-(4'-(Azetidin-1-ylsulfonyl)biphenyl-4-yl)-1-cyanocyclopropyl)piperidine-2-carboxamide trifluoroacetate, (S)-N-((S)-1-Cyano-2-(4'-(trifluoromethoxy)biphenyl-4-yl)ethyl)piperidine-2-carboxamide, (S)-N-((S)-1-Cyano-2-(4'-(methylsulfonyl)biphenyl-4-yl)ethyl)piperidine-2-carboxamide, ((2S)-N-(1-Cyano-2-(4'-(4-ethylpiperazin-1-ylsulfonyl)biphenyl-4-yl)ethyl)piperidine-2-carboxamide ditrifluoroacetate, (2S)-N-(1-Cyano-2-(4'-(4-methyl-1,4-diazepan-1-ylsulfonyl)biphenyl-4-yl)ethyl)piperidine-2-carboxamide ditrifluoroacetate, (S)-N-((S)-1-Cyano-2-(3'-(morpholinomethyl)biphenyl-4-yl)ethyl)piperidine-2-carboxamide ditrifluoroacetate, or (S)-N-((S)-1-Cyano-2-(4-(1,2,3,4-tetrahydroisoquinolin-6-yl)phenyl)ethyl)piperidine-2-carboxamide ditrifluoroacetate or a pharmaceutically acceptable salt thereof.

11. A process for the preparation of a compound of formula (I) or a pharmaceutically acceptable salt thereof as defined in claim 1 which comprises reacting a compound of formula (II)

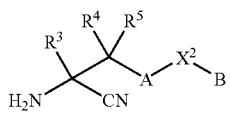

(II)

wherein $R^3$, $R^4$, $R^5$, A, $X^2$ and B are as defined in formula (I), with a compound of formula (III)

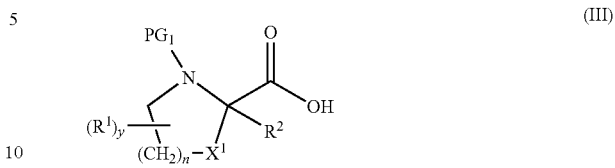

(III)

wherein $PG_1$ represents a protecting group and n, $X^1$, y, $R^1$ and $R^2$ are as defined in formula (I), and optionally thereafter carrying out one or more of the following procedures:

converting a compound of formula (I) into another compound of formula (I)

removing any protecting groups forming a pharmaceutically acceptable salt.

12. A pharmaceutical composition comprising a compound of formula (I) or a pharmaceutically acceptable salt thereof as claimed in claim 1 in association with a pharmaceutically acceptable adjuvant, diluent or carrier.

13. A combination of a compound of formula (I) or a pharmaceutically acceptable salt thereof as claimed in claim 1 and one or more agents independently selected from:

a non-steroidal glucocorticoid receptor agonist;

a selective $β_2$ adrenoceptor agonist;

a phosphodiesterase inhibitor;

a protease inhibitor;

a glucocorticoid;

an anticholinergic agent;

a modulator of chemokine receptor function; and an inhibitor of kinase function.

* * * * *

UNITED STATES PATENT AND TRADEMARK OFFICE
CERTIFICATE OF CORRECTION

PATENT NO. : 7,902,181 B2  Page 1 of 1
APPLICATION NO. : 12/331719
DATED : March 8, 2011
INVENTOR(S) : Peter Alan Cage et al.

It is certified that error appears in the above-identified patent and that said Letters Patent is hereby corrected as shown below:

Column 130, line 23, "[4-(2-" should read -- [4-(1 --.

Column 130, line 25, "[4-[3-" should read -- [4-[4-(3- --.

Signed and Sealed this
Twenty-second Day of November, 2011

David J. Kappos
*Director of the United States Patent and Trademark Office*